US011571549B2

(12) United States Patent
Kanemasa et al.

(10) Patent No.: US 11,571,549 B2
(45) Date of Patent: Feb. 7, 2023

(54) MEDICAL DEVICE

(71) Applicant: SUMITOMO BAKELITE CO., LTD., Shinagawa-ku (JP)

(72) Inventors: Kenichi Kanemasa, Akita (JP); Iji Onozuka, Akita (JP)

(73) Assignee: SUMITOMO BAKELITE CO., LTD., Shinagawa-ku (JP)

( * ) Notice: Subject to any disclaimer, the term of this patent is extended or adjusted under 35 U.S.C. 154(b) by 357 days.

(21) Appl. No.: 16/631,242

(22) PCT Filed: Aug. 2, 2018

(86) PCT No.: PCT/JP2018/029101
§ 371 (c)(1),
(2) Date: Jan. 15, 2020

(87) PCT Pub. No.: WO2019/027013
PCT Pub. Date: Feb. 7, 2019

(65) Prior Publication Data
US 2020/0215308 A1    Jul. 9, 2020

(30) Foreign Application Priority Data

Aug. 2, 2017  (JP) ............................. JP2017-150210
Aug. 2, 2017  (JP) ............................. JP2017-150211

(51) Int. Cl.
*A61M 25/01*  (2006.01)
*A61M 25/00*  (2006.01)

(52) U.S. Cl.
CPC .... *A61M 25/0147* (2013.01); *A61M 25/0136* (2013.01); *A61M 25/0138* (2013.01);
(Continued)

(58) Field of Classification Search
CPC .......... A61M 25/0147; A61M 25/0136; A61M 25/0138; A61M 2025/015;
(Continued)

(56) References Cited

U.S. PATENT DOCUMENTS 5,413,107 A * 5/1995 Oakley ............. A61M 25/0136
600/463
2004/0059288 A1 * 3/2004 Webler .............. A61M 25/0147
604/95.04
(Continued)

FOREIGN PATENT DOCUMENTS

CN   103156686 A   6/2013
CN   104883945 A   9/2015
(Continued)

OTHER PUBLICATIONS

International Search Report dated Oct. 30, 2018 in PCT/JP2018/029101 filed on Aug. 2, 2018, 1 page.
(Continued)

*Primary Examiner* — Jenna Zhang
(74) *Attorney, Agent, or Firm* — Oblon, McClelland, Maier & Neustadt, L.L.P.

(57) ABSTRACT

A medical device includes a medical device body, first and second operating lines inserted in axial direction of the device body, and a bending operating part that pulls the operating lines to perform bending operation of a distal end part of the device body. The device body has the distal end part in the axial direction such that the operating lines are gradually curved and approach each other in circumferential direction of the device body toward a distal end side in the distal end part. The device body has a curved region and a parallel region such that in the curved region, the operating lines gradually curve and approach each other in the circumferential direction toward the distal end side and that in a parallel region, the operating lines extend in parallel to
(Continued)

each other between the distal end of the curved region and distal ends of the operating lines.

28 Claims, 40 Drawing Sheets

(52) U.S. Cl.
 CPC ....... *A61M 25/005* (2013.01); *A61M 25/0108* (2013.01); *A61M 2025/015* (2013.01)
(58) Field of Classification Search
 CPC ............. A61M 25/0133; A61B 1/0057; A61B 1/0052; A61B 1/0051
 See application file for complete search history.

(56) References Cited

U.S. PATENT DOCUMENTS

| | | | |
|---|---|---|---|
| 2006/0100640 A1* | 5/2006 | Bolduc | A61B 17/00234 |
| | | | 606/108 |
| 2006/0167467 A1 | 7/2006 | Rourke | |
| 2006/0252993 A1 | 11/2006 | Freed et al. | |
| 2008/0312506 A1* | 12/2008 | Spivey | A61M 25/0138 |
| | | | 600/149 |
| 2015/0202409 A1* | 7/2015 | Kanemasa | F16C 1/20 |
| | | | 604/95.04 |
| 2016/0206853 A1 | 7/2016 | Bolduc et al. | |
| 2017/0156711 A1 | 6/2017 | Jogasaki et al. | |
| 2020/0171276 A1* | 6/2020 | Onozuka | A61M 25/001 |

FOREIGN PATENT DOCUMENTS

| | | |
|---|---|---|
| EP | 2 604 174 A1 | 6/2013 |
| JP | 2011-251068 A1 | 12/2011 |
| JP | 2013-48711 A | 3/2013 |
| JP | 2014-188212 A | 10/2014 |
| JP | 2016-518203 A | 6/2016 |
| WO | WO 2014/093457 A1 | 6/2014 |
| WO | WO 2014/184665 A2 | 11/2014 |

OTHER PUBLICATIONS

International Search Report dated Oct. 30, 2018 in PCT/JP2018/029023 filed on Aug. 2, 2018, 8 pages (with English translation).

* cited by examiner

MEDICAL DEVICE

TECHNICAL FIELD

The present invention relates to a medical device.

Priority is claimed on Japanese Patent Application No. 2017-150210 and Japanese Patent Application No. 2017-150211, filed Aug. 2, 2017, the contents of which are incorporated herein by reference.

BACKGROUND ART

As an elongated medical device, such as a catheter capable of bending a distal end part, a type having operating lines is known (for example, PTL 1).

In the catheter of PTL 1, a plurality of hollow tubes are disposed around a central lumen, and operating lines are respectively inserted through the two hollow tubes that face each other via the central lumen. In the catheter of this document, distal ends of the operating lines are fixed to the distal end part of the catheter. The catheter of this document is configured to pull rear ends of the operating lines. Accordingly, the distal end part of the catheter can be bent by selecting and pulling an operating line.

CITATION LIST

Patent Literature

[PTL 1] Japanese Unexamined Patent Application, First Publication No. 2013-48711

SUMMARY OF INVENTION

Technical Problem

However, in the catheter of PTL 1, when the distal end part is further bent after passing through a body cavity, such as a curved blood vessel, the distal end part can be easily bent in an inward direction of the curve. However, the distal end part is not easily bent in an outward direction.

This is because, if an operating line located on an out-course side of the curve is pulled to bend a distal end of the catheter in the outward direction, the catheter may rotate in a direction in which the path of the pulled operating line becomes short and around the axis of the catheter within a curved blood vessel.

The invention has been made in view of the above problem, and provides a medical device, such as a catheter having a structure capable of more reliably bending a distal end part in a desired direction.

Solution to Problem

The invention provides a medical device including an elongated medical device body;

a first operating line and a second operating line that are inserted in an axial direction of the medical device body; and a bending operating part for performing a bending operation of a distal end part of the medical device body by pulling the first operating line and the second operating line, in which at an intermediate part and a proximal end part in the axial direction of the medical device body, the first operating line and the second operating line extending in parallel so as to be spaced apart from each other in a circumferential direction of the medical device body, and at a distal end part in the axial direction of the medical device body, the first operating line and the second operating line being gradually curved so as to approach each other in the circumferential direction of the medical device body toward a distal end side and joined together.

Additionally, the invention provides a medical device including an elongated medical device body configured to include an elongated resin tube having a lumen, and a first hollow tube and a second hollow tube that are buried in an axial direction of the resin tube and allows the first operating line and the second operating line to be respectively inserted therethrough, and a bending operating part for performing a bending operation of a distal end part of the medical device body by pulling the first operating line and the second operating line, in which at an intermediate part and a proximal end part in the axial direction of the medical device body, the first operating line and the second operating line extend in parallel so as to be spaced apart from each other in a circumferential direction of the medical device body, at a distal end part in the axial direction of the medical device body, a curved region where the first operating line and the second operating line are gradually curved so as to approach each other in the circumferential direction of the medical device body toward a distal end side is formed, and a distal end of the first operating line and a distal end of the second operating line are spaced apart from each other in the circumferential direction of the medical device body, and are fixed to the medical device body.

Advantageous Effects of Invention

According to the invention, it is possible to more reliably bend the distal end part in a desired direction.

DESCRIPTION OF EMBODIMENTS

Hereinafter, embodiments of the invention will be described with reference to the drawings. In all the drawings, the same components will be designated by the same reference signs, and the detailed description thereof will be omitted.

Various components of medical devices related to the present embodiments do not need to be individually independent, and it is allowed that a plurality of components are formed as one member, one component is formed by a plurality of members, a certain component is a portion of another component, a portion of a certain component and a portion of another component overlap each other, and the like.

Terms used when describing the embodiments of the invention are defined as follows unless otherwise noted.

In the description of the embodiments, there are cases where terms, such as a distal end part and a proximal end part, are used. The distal end part refers to a predetermined length region including an end (distal end) on an insertion distal end side of a medical device in respective units of the medical device. Additionally, the proximal end part refers to a predetermined length region including an end (proximal end) on a proximal end side of the medical device in respective units of the medical device.

Additionally, an axis refers to a central axis in a longitudinal direction of a medical device body.

The longitudinal section of the medical device refers to a section obtained by cutting the medical device along the axis.

The cross-section of the medical device refers to a cross-section obtained by cutting the medical device in a plane orthogonal to the axis.

Embodiment 1-1

First, Embodiment 1-1 will be described with reference to FIGS. 1 to 8(b).

Figure 1:
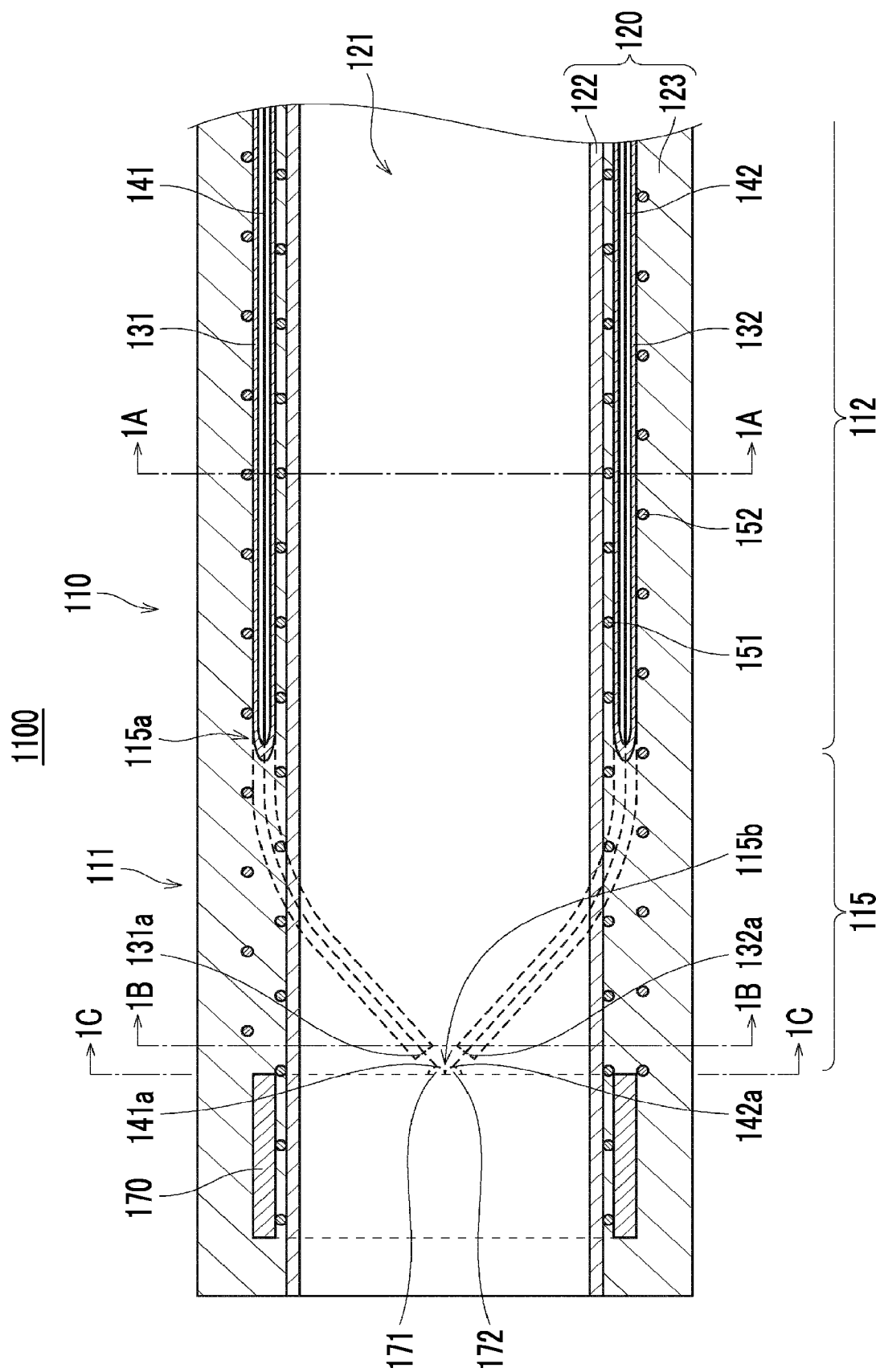
FIG. 1 is a longitudinal sectional view illustrating a portion on a distal end side in a medical device body of a medical device related to Embodiment 1-1.
Figure 2:
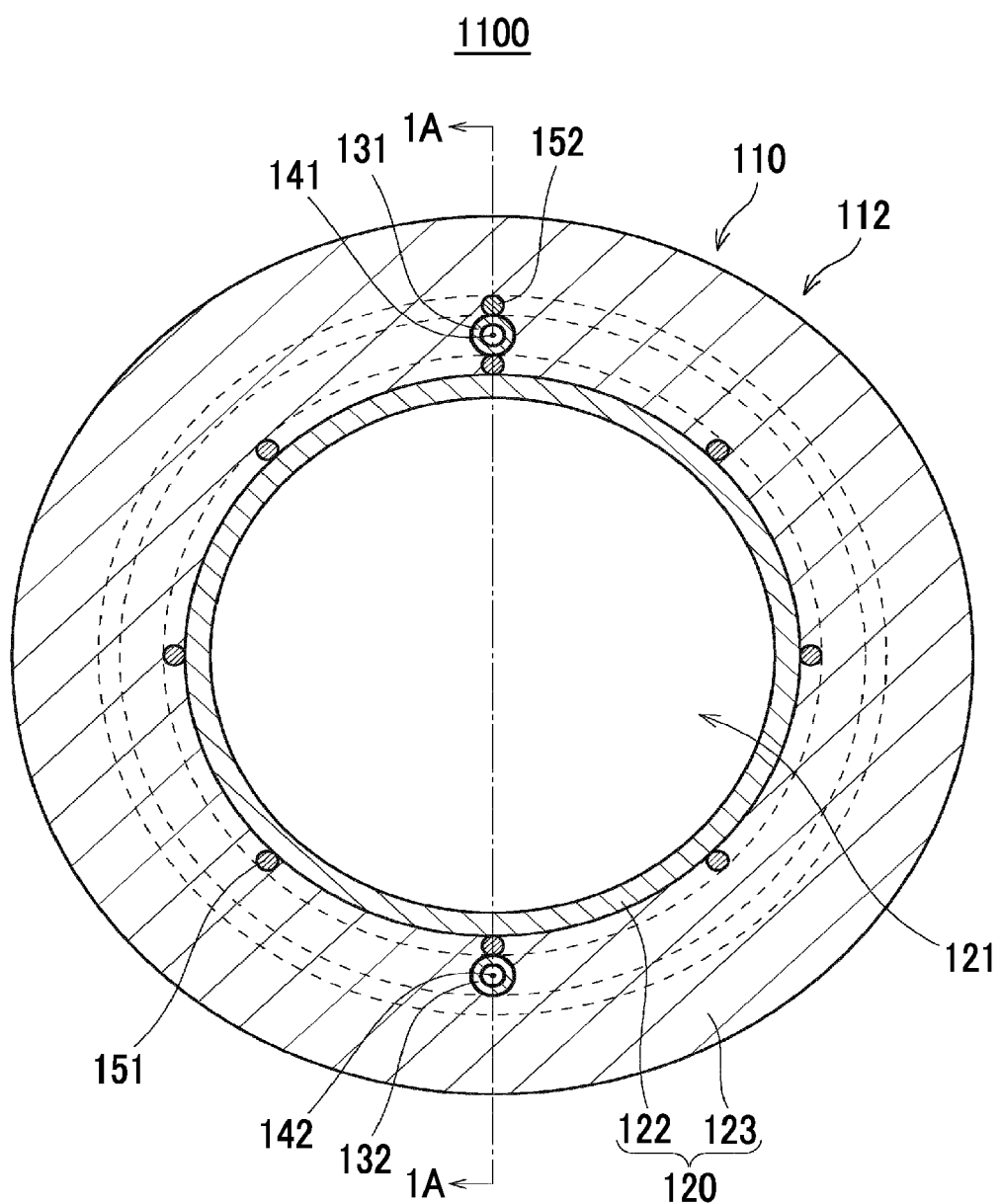
FIG. 2 is a cross-sectional view of the medical device body along line 1A-1A of FIG. 1.

FIG. 1 is a sectional view along line 1A-1A of FIG. 2.

Figure 4:
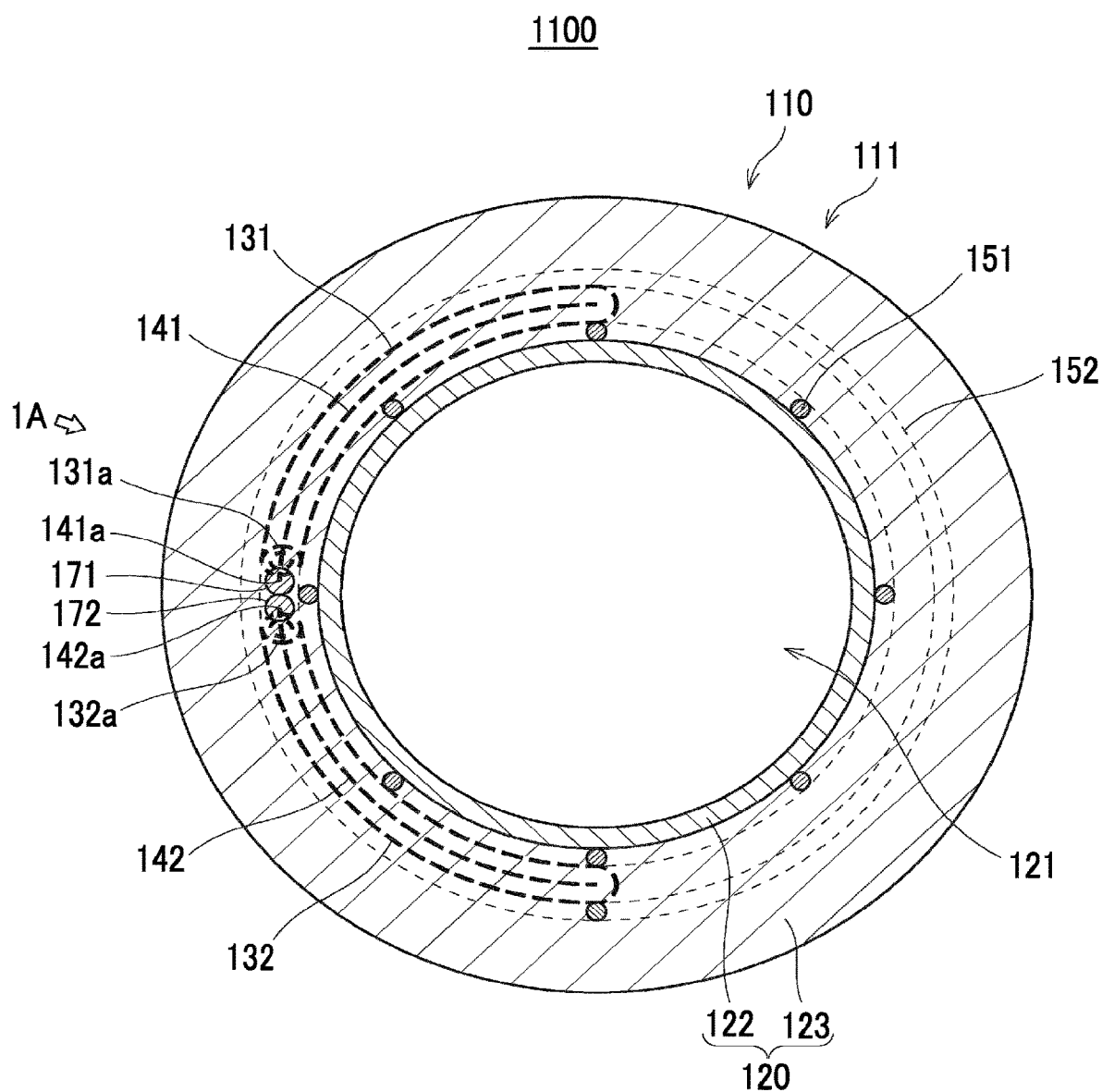
FIG. 4 is a cross-sectional view of the medical device body along line 1C-1C of FIG. 1.
Figure 5:
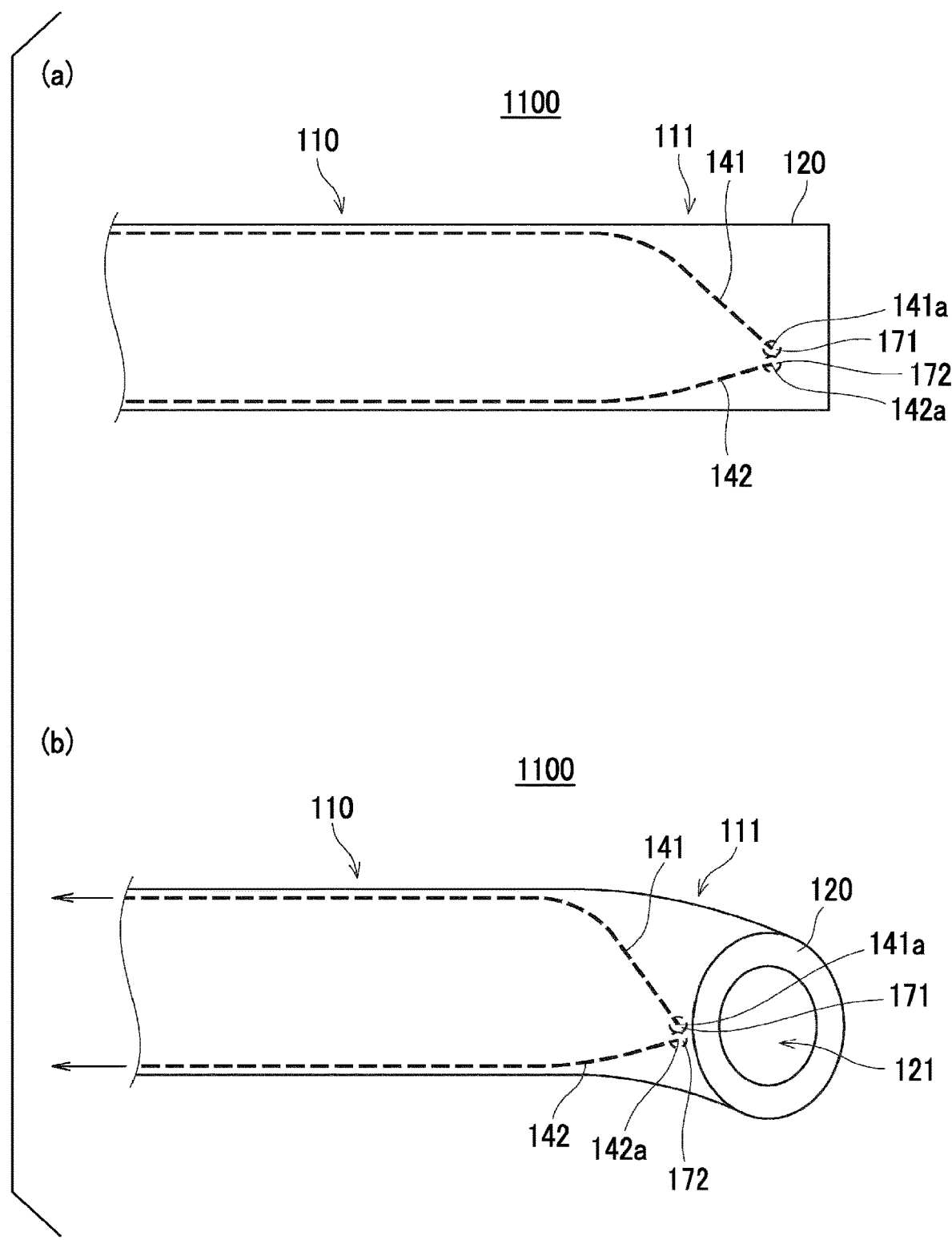
FIGS. 5(*a*) and 5(*b*) are schematic views for illustrating the bending motion of a distal end part of the medical device body of the medical device related to Embodiment 1-1.

FIGS. 5(a) and 5(b) are schematic views for illustrating a bending motion when a distal end part 111 of a medical device body 110 is seen in a direction of arrow 1A of FIG. 4, FIG. 5(a) illustrates a state before the bending, and FIG. 5(b) illustrates a bent state.

Figure 7:
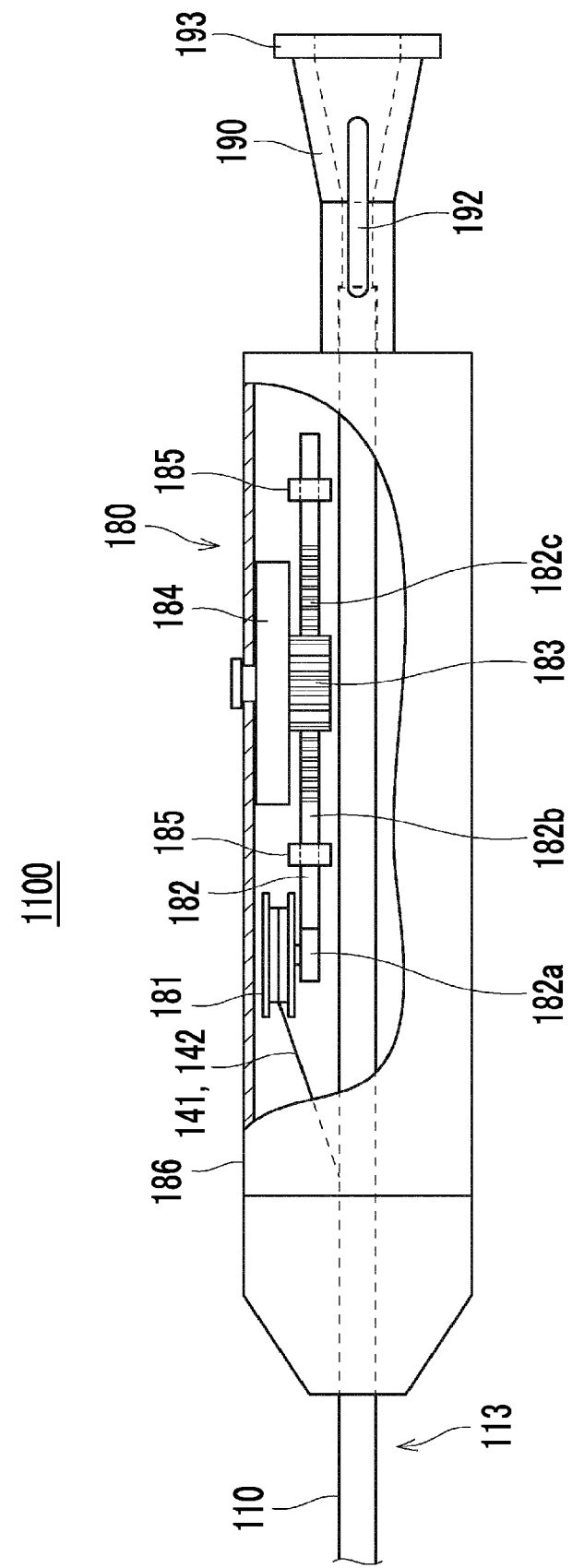
FIG. 7 is a side view illustrating the bending operating part and the portion in the vicinity thereof in the medical device related to Embodiment 1-1.
Figure 8:
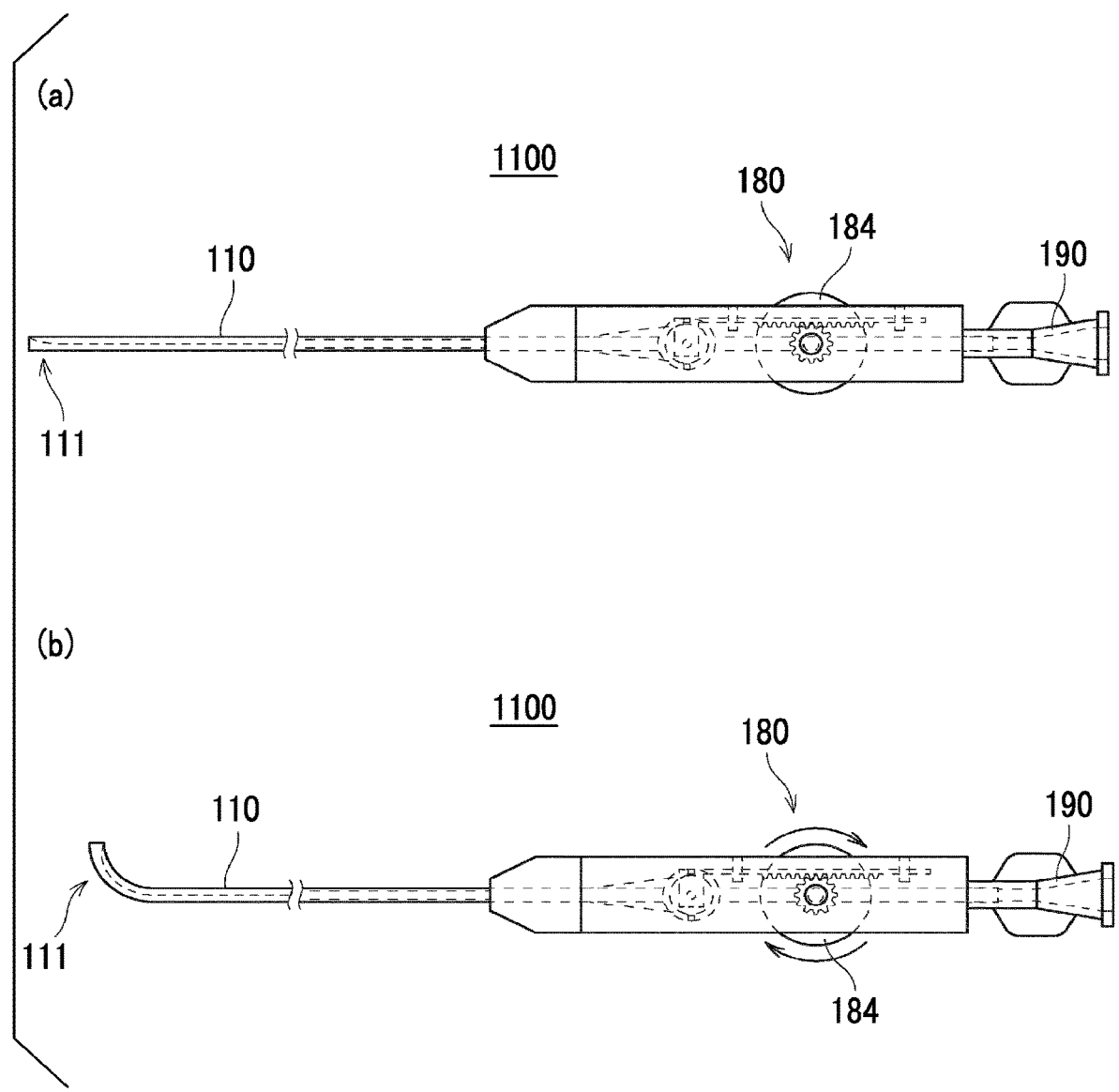
FIG. 8(*a*) is an overall view of the medical device related to Embodiment 1-1, and FIG. 8(*b*) is an overall view illustrating a state where the distal end part of the medical device body of the medical device related to Embodiment 1-1 is bent to one side.
Figure 9:
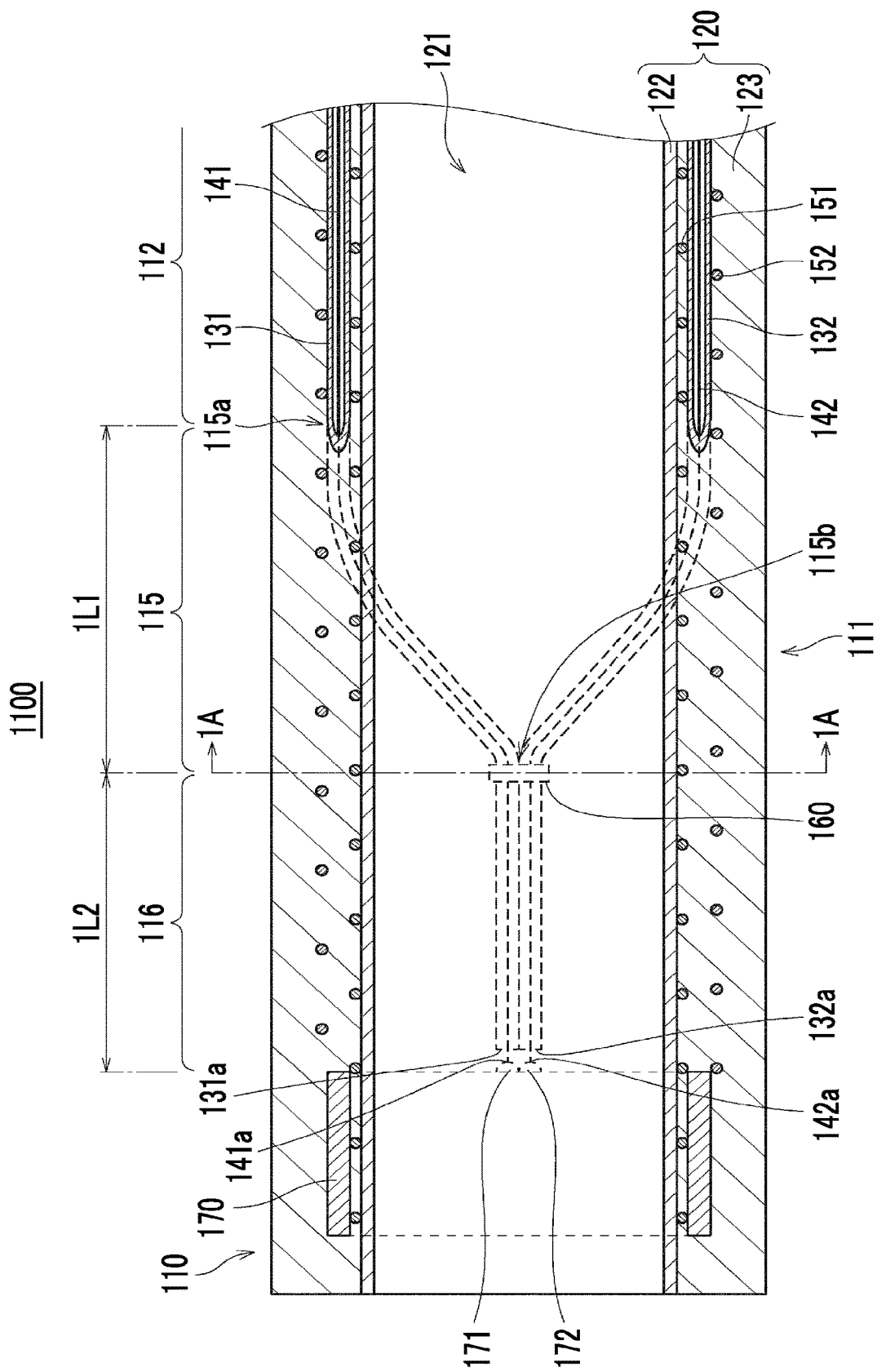
FIG. 9 is a longitudinal sectional view illustrating a portion on a distal end side in a medical device body of a medical device related to Embodiment 1-2.

In FIG. 7, a housing 186 of a bending operating part 180 is broken partially to illustrate the internal structure of the housing 186.

In FIGS. 8(a) and 8(b), a middle portion of the medical device body 110 in the longitudinal direction is broken and omitted.

In the medical device body 110 illustrated in FIGS. 8(a) and 8(b), a portion closer to the proximal end side than the omitted portion and a portion closer to the distal end side than the omitted portion have rotational phases around the axis of the medical device body 110 that are different from each other by 90 degrees.

As illustrated in any of FIGS. 1 to 8(b), a medical device 1100 related to the present embodiment includes the elongated medical device body 110, a first operating line 141 and a second operating line 142 that are inserted in an axial direction of the medical device body 110, and the bending operating part 180 (FIG. 6, FIG. 7) for performing the bending operation of the distal end part 111 of the medical device body 110 by pulling the first operating line 141 and the second operating line 142.

At an intermediate part 112 and a proximal end part 113 (FIG. 6, FIG. 7) in the axial direction of the medical device body 110, the first operating line 141 and the second operating line 142 extend in parallel so as to be spaced apart from each other in a circumferential direction of the medical device body 110.

At the distal end part 111 in the axial direction of the medical device body 110, the first operating line 141 and the second operating line 142 are gradually curved so as to approach each other in the circumferential direction of the medical device body 110 toward the distal end side and joined together.

Here, the fact that the first operating line 141 and the second operating line 142 are close to each other means that a distal end 141a of the first operating line 141 and a distal end 142a of the second operating line 142 are joined together. It is preferable that the distal end 141a of the first operating line 141 and the distal end 142a of the second operating line 142 are close to each other at a distance smaller than the thickness of a resin tube 120 to be described below.

According to the present embodiment, the distal end part 111 of the medical device body 110 can be bent as illustrated in FIGS. 5(a) and 5(b) by pulling both of the first operating line 141 and the second operating line 142. In this case, the load of pulling the distal end part 111 of the medical device body 110 with the first operating line 141 and the load of pulling the distal end part 111 with the second operating line 142 can be balanced with each other. Therefore, the occurrence of a phenomenon in which the medical device body 110 rotates around the axis such that the first operating line 141 or the second operating line 142 tends to take a shortcut can be suppressed.

Thus, even when the distal end part 111 is further bent after the medical device body 110 passes through a body cavity, such as a curved blood vessel, it is possible to more reliably bend the distal end part 111 in a desired direction.

As in the case of the present embodiment, in a case where the number of operating lines provided in the medical device 1100 is two, and these operating lines are joined together, a direction in which the distal end part 111 can be bent by pulling the operating lines is one direction.

The medical device 1100 is, typically, a catheter.

The medical device body 110 includes the resin tube 120 of which an inner cavity is a lumen 121.

In the case of the present embodiment, the resin tube 120 has a layer structure including a hollow tubular inner layer 122 of which the inner cavity is the lumen 121, and a hollow tubular outer layer 123 that is formed coaxially with the inner layer 122 and at an outer periphery of the inner layer 122. The inner layer 122 and the outer layer 123 are respectively made of resin materials. An inner peripheral surface of the outer layer 123 is joined to an outer peripheral surface of the inner layer 122.

The resin material constituting the inner layer 122 and the resin material constituting the outer layer 123 may be different from each other, or may be the same as each other.

A hydrophilic coat may be formed on an outer surface layer of the medical device body 110 as necessary.

The lumen 121 is continuously formed from a distal end of the medical device body 110 to a proximal end thereof, and opens at each of the distal end and the proximal end of the medical device body 110.

The medical device body 110 further includes a first hollow tube 131 and a second hollow tube 132 that are buried in the resin tube 120. The first operating line 141 is inserted through the first hollow tube 131, and the second operating line 142 is inserted through the second hollow tube 132.

The first hollow tube 131 and the second hollow tube 132 are respectively sublumen tubes, and inner cavities of these sublumen tubes are sublumens. That is, the operating lines (the first operating line 141, the second operating line 142) are respectively inserted through the sublumens.

The internal diameters of the first hollow tube 131 and the second hollow tube 132 are smaller than the internal diameter of the lumen 121.

The first operating line 141 and the second operating line 142 are respectively constituted of thin lines, such as metal or resin.

In addition, in the case of the present embodiment, the first hollow tube 131 and the second hollow tube 132 are disposed avoiding a position on an in-course side when the distal end part 111 of the medical device body 110 is bent. Therefore, the bending of the distal end part 111 can be easily performed. Since the first hollow tube 131 and the second hollow tube 132 are spaced apart from the in-course side, particularly on a further proximal end side in the distal end part 111, the bending becomes easy.

At the distal end part 111 of the medical device body 110, the first hollow tube 131 and the second hollow tube 132 are gradually curved so as to approach each other in the circumferential direction of the medical device body 110 toward the distal end side. Accordingly, the first operating line 141 within the first hollow tube 131 and the second operating line 142 within the second hollow tube 132 are gradually curved so as to approach each other in the circumferential direction of the medical device body 110 toward the distal end side.

The first hollow tube 131 and the second hollow tube 132 do not intersect each other. Additionally, the first operating line 141 and the second operating line 142 do not intersect each other.

In this way, the medical device body 110 is configured to include the resin tube 120 having the lumen 121, and the first hollow tube 131 and the second hollow tube 132 that are buried in the resin tube 120 and allows the first operating line 141 and the second operating line 142 to be respectively inserted therethrough. At the distal end part 111 of the medical device body 110 in the axial direction, the first hollow tube 131 and the second hollow tube 132 are gradually curved so as to approach each other in the circumferential direction of the medical device body 110 toward the distal end side.

A region where the first operating line 141 and the second operating line 142 are gradually curved so as to approach each other in the circumferential direction of the medical device body 110 toward the distal end side in the axial direction of the medical device body 110 is referred to as a curved region 115. A proximal end position 115a of the curved region 115 is a position where the first operating line 141 and the second operating line 142 starts to be curved toward each other, and a distal end position 115b of the curved region 115 is a position where the first operating line 141 and the second operating line 142 finishes being curved toward each other.

In the case of the present embodiment, the distal end position 115b of the curved region 115 is a position where the distal ends 141a and 142a of the first operating line 141 and the second operating line 142 are disposed, or a position in the vicinity thereof.

The distal end 141a of the first operating line 141 protrudes from a distal end 131a of the first hollow tube 131. Similarly, the distal end 142a of the second operating line 142 protrudes from a distal end 132a of the second hollow tube 132.

For example, the distal end 141a is located in the vicinity of the distal end 131a, and the distal end 142a is located in the vicinity of the distal end 132a.

The medical device body 110 includes, for example, a braid layer 151 buried in the resin tube 120. Accordingly, the medical device body 110 is reinforced by the braid layer 151. The braid layer 151 is configured by braiding two or more wires. The braid layer 151 is disposed, for example, around the inner layer 122.

The first hollow tube 131 and the second hollow tube 132 are disposed, for example, on a further radially outer side (at a position far from an axis of the medical device body 110) of the medical device body 110 than the braid layer 151.

The medical device body 110 further includes a winding wire 152 buried in the resin tube 120. The winding wire 152 is wound on a further radially outer side of the medical device body 110 than the braid layer 151, the first hollow tube 131, and the second hollow tube 132. For example, the winding wire 152 constrains the first hollow tube 131 and the second hollow tube 132 with respect to the braid layer 151.

Figure 3:
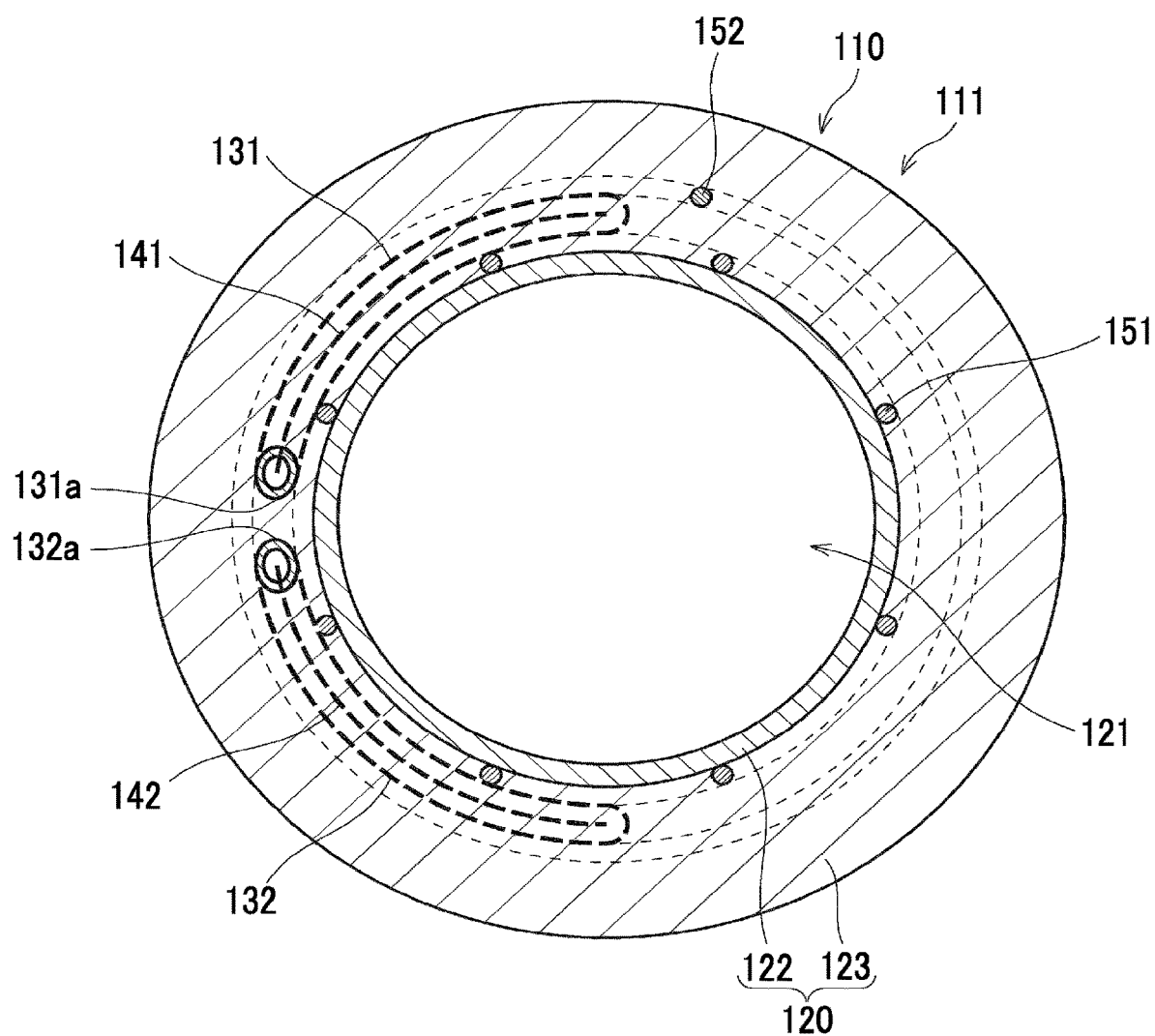
FIG. 3 is a cross-sectional view of the medical device body along line 1B-1B of FIG. 1.

In the curved region 115, each of the first hollow tube 131 and the second hollow tube 132 is disposed along an outer periphery of the braid layer 151 (refer to FIGS. 3 and 4).

In the curved region 115, the distance between the first hollow tube 131 and the second hollow tube 132 in the circumferential direction of the medical device body 110 decreases gradually toward the distal end side, and the distance between the first operating line 141 and the second operating line 142 in the circumferential direction of the medical device body 110 decreases gradually toward the distal end side.

The first hollow tube 131 and the second hollow tube 132 are deformed in a curved shape, for example, on a further distal end side than the proximal end position 115a of the curved region 115. The first hollow tube 131 and the second hollow tube 132 may be fixed to at least one of the braid layer 151 or the inner layer 122 at the proximal end position 115a of the curved region 115, or a distal end of the winding wire 152 may be disposed at the proximal end position 115a of the curved region 115, and the first hollow tube 131 and the second hollow tube 132 may not be constrained by the winding wire 152 on a further distal end side than the proximal end position 115a.

At the intermediate part 112 and the proximal end part 113 in the axial direction of the medical device body 110, the first operating line 141 and the second operating line 142 are disposed at positions that face each other in the circumferential direction of the medical device body 110.

In the case of the present embodiment, for example, as illustrated in FIG. 2, at the intermediate part 112 of the medical device body 110, the first operating line 141 and the second operating line 142 face each other by 180 degrees in the circumferential direction of the medical device body 110 with the axis of the medical device body 110 as a reference. Similarly, even at the proximal end part 113 of the medical device body 110 and the proximal end position 115a of the curved region 115, the first operating line 141 and the second operating line 142 face each other by 180 degrees in the circumferential direction of the medical device body 110. That is, at the intermediate part 112, the proximal end part 113, and the proximal end position 115a of the curved region 115, the phase difference between the first operating line 141 and the second operating line 142 in the circumferential direction of the medical device body 110 is 180 degrees.

The phase difference between the first operating line 141 and the second operating line 142 in the circumferential direction of the medical device body 110 decreases gradually toward the distal end side in the curved region 115, and at the distal end position 115b of the curved region 115, for example, the phase difference is about 0. In the case of the present embodiment, the first operating line 141 and the second operating line 142 are rotated by 90 degrees in the circumferential direction of the medical device body 110 in the curved region 115.

However, the fact that the first operating line 141 and the second operating line 142 disposed at positions that face each other in the circumferential direction of the medical device body 110 is not limited to this example, and means that the first operating line 141 and the second operating line 142 are spaced apart from each other by 120 degrees or more in the circumferential direction of the medical device body 110.

Additionally, in the case of the present embodiment, at the intermediate part 112, the proximal end part 113, and the proximal end position 115a of the curved region 115 in the medical device body 110, the first hollow tube 131 and the second hollow tube 132 face each other by 180 degrees in the circumferential direction of the medical device body 110 with the axis of the medical device body 110 as a reference. That is, at the intermediate part 112, the proximal end part 113, and the proximal end position 115a of the curved region 115, the phase difference between the first hollow tube 131 and the second hollow tube 132 in the circumferential direction of the medical device body 110 is 180 degrees. The phase difference decreases gradually toward the distal end side in the curved region 115.

The distal end part 111 of the medical device body 110 is provided with a ring-shaped marker 170 made of a radiopaque metallic material.

The marker 170 is disposed coaxially with the lumen 121 and around the lumen 121.

The marker 170 is disposed, for example, around the braid layer 151.

The distal end 141a of the first operating line 141 is fixed to the marker 170 by a first fixing part 171 that is, for example, spot-shaped solder.

Similarly, the distal end 142a of the second operating line 142 is fixed to the marker 170 by the second fixing part 172 that is, for example, spot-shaped solder.

The first fixing part 171 and the second fixing part 172 are disposed, for example, at an end part of the marker 170 on the proximal end side.

In the case of the present embodiment, the distal end 141a of the first operating line 141 and the distal end 142a of the second operating line 142 are coupled to each other. That is, the distal ends of the first operating line 141 and the second operating line 142 are coupled to each other.

More specifically, the first fixing part 171 and the second fixing part 172 are adjacent to and in contact with each other. That is, the first fixing part 171 and the second fixing part 172 are integrated with each other.

The distal end 141a and the distal end 142a may be fixed to the marker 170 by a single fixing part.

Next, a hub 190 provided at the proximal end part of the medical device body 110 will be described with reference to FIGS. 6 and 7.

The hub 190 has a coupling part 193 for inserting an injector (syringe), which is not illustrated, from a proximal end of the hub 190. A thread groove is formed at an outer periphery of the coupling part 193 so that the syringe can be detachably fixed.

Two wing parts 192, which face each other via an axis of the hub 190, are provided at an outer periphery of the hub 190.

The proximal end part of the medical device body 110 is inserted into and fixed to a distal end part of the hub 190. Accordingly, the lumen 121 inside the medical device body 110 and an internal space of the hub 190 communicate with each other.

By rotating the wing parts 192 about the axis of the hub 190, a torque operation for rotating the entire medical device body 110 about an axis is possible.

The housing 186 of the bending operating part 180 to be described below is connected and fixed to a distal end side of the hub 190.

Next, the bending operating part 180 provided in the medical device 1100 will be described with reference to FIGS. 6 and 7.

The medical device 1100 includes the bending operating part 180 for performing the bending operation of the distal end part 111 of the medical device body 110 by pulling the first operating line 141 and the second operating line 142.

The bending operating part 180 is configured to include a rotating member 181 that is rotatably supported and is engaged with the first operating line 141 and the second operating line 142 and to which a proximal end part of the first operating line 141 and a proximal end part of the second operating line 142 are fixed, and a moving mechanism that moves the rotating member 181 in a pulling direction in which the first operating line 141 and the second operating line 142 are pulled, and an opposite direction opposite to the pulling direction.

The rotating member 181 is, for example, a pulley.

The moving mechanism is configured to include a forward/backward movable member 182 and a pinion 183.

The forward/backward movable member 182 includes a holding part 182a that rotatably holds the rotating member 181, and a rod-shaped part 182b that extends from the holding part 182a to the proximal end side of the medical device body 110.

A rack part 182c is formed in the rod-shaped part 182b.

The bending operating part 180 further includes a housing 186 that is a body part of the bending operating part 180, a dial operating part 184 rotatably supported to the housing 186, a pinion 183 provided integrally with the dial operating part 184, and a guide 185 (for example, a pair of front and rear guides 185) that is provided on an inner surface of the housing 186 to guide the rod-shaped part 182b in a longitudinal direction of the rod-shaped part 182b.

The proximal end part 113 of the medical device body 110 is guided to a proximal end side of the housing 186 through the inside of the housing 186, and is inserted into and fixed to the distal end part of the hub 190.

A rotating shaft of the dial operating part 184 extends in a direction orthogonal to an axis direction of the medical device body 110 within the housing 186.

The pinion 183 is formed integrally with the dial operating part 184 on one face side of the dial operating part 184, and is disposed coaxially with a rotational axis of the dial operating part 184.

A gear at an outer periphery of the pinion 183 meshes with a gear of the rack part 182c of the forward/backward movable member 182.

At least a portion of the dial operating part 184 is exposed to the outside of the housing 186 so that an operation in which an operator who performs the operation of the medical device 1100 rotates the dial operating part 184 can be performed from the outside of the housing 186.

The first operating line 141 and the second operating line 142 are delivered from the medical device body 110 within the housing 186.

Figure 6:
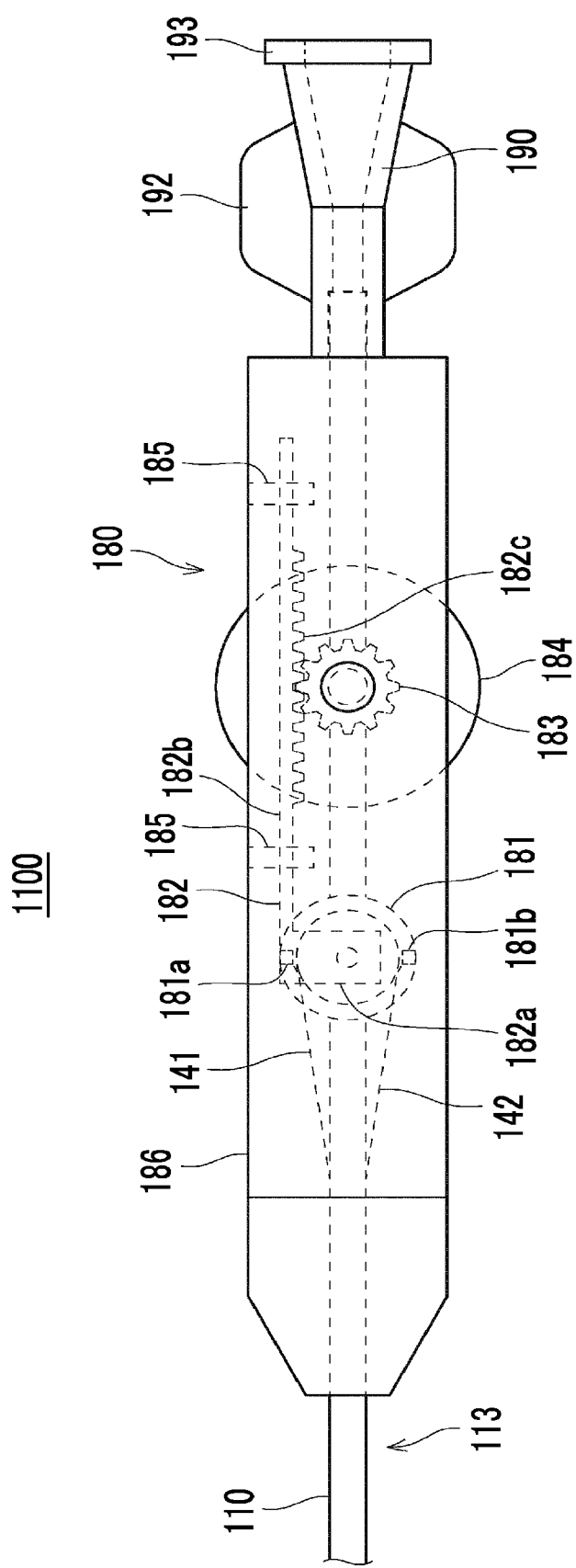
FIG. 6 is a plan view illustrating a bending operating part and a portion in the vicinity thereof in the medical device related to Embodiment 1-1.

The proximal end part of the first operating line 141 is wound around the rotating member 181, for example, by one and a half turns, and a proximal end of the first operating line 141 is fixed to the rotating member 181 by the first fixing part 181a (FIG. 6).

Similarly, the second operating line 142 is wound around the rotating member 181, for example, by one and a half turns, and a proximal end of the second operating line 142 is fixed to the rotating member 181 by a second fixing part 181b (FIG. 6).

A winding direction of the first operating line 141 and a winding direction of the second operating line 142 around the rotating member 181 are mutually opposite directions. For this reason, the rotational angle of the rotating member 181 is autonomously adjusted to an angle at which the tension of the first operating line 141 and the tension of the second operating line 142 are balanced with each other.

As the operator who performs the operation of the medical device 1100 grips the housing 186 or the hub 190 to rotate the dial operating part 184, the pinion 183 integral with the dial operating part 184 rotates about an axis. Along with this, the forward/backward movable member 182 having the rack part 182c moves forward (moves to the distal end side of the medical device body 110) or moves backward (moves to the proximal end side of the medical device body 110) in the axial direction of the medical device body 110 relative to the housing 186.

In FIG. 6, by rotating the dial operating part 184 in the clockwise direction, the forward/backward movable member 182 and the rotating member 181 moves backward, and both of the first operating line 141 and the second operating line 142 are pulled to the proximal end side of the medical device body 110.

In this way, the first operating line 141 and the second operating line 142 are pulled at a time by the operation on the bending operating part 180.

Here, "the first operating line 141 and the second operating line 142 are pulled at a time" means that a timing when both of the first operating line 141 and the second operating line 142 are pulled is present, and is not limited to timings when pulling is started by the first operating line 141 and the second operating line 142 being the same, and is not limited to timings when pulling is ended by the first operating line 141 and the second operating line 142 being the same.

For example, as illustrated in FIG. 8(a), when the distal end part 111 of the medical device body 110 has a linear shape, both of the first operating line 141 and the second operating line 142 are pulled to the proximal end side of the medical device body 110 if the dial operating part 184 is rotated in the clockwise direction in FIG. 8(b). Therefore, the distal end part 111 of the medical device body 110 is bent in one direction.

If the dial operating part 184 is rotated in the counterclockwise direction from the state of FIG. 8(b), the forward/backward movable member 182 and the rotating member 181 move forward, and the tension of the first operating line 141 and the second operating line 142 are released. Therefore, the distal end part 111 of the medical device body 110 is allowed to return linearly.

In this way, in the case of the present embodiment, the bending operating part 180 is configured to receive an operation performed by a user with the rotating mechanism (dial operating part 184) and convert a force applied to the rotating mechanism by this operation into a forward/backward movement in the axial direction of the medical device body 110 with a conversion mechanism constituted of the pinion 183 and the rack (rack part 182c).

Next, examples of the materials of the respective units of the medical device 1100 will be described.

As the materials of the inner layer 122, for example, resin materials, such as polytetrafluoroethylene (PTFE), polyvinylidene fluoride (PVDF), and perfluoroalkoxy fluororesin (PFA), can be used.

As the materials of the outer layer 123, in addition to polyimide (PI), polyamide imide (PAI), and polyethylene terephthalate (PET), resin materials, such as polyethylene (PE), polyamide (PA), nylon elastomer, polyurethane (PU), ethylene-vinyl acetate resin (EVA), polyvinyl chloride (PVC), or polypropylene (PP), can be used.

As the materials of the first hollow tube 131 and the second hollow tube 132, for example, resin materials, such as polytetrafluoroethylene (PTFE), polyvinylidene fluoride (PVDF), and perfluoroalkoxy fluororesin (PFA), can be used.

Although metallic materials, such as stainless steel and tungsten, are preferable as the materials of the wire that constitutes the braid layer 151, the materials of the wire may be, for example, resin materials.

Although the metallic materials, such as stainless steel and tungsten, are preferable as the materials of the wire that constitutes the winding wire 152, the materials of the wire may be, for example, resin materials.

According to the medical device 1100 related to Embodiment 1-1 as described above, the distal end part 111 of the medical device body 110 can be bent by pulling both of the first operating line 141 and the second operating line 142. In that case, the load for pulling the distal end part 111 of the medical device body 110 with the first operating line 141, and the load for pulling the distal end part 111 with the second operating line 142 can be balanced with each other. Therefore, the occurrence of the phenomenon in which the medical device body 110 rotates around the axis such that the first operating line 141 or the second operating line 142 tends to take a shortcut can be suppressed.

Therefore, it is possible to more reliably bend the distal end part 111 of the medical device body 110 in a desired direction.

Embodiment 1-2

Next, the medical device 1100 related to Embodiment 1-2 will be described with reference to FIGS. 9 to 11(b).

Figure 10:
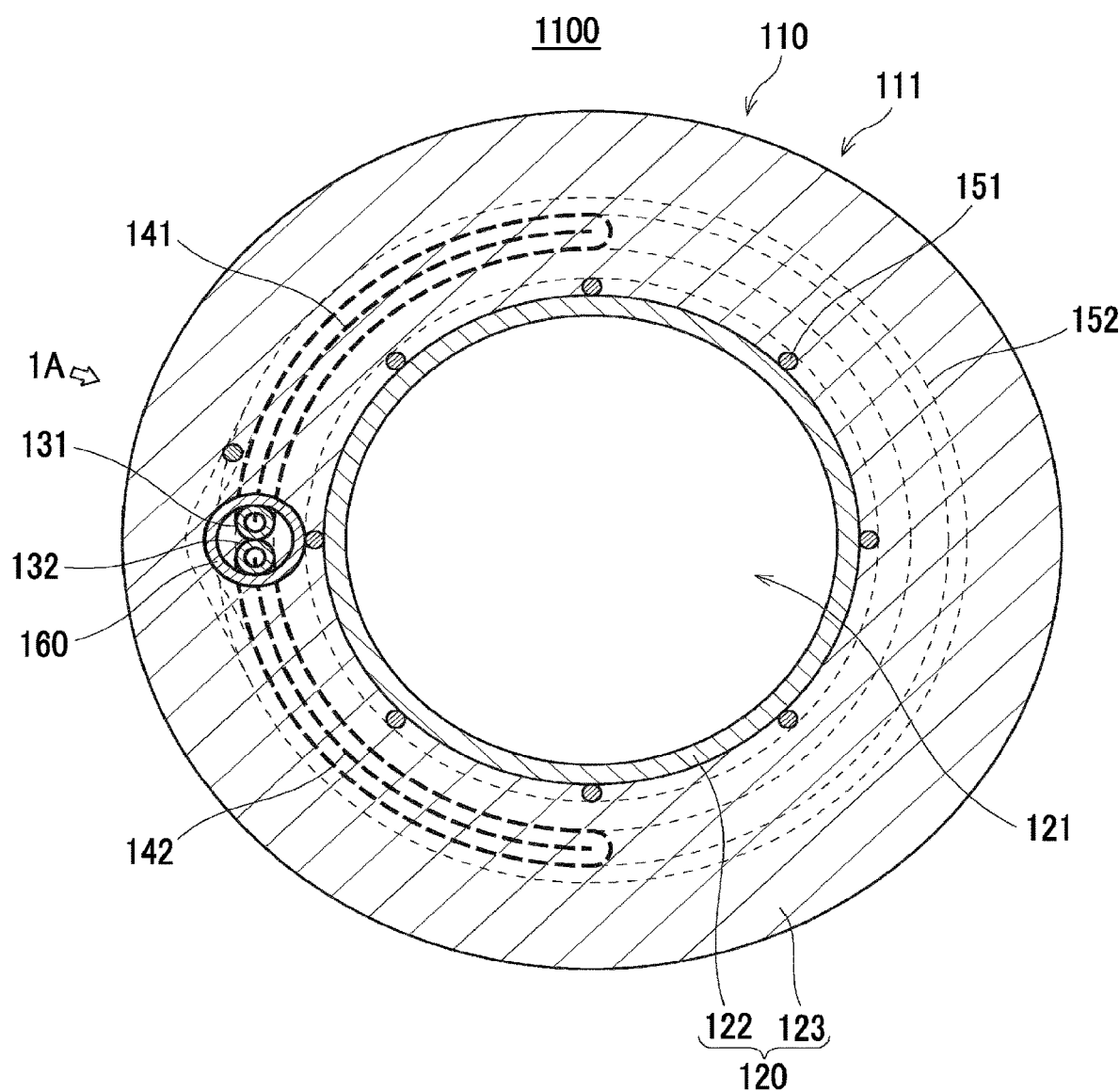
FIG. 10 is a cross-sectional view of the medical device body along line 1A-1A of FIG. 9.
Figure 11:
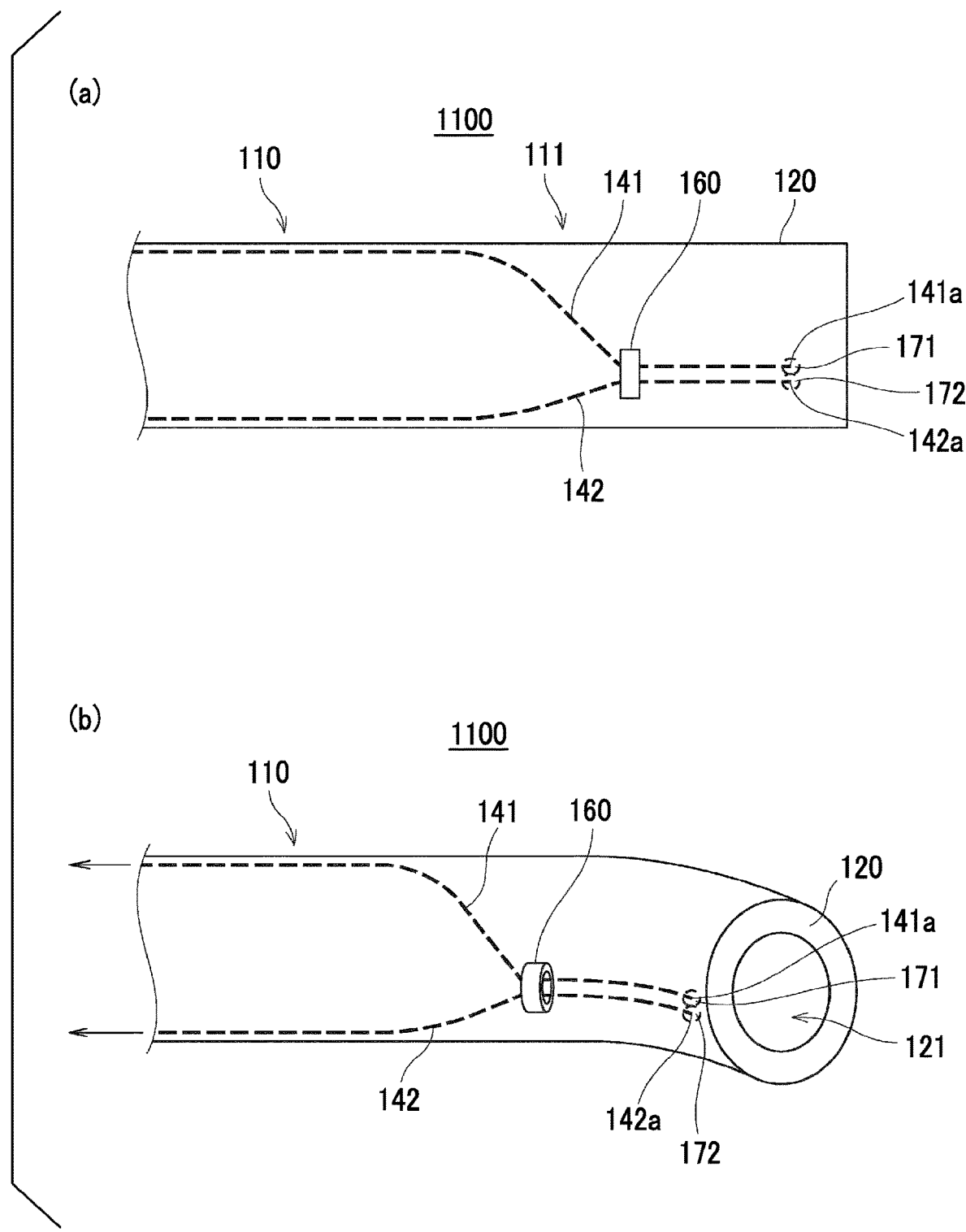
FIGS. 11(*a*) and 11(*b*) are schematic views for illustrating the bending motion of a distal end part of the medical device body of the medical device related to Embodiment 1-2.
Figure 12:
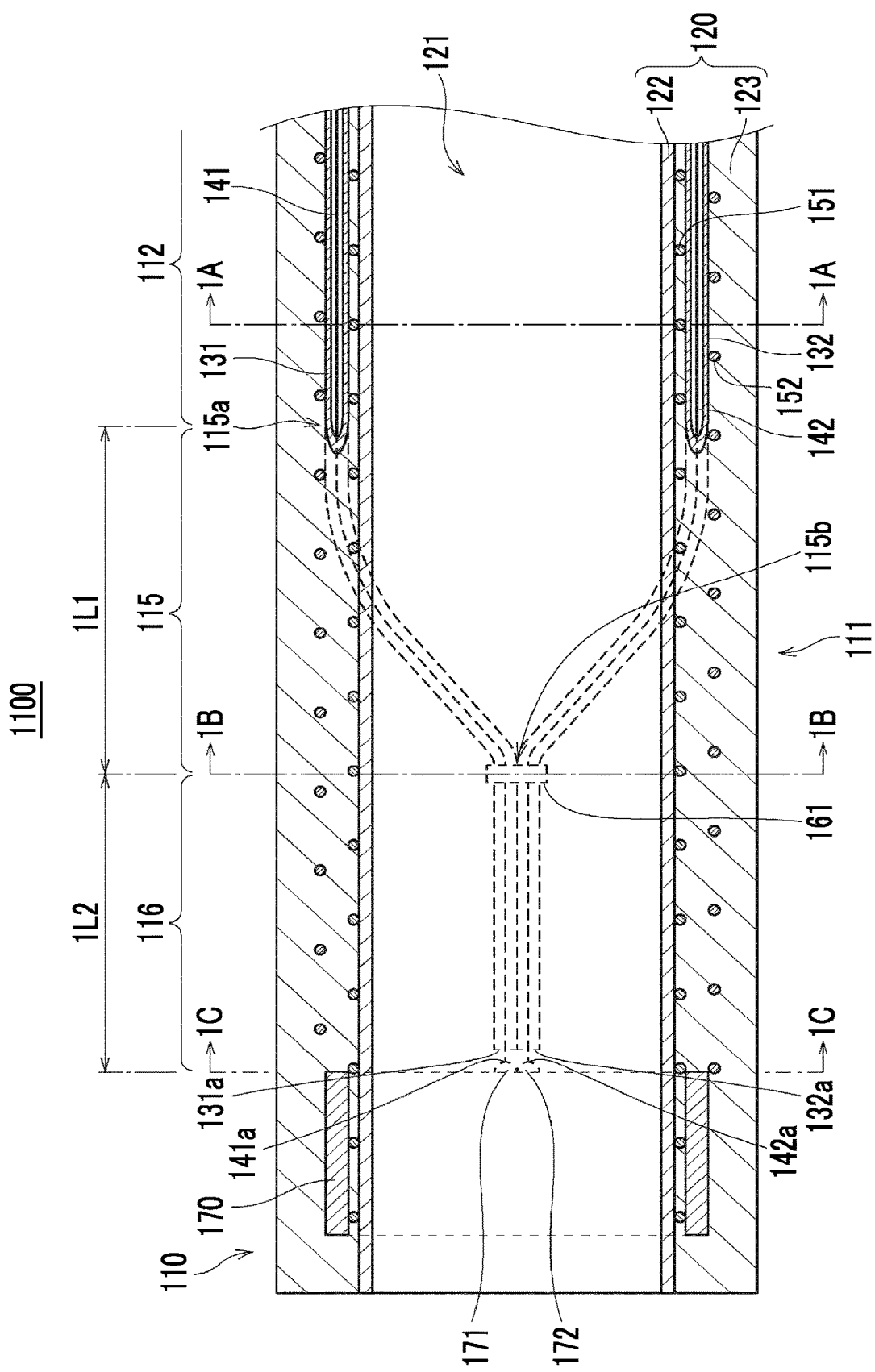
FIG. 12 is a longitudinal sectional view illustrating a portion on a distal end side in a medical device body of a medical device related to Embodiment 1-3.

FIGS. 11(a) and 11(b) are schematic views for illustrating the bending motion when the distal end part 111 of the medical device body 110 is seen in the direction of arrow 1A of FIG. 10, FIG. 11(a) illustrates the state before the bending, and FIG. 11(b) illustrates the bent state.

The medical device 1100 related to the present embodiment is different from the medical device 1100 related to the above Embodiment 1-1 in terms of points to be described below, and is configured similarly to the medical device 1100 related to the above Embodiment 1-1 in terms of the other points.

In the case of the present embodiment, a parallel region 116 where the first operating line 141 and the second operating line 142 extend in parallel close to each other is formed between a distal end (distal end position 115b) of the curved region 115, and the distal ends 141a and 142a of the first operating line 141 and the second operating line 142.

That is, the medical device body 110 is configured to include the resin tube 120 having the lumen 121, the first operating line 141 and the second operating line 142 are inserted around the lumen 121 of the resin tube 120, the first operating line 141 and the second operating line 142 are close to each other at a distance smaller than the thickness of the resin tube 120, at the distal end (distal end position 115b) of the curved region 115 where the first operating line 141 and the second operating line 142 are gradually curved so as to approach each other in the circumferential direction of the medical device body 110 toward the distal end side, and the parallel region 116 where the first operating line 141 and the second operating line 142 extend in parallel close to each other is formed between the distal end (distal end position 115b) of the curved region 115, and the distal ends 141a and 142a of the first operating line 141 and the second operating line 142.

In the parallel region 116, the first hollow tube 131 and the second hollow tube 132 extend in parallel in abutment with or close to each other.

More specifically, in the case of the present embodiment, the medical device 1100 further includes an annular member 160 buried in the resin tube 120 at a distal end part of the curved region 115.

The annular member 160 is configured to have a rigidity higher than the resin tube 120, and have an external diameter smaller than the thickness of the resin tube 120 (refer to FIG. 10).

The first operating line 141 and the second operating line 142 are inserted through the annular member 160.

Accordingly, fluctuations of paths of the first operating line 141 and the second operating line 142 can be more reliably suppressed.

More specifically, in the case of the present embodiment, the first hollow tube 131 and the second hollow tube 132 are inserted through the annular member 160.

That is, the medical device body 110 is configured to include the first hollow tube 131 and the second hollow tube 132 that are buried in the resin tube 120 and allow the first operating line 141 and the second operating line 142 to be respectively inserted therethrough, the first hollow tube 131 and the second hollow tube 132 are inserted through the annular member 160, and in the curved region 115, the first hollow tube 131 and the second hollow tube 132 are gradually curved so as to approach each other in the circumferential direction of the medical device body 110 toward the distal end side.

Although the materials of the annular member 160 are not particularly limited, the annular member 160 can be made of, for example, metal or hard resin.

Even in the case of the present embodiment, by pulling both of the first operating line 141 and the second operating line 142, the distal end part 111 of the medical device body 110 can be bent as illustrated in FIGS. 11(a) and 11(b).

In this case, the bending angle in the parallel region 116 becomes steeper than the bending angle in the curved region 115.

As an example, the distance (a distance 1L2 illustrated in FIG. 9) from the distal end (distal end position 115b) of the curved region 115 to the distal ends 141a and 142a of the first operating line 141 and the second operating line 142 is longer than the distance (a distance 1L1 illustrated in FIG. 9) from the proximal end (proximal end position 115a) of the curved region 115 to the distal end (distal end position 115b) thereof in the axial direction of the medical device body 110.

By virtue of such a configuration, the distal end part 111 can be more easily bent.

Additionally, the bending of the distal end part 111 can be caused mainly in the parallel region 116. For this reason, the friction between the first operating line 141 and the first hollow tube 131 in the curved region 115 and the friction between the second operating line 142 and the second hollow tube 132 can be substantially uniformly maintained irrespective of the bending angle of the distal end part 111. Therefore, the magnitude of a force required for pulling the first operating line 141 and the second operating line 142 can be substantially uniformly maintained irrespective of the bending angle of the distal end part 111.

Additionally, as another example, the distance (distance 1L1 illustrated in FIG. 9) from the proximal end (proximal end position 115a) of the curved region 115 to the distal end (distal end position 115b) thereof is longer than the distance (distance 1L2 illustrated in FIG. 9) from the distal end (distal end position 115b) of the curved region 115 to the distal ends 141a and 142a of the first operating line 141 and the second operating line 142 in the axial direction of the medical device body 110.

By virtue of such a configuration, the flexibility of the distal end part 111 can be suppressed to some extent.

Additionally, the curving of the first operating line 141, the second operating line 142, the first hollow tube 131, and the second hollow tube 132 in the curved region 115 can be made gentle. Therefore, the friction between the first operating line 141 and the first hollow tube 131 in the curved region 115 and the friction between the second operating line 142 and the second hollow tube 132 can be reduced.

Additionally, a length region where the first hollow tube 131 and the second hollow tube 132 translate close to each other in the distal end part 111 of the medical device body 110, that is, a length region with high rigidity becomes short. Therefore, excellent selectivity (excellent blood vessel selectivity or the like) when the distal end part 111 of the medical device body 110 is bent and is made to enter a branched body cavity can be obtained.

The distance 1L1 and the distance 1L2 may be the same. In this case, the smoothness of the pulling of the first operating line 141 and the second operating line 142 and the excellent selectivity when the distal end part 111 of the medical device body 110 is bent and is made to enter a branched body cavity can be obtained in a well-balanced manner.

Embodiment 1-3

Next, the medical device 1100 related to Embodiment 1-3 will be described with reference to FIGS. 12 to 18(c).

Figure 15:
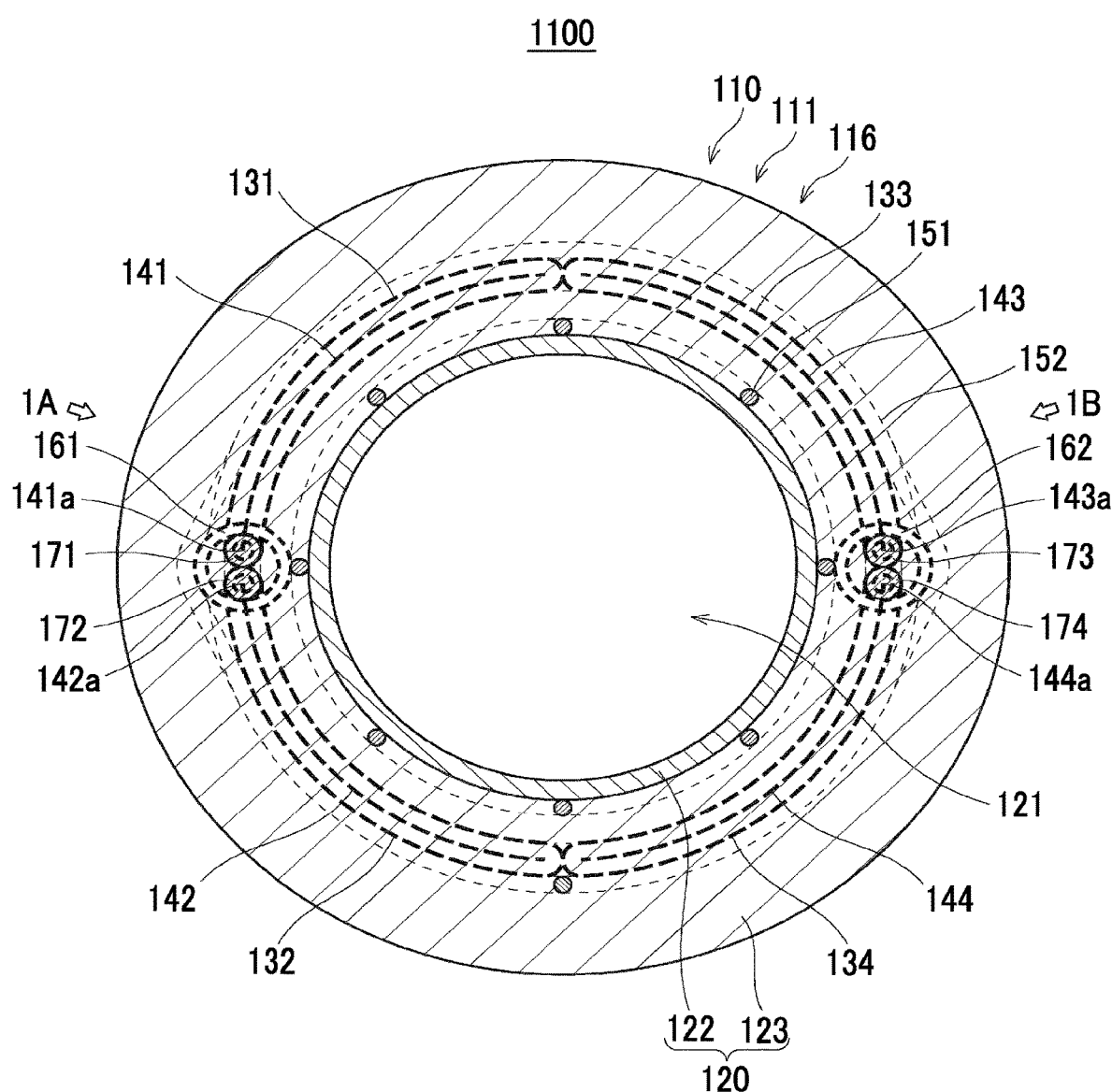
FIG. 15 is a cross-sectional view of the medical device body along line 1C-1C of FIG. 12.
Figure 16:
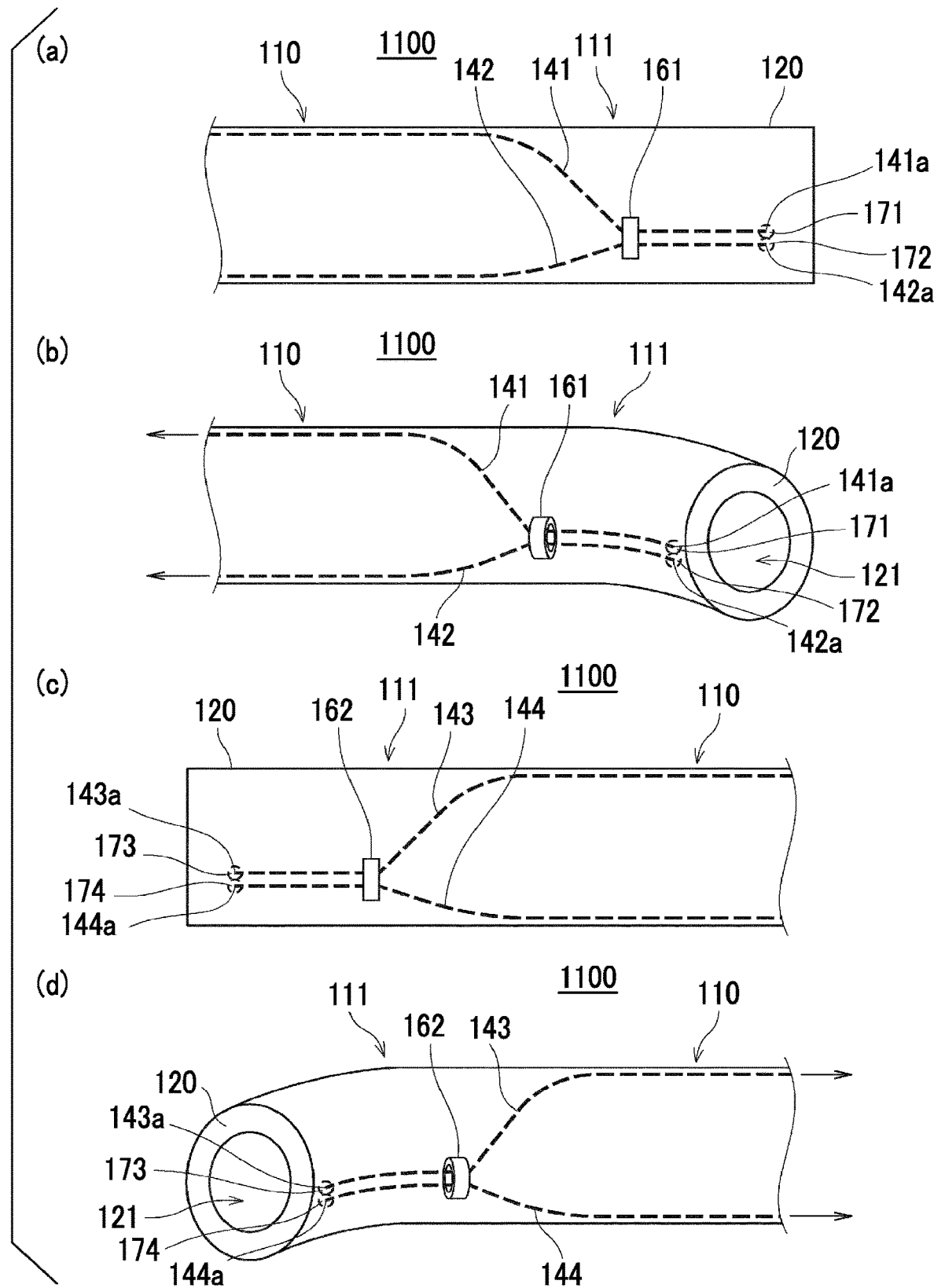
FIGS. 16(*a*), 16(*b*), 16(*c*), and 16(*d*) are schematic views for illustrating the bending motion of a distal end part of the medical device body of the medical device related to Embodiment 1-3.

FIGS. 16(a) and 16(b) are schematic views for illustrating the bending motion when the distal end part 111 of the medical device body 110 is seen in the direction of arrow 1A of FIG. 15, FIG. 16(a) illustrates the state before the bending, and FIG. 16(b) illustrates the bent state.

FIGS. 16(c) and 16(d) are schematic views for illustrating the bending motion when the distal end part 111 of the medical device body 110 is seen in the direction of arrow 1B of FIG. 15, FIG. 16(c) illustrates the state before the bending, and FIG. 16(d) illustrates the bent state.

In FIGS. 18(a), 18(b), and 18(c), the middle portion of the medical device body 110 in the longitudinal direction is broken and omitted. In the medical device body 110 illustrated in FIGS. 18(a), 18(b), and 18(c), a portion closer to the proximal end side than the omitted portion and a portion closer to the distal end side than the omitted portion have rotational phases around the axis of the medical device body 110 that are different from each other by 90 degrees.

The medical device 1100 related to the present embodiment is different from the medical device 1100 related to the above Embodiment 1-2 in terms of points to be described below, and is configured similarly to the medical device 1100 related to the above Embodiment 1-2 in terms of the other points.

The medical device 1100 related to the present embodiment includes a third operating line 143 and a fourth operating line 144 that are inserted in the axial direction of the medical device body 110. The third operating line 143 and the fourth operating line 144 are respectively constituted of thin lines, such as metal or resin, similarly to the first operating line 141 and the second operating line 142.

The medical device body 110 further includes a third hollow tube 133 and a fourth hollow tube 134 that are buried in the resin tube 120. The third operating line 143 is inserted through the third hollow tube 133, and the fourth operating line 144 is inserted through the fourth hollow tube 134.

The third hollow tube 133 and the fourth hollow tube 134 are respectively the same sublumen tubes as the first hollow tube 131 and the second hollow tube 132, and inner cavities of these sublumen tubes are sublumens. That is, the operating lines (the third operating line 143, the fourth operating line 144) are respectively inserted through the sublumens.

The internal diameters of the third hollow tube 133 and the fourth hollow tube 134 are smaller than the internal diameter of the lumen 121.

Figure 13:
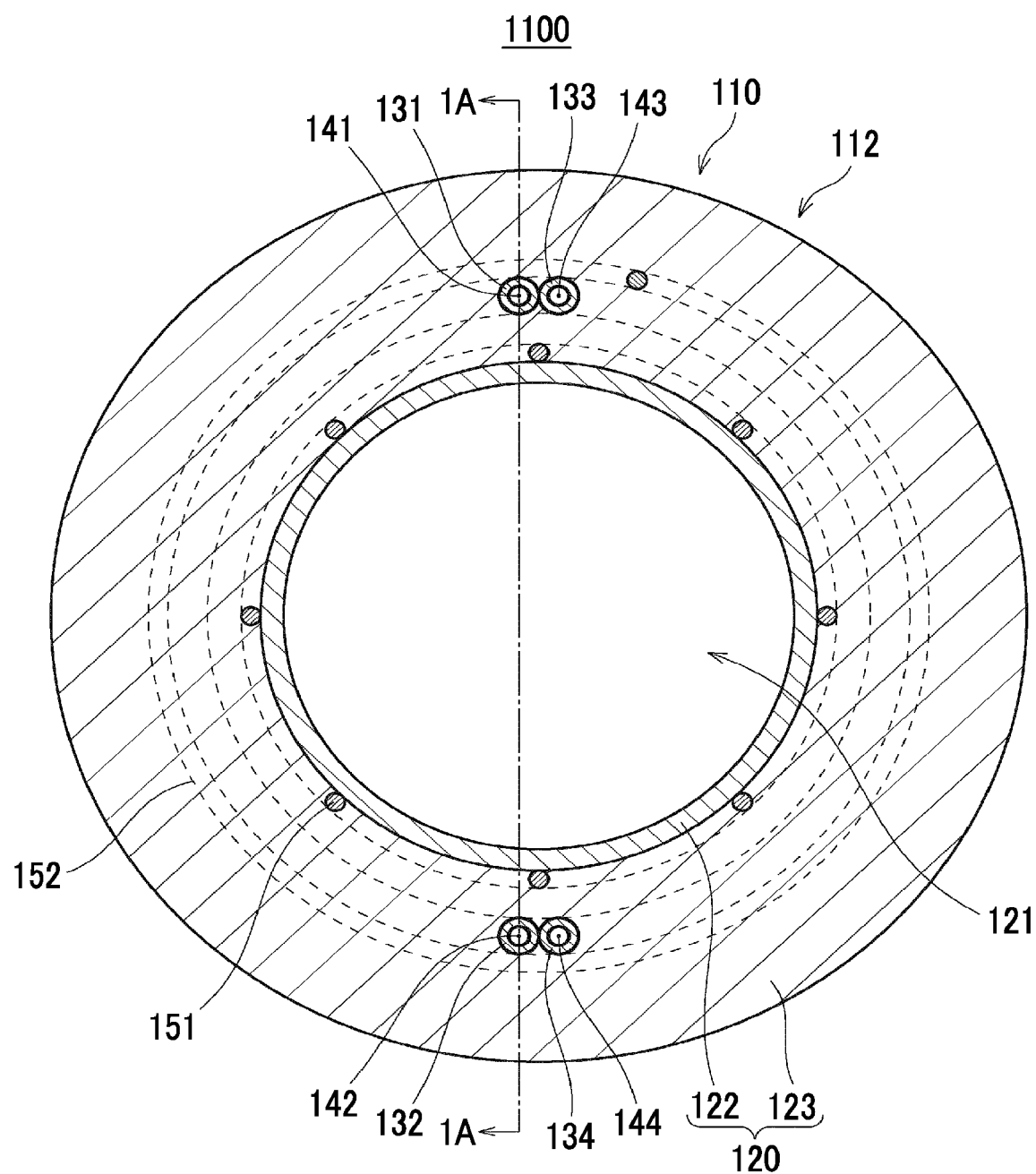
FIG. 13 is a cross-sectional view of the medical device body along line 1A-1A of FIG. 12.

In the case of the present embodiment, at the intermediate part 112 of the medical device body 110, the first hollow tube 131 and the third hollow tube 133 extend in parallel in abutment with or close to each other, and the second hollow tube 132 and the fourth hollow tube 134 extend in parallel in abutment with or close to each other (refer to FIG. 13).

Similarly, even at the proximal end part of the medical device body 110, the first hollow tube 131 and the third hollow tube 133 extend in parallel in abutment with or close to each other, and the second hollow tube 132 and the fourth hollow tube 134 extend in parallel in abutment with or close to each other.

In the curved region 115 of the distal end part 111 of the medical device body 110, the third hollow tube 133 and the fourth hollow tube 134 are gradually curved so as to approach each other in the circumferential direction of the medical device body 110 toward the distal end side. Accordingly, the third operating line 143 within the third hollow tube 133 and the fourth operating line 144 within the fourth hollow tube 134 are gradually curved so as to approach each other in the circumferential direction of the medical device body 110 toward the distal end side.

The direction in which the third hollow tube 133 and the third operating line 143 are curved in the curved region 115 is a direction symmetrical to the direction in which the first hollow tube 131 and the first operating line 141 are curved.

Similarly, the direction in which the fourth hollow tube 134 and the fourth operating line 144 are curved in the curved region 115 is a direction symmetrical to the direction in which the second hollow tube 132 and the second operating line 142 are curved.

The respective hollow tubes (the first hollow tube 131, the second hollow tube 132, the third hollow tube 133, and the fourth hollow tube 134) do not intersect other hollow tubes. Additionally, the respective operating lines (the first operating line 141, the second operating line 142, the third operating line 143, and the fourth operating line 144) do not intersect other operating lines.

In the parallel region 116, similarly to the first operating line 141 and the second operating line 142 extending in parallel close to each other, the third operating line 143 and the fourth operating line 144 extend in parallel close to each other.

Additionally, in the parallel region 116, similarly to the first hollow tube 131 and the second hollow tube 132 extending in parallel in abutment with or close to each other, the third hollow tube 133 and the fourth hollow tube 134 extend in parallel in abutment with or close to each other.

A distal end 143a of the third operating line 143 protrudes from a distal end of the third hollow tube 133. Similarly, a distal end 144a of the fourth operating line 144 protrudes from a distal end of the fourth hollow tube 134.

The distal end 143a of the third operating line 143 is fixed to the marker 170 by a third fixing part 173 that is, for example, spot-shaped solder (FIG. 15).

Similarly, the distal end 144a of the fourth operating line 144 is fixed to the marker 170 by a fourth fixing part 174 that is, for example, spot-shaped solder.

The third fixing part 173 and the fourth fixing part 174 are disposed, for example, at the end part of the marker 170 on the proximal end side.

A region where the third fixing part 173 and the fourth fixing part 174 are disposed, and a region where the first fixing part 171 and the second fixing part 172 are disposed to face each other in the circumferential direction of the medical device body 110.

In the case of the present embodiment, the distal end 143a of the third operating line 143 and the distal end 144a of the fourth operating line 144 are coupled to each other. That is, the distal ends of the third operating line 143 and the fourth operating line 144 are coupled to each other.

More specifically, the third fixing part 173 and the fourth fixing part 174 are adjacent to and in contact with each other. That is, the third fixing part 173 and the fourth fixing part 174 are integrated with each other.

The distal end 143a and the distal end 144a may be fixed to the marker 170 by a single fixing part.

Figure 14:
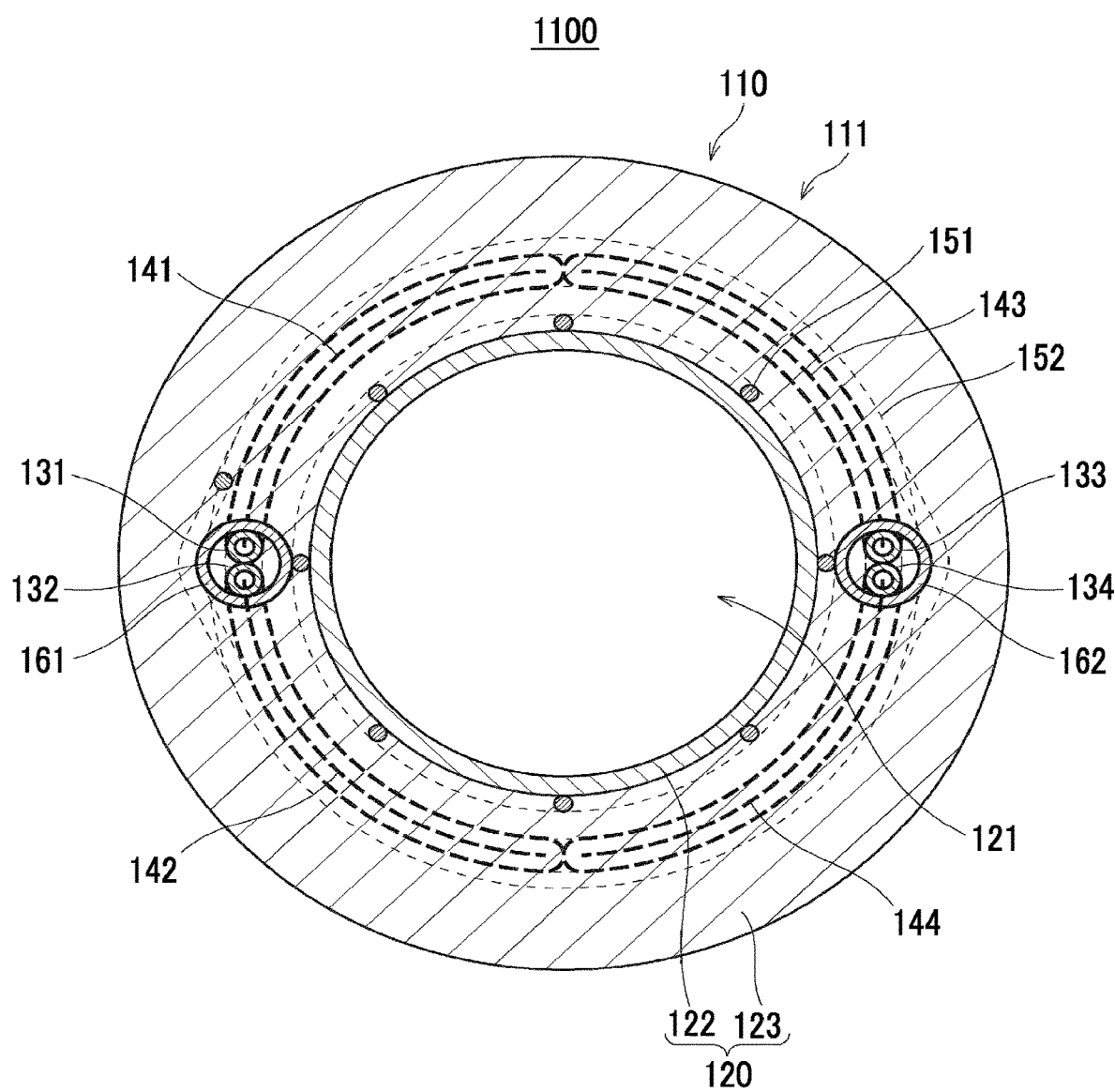
FIG. 14 is a cross-sectional view of the medical device body along line 1B-1B of FIG. 12.

As illustrated in FIG. 14, in the case of the present embodiment, the medical device 1100 includes a first annular member 161 buried in the resin tube 120 at the distal end part of the curved region 115 instead of the annular member 160. The first annular member 161 is the same as the annular member 160 in Embodiment 1-2, and the first hollow tube 131 and the second hollow tube 132 are inserted through the first annular member 161.

Moreover, in the case of the present embodiment, the medical device 1100 includes a second annular member 162 buried in the resin tube 120 at the distal end part of the curved region 115. The second annular member 162 is the same as the first annular member 161. The third hollow tube 133 and the fourth hollow tube 134 are inserted through the second annular member 162.

The first annular member 161 and the second annular member 162 are disposed to face each other in the circumferential direction of the medical device body 110.

Even in the case of the present embodiment, by pulling both of the first operating line 141 and the second operating line 142, the distal end part 111 of the medical device body 110 can be bent in one direction as illustrated in FIGS. 16(a) and 16(b).

Moreover, in the case of the present embodiment, by pulling both of the third operating line 143 and the fourth operating line 144, the distal end part 111 of the medical device body 110 can be bent in an opposite direction opposite to the above one direction as illustrated in FIG. 16(c) and FIG. 16(d).

Figure 17:
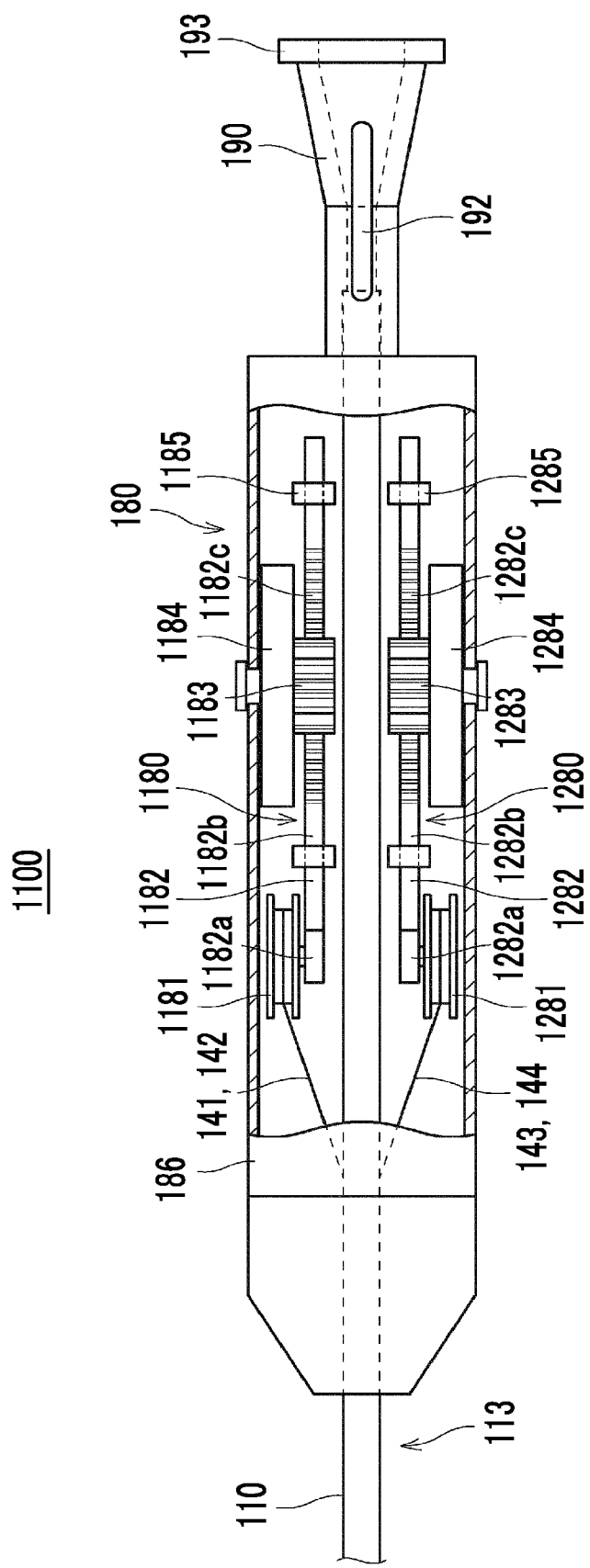
FIG. 17 is a side view illustrating a bending operating part and a portion in the vicinity thereof in the medical device related to Embodiment 1-3.
Figure 18:
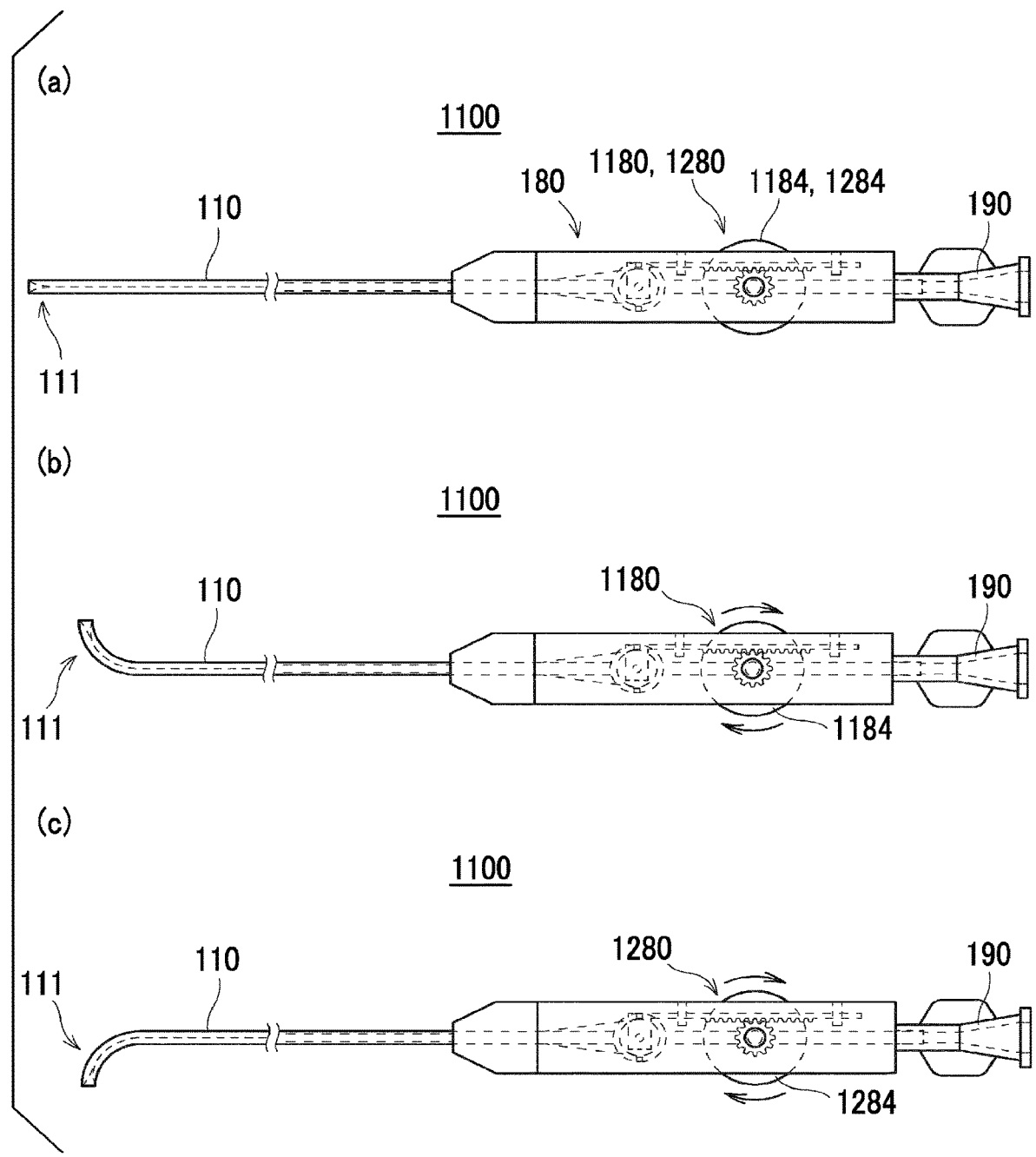
FIG. 18(*a*) is an overall view of the medical device related to Embodiment 1-3, FIG. 18(*b*) is an overall view illustrating a state where the distal end part of the medical device body of the medical device related to Embodiment 1-3 is bent to one side, and FIG. 18(*c*) is an overall view illustrating a state where the distal end part of the medical device body of the medical device related to Embodiment 1-3 is bent to the other side.

As illustrated in FIGS. 17 and 18(a), in the case of the present embodiment, the bending operating part 180 includes a first bending operating part 1180 for performing the bending operation of the distal end part 111 of the medical device body 110 by pulling the first operating line 141 and the second operating line 142, and a second bending operating part 1280 for performing the bending operation of the distal end part 111 of the medical device body 110 by pulling the third operating line 143 and the fourth operating line 144.

The first bending operating part 1180 includes a first rotating member 1181, a first forward/backward movable member 1182, a first pinion 1183, a first dial operating part 1184, and a first guide 1185. The first rotating member 1181, the first forward/backward movable member 1182, the first pinion 1183, the first dial operating part 1184, and the first guide 1185 are respectively equivalent to the rotating member 181, the forward/backward movable member 182, the pinion 183, the dial operating part 184, and the guide 185 that are described in Embodiment 1-1.

Hence, the first forward/backward movable member 1182 includes a first holding part 1182a, a first rod-shaped part 1182b, and a first rack part 1182c that are respectively equivalent to the holding part 182a, the rod-shaped part 182b, and the rack part 182c.

In Embodiment 1-1, similarly to the first operating line 141 and the second operating line 142 being wound around and fixed to the rotating member 181, the first operating line 141 and the second operating line 142 are wound around and fixed to the first rotating member 1181.

The second bending operating part 1280 includes a second rotating member 1281, a second forward/backward movable member 1282, a second pinion 1283, a second dial operating part 1284, and a second guide 1285. The second rotating member 1281, the second forward/backward movable member 1282, the second pinion 1283, the second dial operating part 1284, and the second guide 1285 are the same as the first rotating member 1181, the first forward/backward movable member 1182, the first pinion 1183, the first dial operating part 1184, and the first guide 1185.

The second forward/backward movable member 1282 includes a second holding part 1282a, a second rod-shaped part 1282b, and a second rack part 1282c that are respectively the same as the first holding part 1182a, the first rod-shaped part 1182b, and the first rack part 1182c.

Similarly to the first operating line 141 and the second operating line 142 being wound around and fixed to the first rotating member 1181, the third operating line 143 and the fourth operating line 144 are wound around and fixed to the second rotating member 1281.

For example, the second bending operating part 1280 is disposed vertically symmetrically with respect to the first bending operating part 1180 in FIG. 17.

In the case of the present embodiment, by rotating the first dial operating part 1184 to move the first forward/backward movable member 1182 and the first rotating member 1181 backward, the first operating line 141 and the second operating line 142 can be pulled to bend the distal end part 111 of the medical device body 110 in one direction (FIG. 18(b)).

Additionally, by rotating the second dial operating part 1284 to move the second forward/backward movable member 1282 and the second rotating member 1281, the third operating line 143 and the fourth operating line 144 can be pulled to bend the distal end part 111 of the medical device body 110 in the direction opposite respect to the above one direction (FIG. 18(c)).

In this way, in the case of the present embodiment, the medical device 1100 includes the second bending operating part 1280 for performing the bending operation of the distal end part 111 of the medical device body 110 in a direction different from the direction of the bending of the distal end part 111 of the medical device body 110 by the pulling of the first operating line 141 and the second operating line 142, by pulling the third operating line 143 and the fourth operating line 144.

At the intermediate part 112 and the proximal end part 113 in the axial direction of the medical device body 110, the third operating line 143 and the fourth operating line 144 extend in parallel so as to be spaced apart from each other in the circumferential direction of the medical device body 110. and at the distal end part 111 in the axial direction of the medical device body 110, the third operating line 143 and the fourth operating line 144 are gradually curved so as to approach each other in the circumferential direction of the medical device body 110 toward the distal end side and joined together.

Additionally, the third operating line 143 and the fourth operating line 144 are pulled at a time by the operation on the second bending operating part 1280.

Embodiment 1-4

Next, the medical device 1100 related to Embodiment 1-4 will be described with reference to FIGS. 19(a) and 19(b).

The medical device 1100 related to the present embodiment is different from the medical device 1100 related to the above Embodiment 1-1 in terms of points to be described below, and is configured similarly to the medical device 1100 related to the above Embodiment 1-1 in terms of the other points.

In the case of the present embodiment, an easily bendable part 1110 in which the flexibility of the medical device body 110 is locally high is formed in a region between the first operating line 141 and the second operating line 142 or a region located opposite to the region with respect to the axis of the medical device body 110, in the circumferential direction of the distal end part 111 of the medical device body 110.

Accordingly, since the flexibility of the distal end part 111 is improved, the tension acting on the first operating line 141 and the second operating line 142 during the bending operation can be reduced. Hence, the occurrence of the phenomenon in which the medical device body 110 rotates around the axis such that the first operating line 141 or the second operating line 142 tends to take a shortcut can be suppressed.

Figure 19:
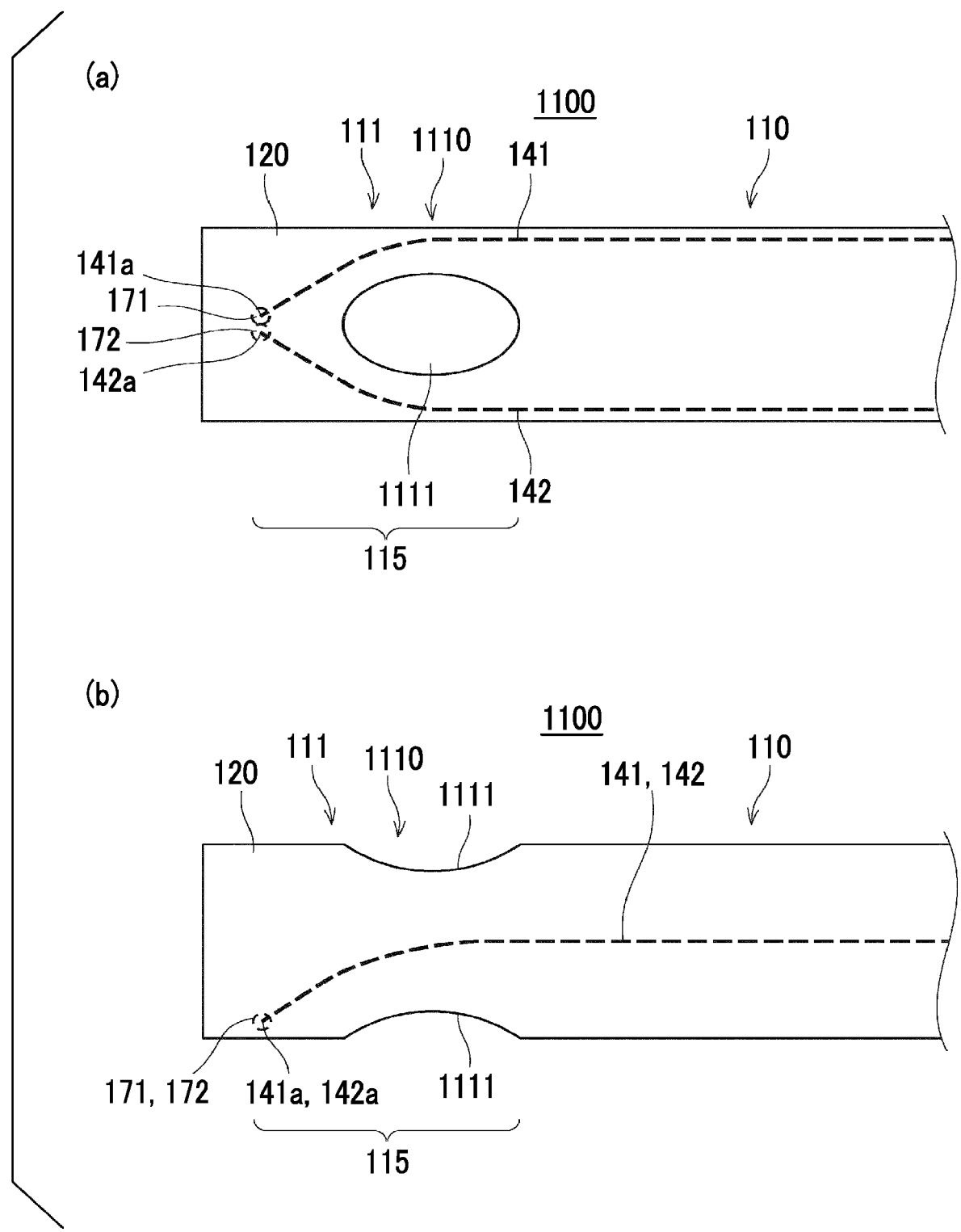
FIGS. 19(*a*) and 19(*b*) are schematic views of a distal end part of a medical device body of a medical device related to Embodiment 1-4, and in these drawings, FIG. 19(*a*) is a plan view, and FIG. 19(*b*) is a side view.

More specifically, as illustrated in FIG. 19(b), the easily bendable parts 1110 are formed both in the region between the first operating line 141 and the second operating line 142 and the region located opposite to the region with respect to the axis of the medical device body 110, in the circumferential direction of the distal end part 111 of the medical device body 110.

Accordingly, the flexibility of the distal end part 111 is further improved.

The easily bendable part 1110 is configured to include a notched part 1111 formed on an outer surface side of the medical device body 110.

The notched part 1111 can be formed in, for example, a shape gouged out in an arc as illustrated in FIG. 19(b). Accordingly, the distal end part 111 can be more steeply bent.

Embodiment 1-5

Next, the medical device 1100 related to Embodiment 1-5 will be described with reference to FIGS. 20(a) and 20(b).

The medical device 1100 related to the present embodiment is different from the medical device 1100 related to the above Embodiment 1-1 in terms of points to be described below, and is configured similarly to the medical device 1100 related to the above Embodiment 1-1 in terms of the other points.

In the case of the present embodiment, the easily bendable part 1110 in which the flexibility of the medical device body 110 is locally high is formed in the region between the first operating line 141 and the second operating line 142 or the region located opposite to the region with respect to the axis of the medical device body 110, in the circumferential direction of the distal end part 111 of the medical device body 110.

Accordingly, since the flexibility of the distal end part 111 is improved, the tension acting on the first operating line 141 and the second operating line 142 during the bending operation can be reduced. Hence, the occurrence of the phenomenon in which the medical device body 110 rotates around the axis such that the first operating line 141 or the second operating line 142 tends to take a shortcut can be suppressed.

Figure 20:
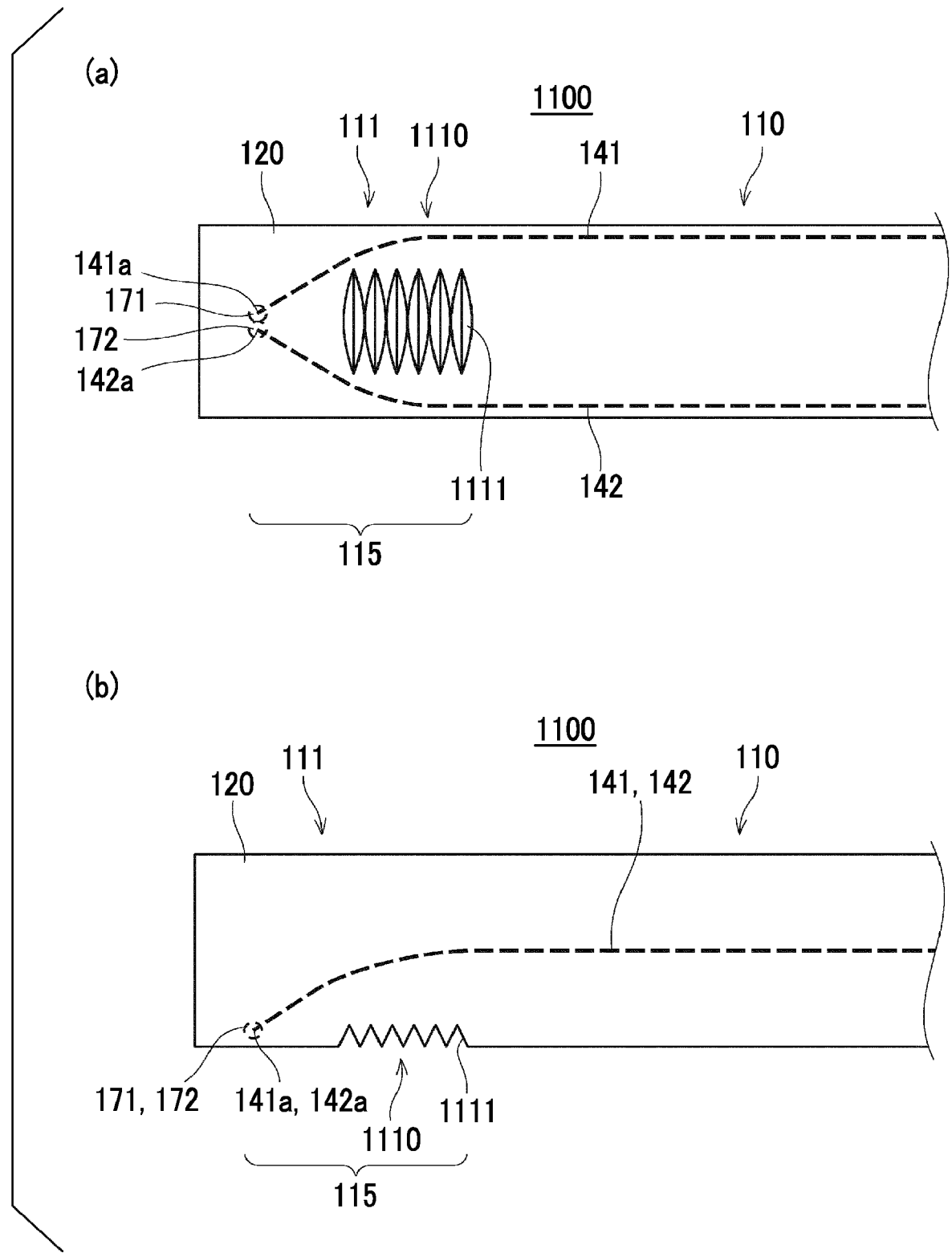
FIGS. 20(*a*) and 20(*b*) are schematic views of a distal end part of a medical device body of a medical device related to Embodiment 1-5, and in these drawings, FIG. 20(*a*) is a plan view, and FIG. 20(*b*) is a side view.

More specifically, as illustrated in FIG. 20(b), the easily bendable part 1110 is formed in the region between the first operating line 141 and the second operating line 142 in the circumferential direction of the distal end part 111 of the medical device body 110, and the easily bendable part 1110 is not formed in the region located opposite to the region with respect to the axis of the medical device body 110.

However, the easily bendable parts 1110 may be formed both in the region between the first operating line 141 and the second operating line 142 and the region located opposite to the region with respect to the axis of the medical device body 110, in the circumferential direction of the distal end part 111 of the medical device body 110.

The easily bendable part 1110 is configured to include the notched part 1111 formed on an outer surface side of the medical device body 110.

In the case of the present embodiment, the medical device body 110 has a plurality of the notched parts 1111 disposed adjacent to each other in the axial direction of the medical device body 110. The notched parts 1111 are elongated in the circumferential direction of the medical device body 110, and the sectional shape thereof is a wedge shape.

In the case of the present embodiment, the distal end part 111 of the medical device body 110 is easily bent in the initial stage of the bending. However, if a certain amount of bending angle is reached, wedge-shaped inclined surfaces come in contact with each other, so that further bending becomes difficult (if a certain amount of bending angle is reached, rigidity becomes high).

For this reason, since the distal end part 111 of the medical device body 110 has excellent deformation resistance against compression in the axial direction when being pushed into a body cavity, the blood vessel selectivity of the medical device 1100 is excellent.

Although the respective embodiments have been described above with reference to the drawings, these are examples of the invention, and various configurations other than the above can also be adopted.

An example in which the rotating mechanism of the bending operating part 180 is the dial operating part 184 has been described in the above Embodiment 1-1. However, the rotating mechanism of the bending operating part 180 may be others (for example, a rotary lever or the like) than the dial operating part 184.

Additionally, an example in which the conversion mechanism of the bending operating part 180 is configured to include the rack (rack part 182c) and the pinion 183 has been described in the above Embodiment 1-1. However, the bending operating part 180 may be configured to include other conversion mechanisms (for example, a cam, a link mechanism, a pin, a guide with a groove, or the like).

The same applies to the other embodiments.

Additionally, an example in which the first operating line 141 and the second operating line 142 are constituted of separate thin lines has been described in the above respective embodiments. However, each of the first operating line 141 and the second operating line 142 may be constituted of a portion of one thin line. That is, the one thin line may be folded at the distal ends 141a and 142a.

Similarly, an example in which the third operating line 143 and the fourth operating line 144 are constituted of separate thin lines has been described above. However, each of the third operating line 143 and the fourth operating line 144 may be constituted of a portion of one thin line. That is, the one thin line may be folded at the distal ends 143a and 144a.

Additionally, although an example in which the proximal end part of the first operating line 141 and the proximal end part of the second operating line 142 are individually fixed to the bending operating part 180 has been described in the above respective embodiments, the proximal end of the first operating line 141 and the proximal end of the second operating line 142 may be are connected to each other, and may be looped (for example, looped in a portion engaged with the rotating member 181) in the bending operating part 180.

Similarly, an example in which a proximal end part of the third operating line 143 and a proximal end part of the fourth operating line 144 are individually fixed to the second bending operating part 1280 has been described above. However, a proximal end of the third operating line 143 and a proximal end of the fourth operating line 144 may be connected to each other, and may be looped (for example, looped in the portion engaged with the second rotating member 1281) in the second bending operating part 1280.

Embodiment 2-1

First, Embodiment 2-1 will be described with reference to FIGS. 21 to 28(h).

Figure 21:
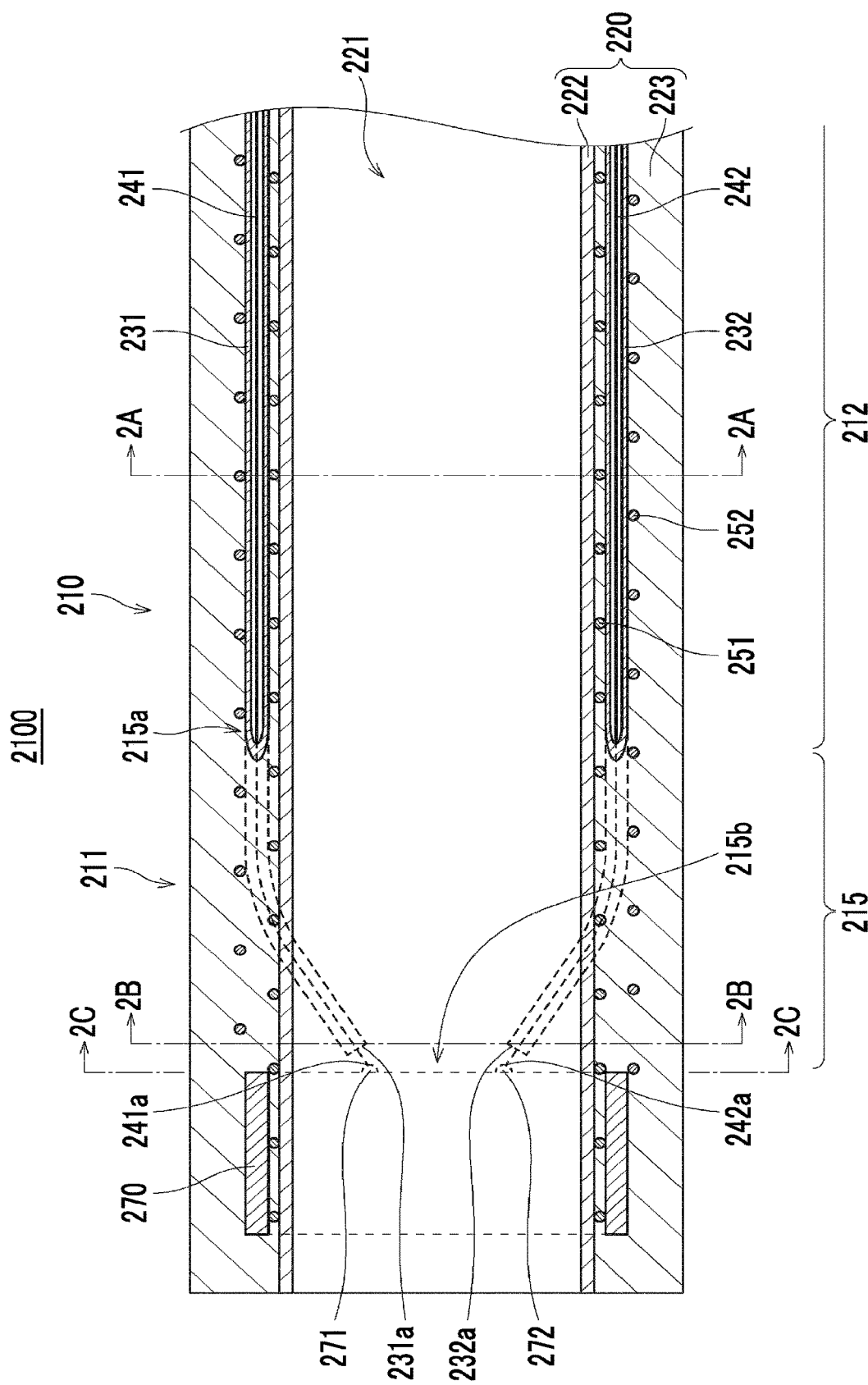
FIG. 21 is a longitudinal sectional view illustrating a portion on a distal end side in a medical device body of a medical device related to Embodiment 2-1.
Figure 22:
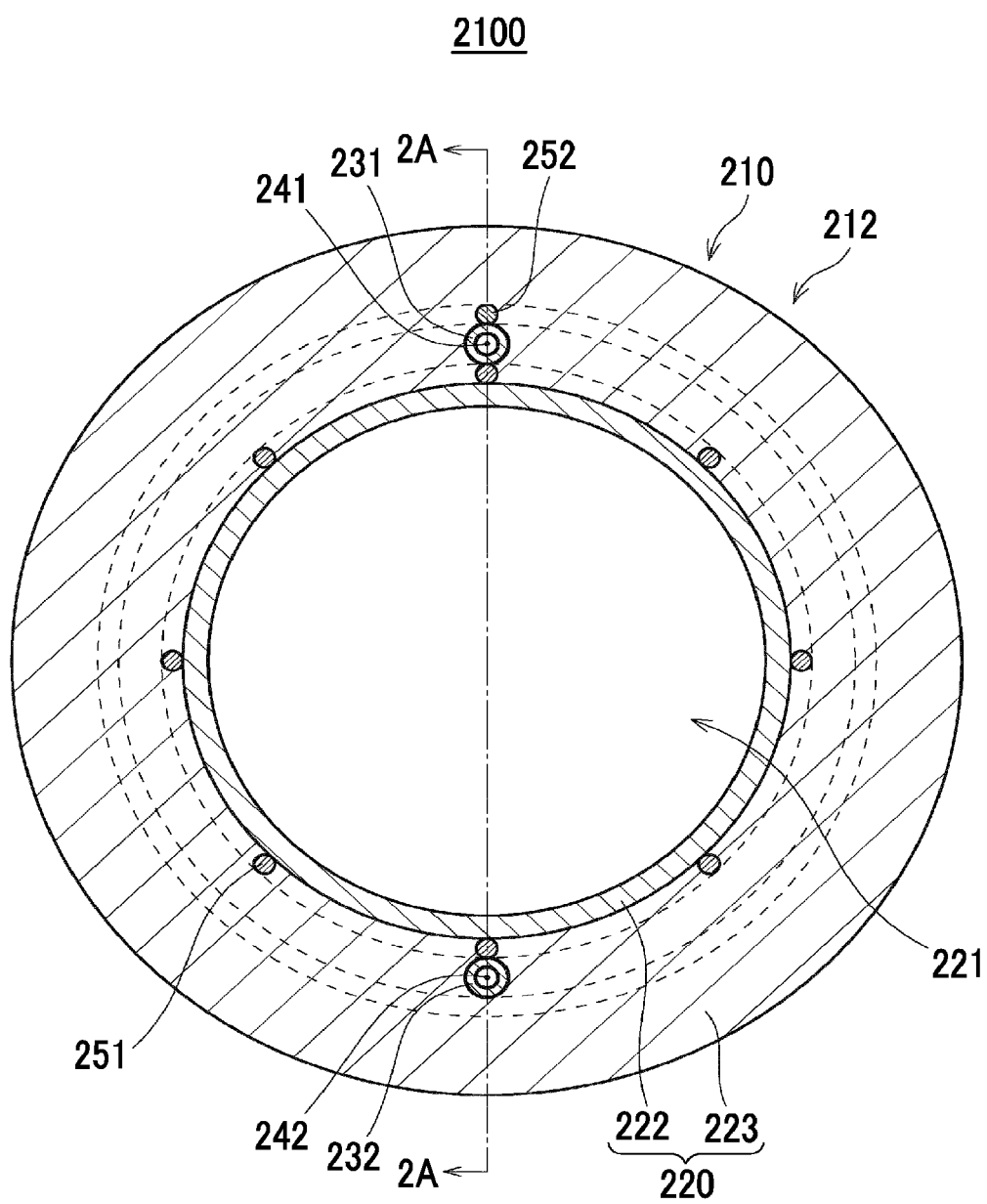
FIG. 22 is a cross-sectional view of the medical device body along line 2A-2A of FIG. 21.

FIG. 21 is a sectional view along line 2A-2A of FIG. 22.

Figure 24:
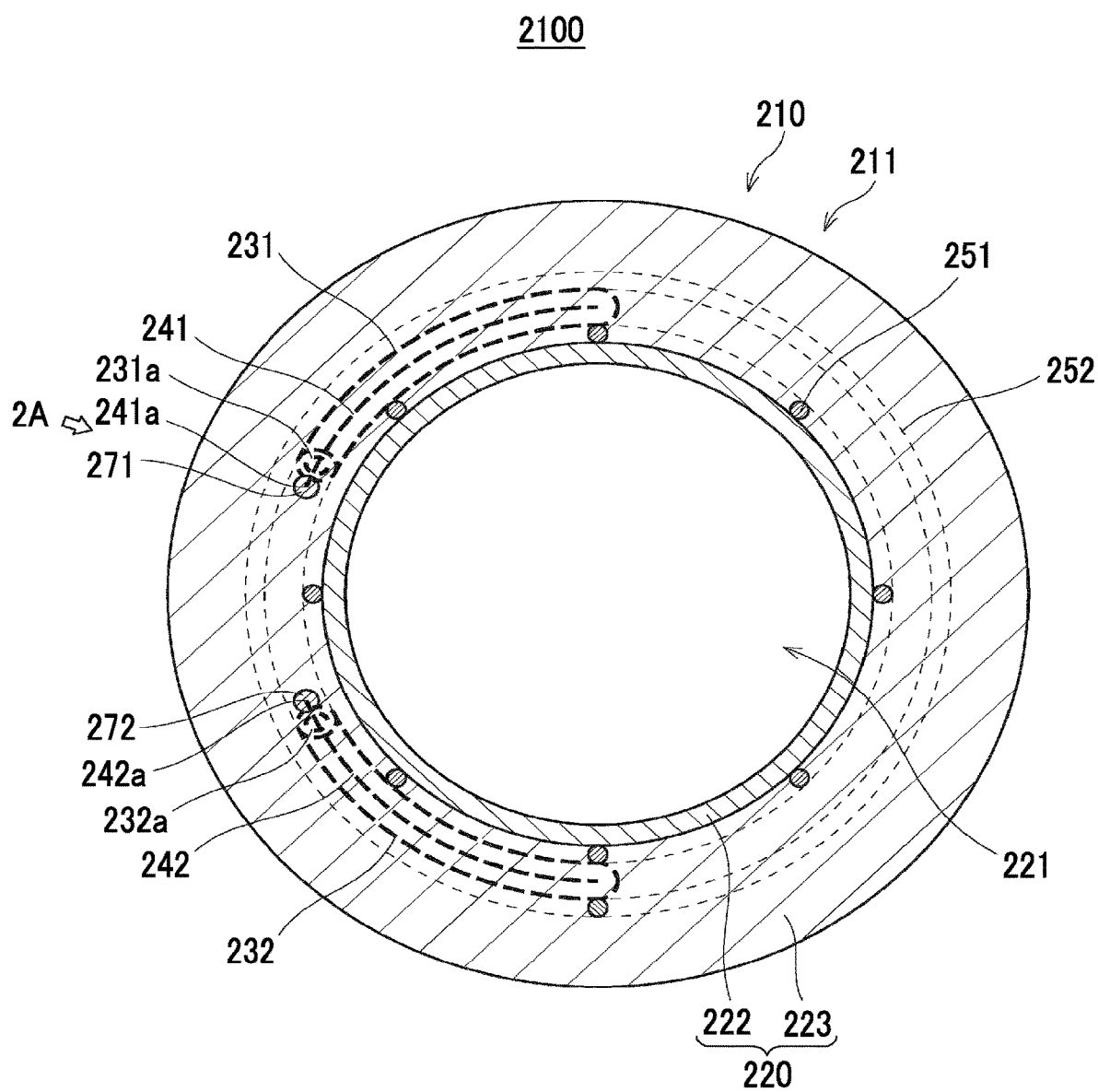
FIG. 24 is a cross-sectional view of the medical device body along line 2C-2C of FIG. 21.
Figure 25:
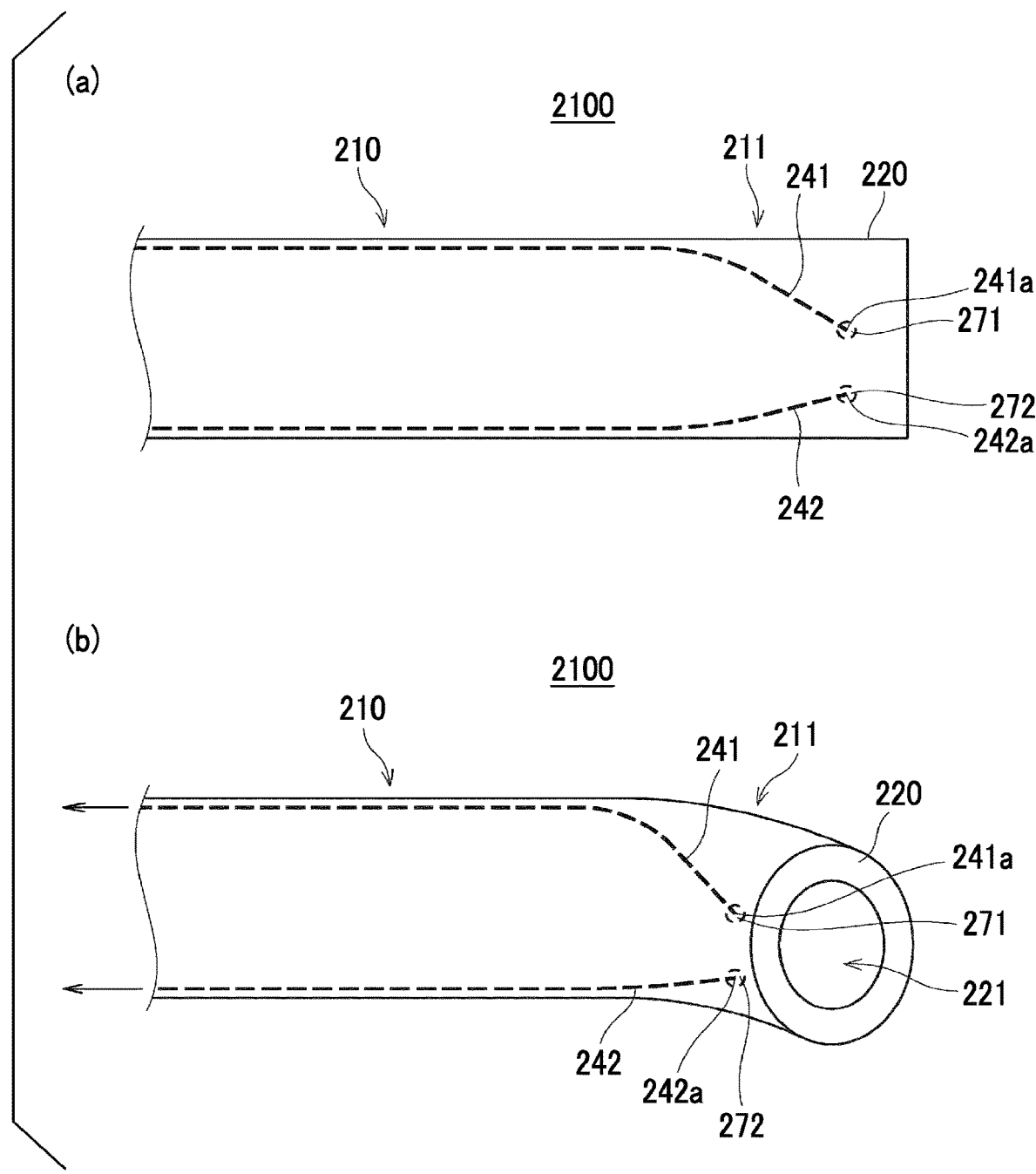
FIGS. 25(*a*) and 25(*b*) are schematic views for illustrating a bending motion of a distal end part of a medical device body of a medical device related to Embodiment 2-1.

FIGS. 25(a) and 25(b) are schematic views for illustrating a bending motion when a distal end part 211 of the medical device body 210 is seen in a direction of arrow 2A of FIG. 24, FIG. 25(a) illustrates a state before the bending, and FIG. 25(b) illustrates a bent state.

Figure 27:
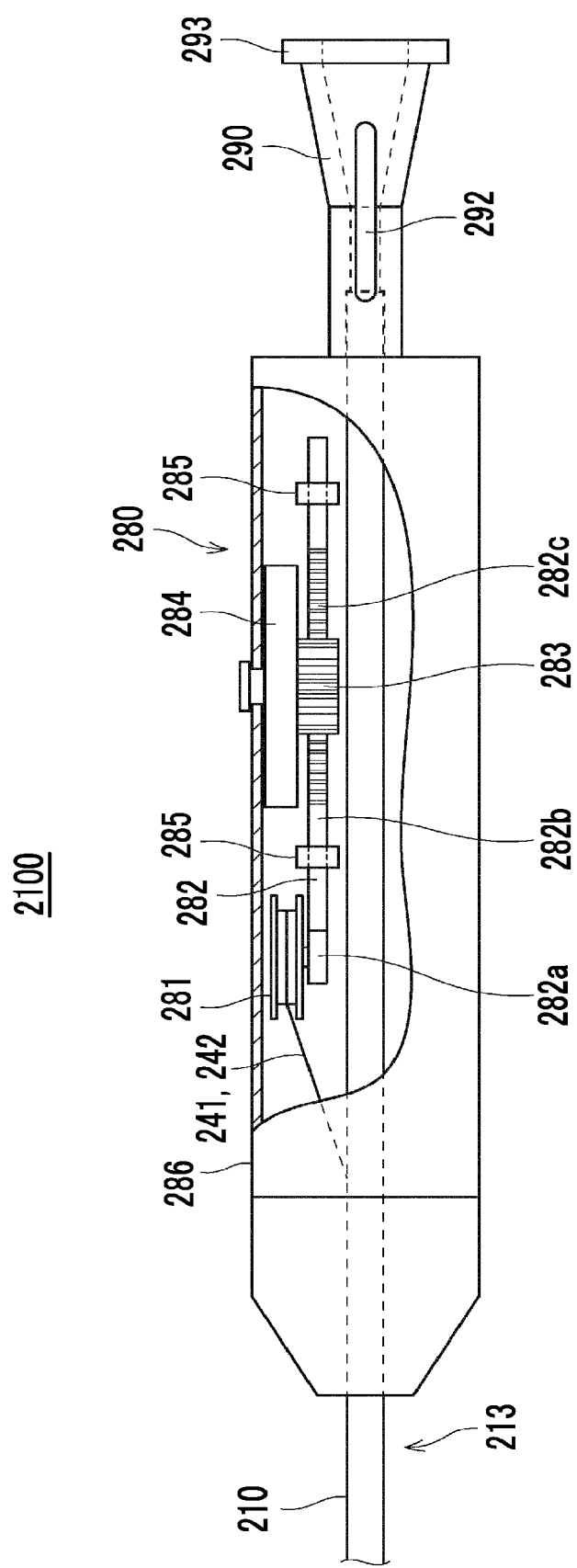
FIG. 27 is a side view illustrating the bending operating part and the portion in the vicinity thereof in the medical device related to Embodiment 2-1.
Figure 28:
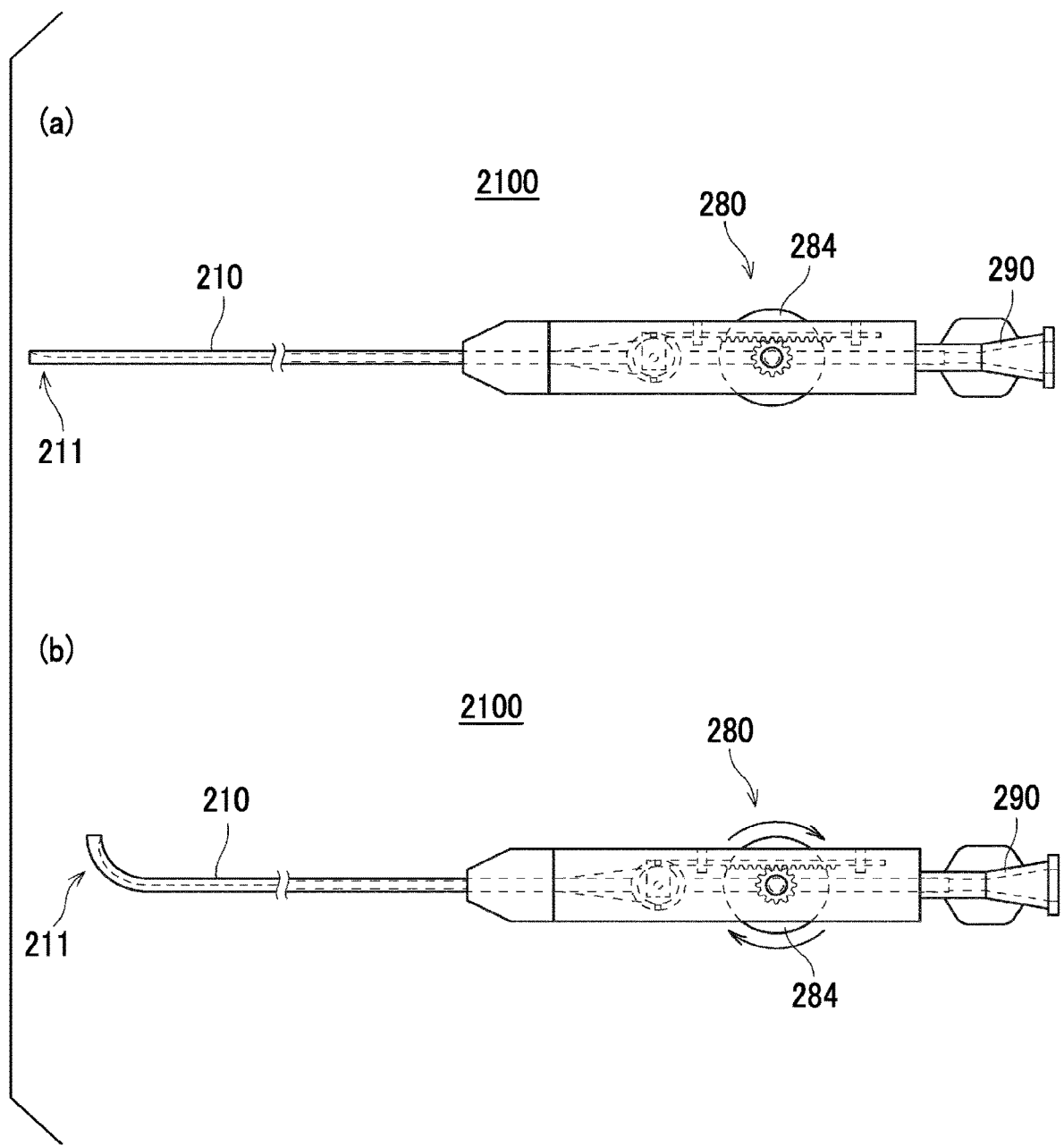
FIG. 28(*a*) is an overall view of the medical device related to Embodiment 2-1, and FIG. 28(*b*) is an overall view illustrating a state where the distal end part of the medical device body of the medical device related to Embodiment 2-1 is bent to one side.

In FIG. 27, a housing 286 of a bending operating part 280 is broken partially to illustrate the internal structure of the housing 286.

In FIGS. 28(a) and 28(b), a middle portion of the medical device body 210 in a longitudinal direction is broken and omitted. In the medical device body 210 illustrated in FIGS. 28(a) and 28(b), a portion closer to the proximal end side than the omitted portion and a portion closer to the distal end side than the omitted portion have rotational phases around the axis of the medical device body 210 that are different from each other by 90 degrees.

As illustrated in any of FIGS. 21 to 28(b), a medical device 2100 related to the present embodiment includes an elongated medical device body 210 configured to include an elongated resin tube 220 having a lumen 221, and a first hollow tube 231 and a second hollow tube 232 that are buried in an axial direction of the resin tube 220 and has a first operating line 241 and a second operating line 242 inserted therethrough, respectively, and a bending operating part 280 (FIG. 26, FIG. 27) for performing the bending operation of the distal end part 211 of the medical device body 210 by pulling the first operating line 241 and the second operating line 242.

The first hollow tube 231 and the second hollow tube 232 are respectively sublumen tubes, and inner cavities of these sublumen tubes are sublumens. That is, the operating lines (the first operating line 241, the second operating line 242) are respectively inserted through the sublumens.

At an intermediate part 212 and a proximal end part 213 (FIG. 26, FIG. 27) in the axial direction of the medical device body 210, the first operating line 241 and the second operating line 242 extend in parallel so as to be spaced apart from each other in a circumferential direction of the medical device body. A curved region 215 where the first operating line 241 and the second operating line 242 are gradually curved so as to approach each other in the circumferential direction of the medical device body 210 toward the distal end side is formed at the distal end part 211 in the axial direction of the medical device body 210. A distal end 241a of the first operating line 241 and a distal end 242a of the second operating line 242 are spaced apart from each other in the circumferential direction of the medical device body 210, and are fixed to the medical device body 210.

According to the present embodiment, the distal end part 211 of the medical device body 210 can be bent as illustrated in FIGS. 25(a) and 25(b) by pulling both of the first operating line 241 and the second operating line 242. In this case, the load of pulling the distal end part 211 of the medical device body 210 with the first operating line 241 and the load of pulling the distal end part 211 with the second operating line 242 can be balanced with each other. Therefore, occurrence of a phenomenon in which the medical device body 210 rotates around an axis such that the first operating line 241 or the second operating line 242 tends to take a shortcut can be suppressed.

Hence, even when the distal end part 211 is further bent after the medical device body 210 passes through a body cavity, such as a curved blood vessel, it is possible to more reliably bend the distal end part 211 in a desired direction.

As in the case of the present embodiment, in a case where the number of operating lines provided in the medical device 2100 is two, and these operating lines are joined together, a direction in which the distal end part 211 can be bent by pulling the operating lines is one direction.

Additionally, the first hollow tube 231 and the second hollow tube 232 are disposed avoiding a center position (a position serving as an antinode of the bending) of a portion on an in-course side when the medical device body 210 is bent. Therefore, the rigidity of the first hollow tube 231 and the outer layer 223 can be restrained from interfering with the bending of the medical device body 210, and the medical device body 210 can be more easily bent. Since the first hollow tube 231 and the second hollow tube 232 are spaced apart from the in-course side, particularly on a further proximal end side in the distal end part 211, the bending becomes easy.

Hence, it is possible to more reliably bend the distal end part 211 in a desired direction while suppressing an increase in force required for the pulling operation of the first operating line 241 and the second operating line 242.

Additionally, since the distal end 241a of the first operating line 241 and the distal end 242a of the second operating line 242 are spaced apart from each other in the circumferential direction of the medical device body 210, the curving of the first hollow tube 231 and the second hollow tube 232 in the curved region 215 can be made gentle. Therefore, an increase in the frictional resistance between the first hollow tube 231 and the first operating line 241 and the frictional resistance between the second hollow tube 232 and the second operating line 242 can be suppressed.

Here, when the medical device 2100 is manufactured, for example, a process of thermoforming the outer layer 223 (to be described below) of the resin tube 220 where sub-cores (not illustrated) are respectively inserted through the first hollow tube 231 and the second hollow tube 232 in advance, and then, pulling and extracting the sub-cores, respectively, and replacing the sub-cores with the first operating line 241 and the second operating lines 242 coupled to the sub-cores, respectively, is performed.

In the present embodiment, since the curving of the first hollow tube 231 and the second hollow tube 232 in the curved region 215 can be made gentle, the extraction of the sub-cores can be easily performed.

The medical device 2100 is, typically, a catheter.

In the case of the present embodiment, the resin tube 220 has a layer structure including a hollow tubular inner layer 222 of which an inner cavity is the lumen 221, and a hollow tubular outer layer 223 that is formed coaxially with the inner layer 222 and at an outer periphery of the inner layer 222. The inner layer 222 and the outer layer 223 are respectively made of resin materials. An inner peripheral surface of the outer layer 223 is joined to an outer peripheral surface of the inner layer 222.

A resin material constituting the inner layer 222 and a resin material constituting the outer layer 223 may be different from each other, or may be the same as each other.

A hydrophilic coat may be formed on an outer surface layer of the medical device body 210 as necessary.

The lumen 221 is continuously formed from a distal end of the medical device body 210 to a proximal end thereof, and opens at the distal end and the proximal end of the medical device body 210, respectively.

The internal diameters of the first hollow tube 231 and the second hollow tube 232 are smaller than the internal diameter of the lumen 221.

The first operating line 241 and the second operating line 242 are respectively constituted of thin lines, such as metal or resin.

At the distal end part 211 of the medical device body 210 in the axial direction, the first hollow tube 231 and the second hollow tube 232 are gradually curved so as to approach each other in the circumferential direction of the medical device body 210 toward the distal end side. Accordingly, the first operating line 241 within the first hollow tube 231 and the second operating line 242 within the second hollow tube 232 are gradually curved so as to approach each other in the circumferential direction of the medical device body 210 toward the distal end side.

The first hollow tube 231 and the second hollow tube 232 do not intersect each other. Additionally, the first operating line 241 and the second operating line 242 do not intersect each other.

In the present specification, a region where the first operating line 241 and the second operating line 242 are gradually curved so as to approach each other in the circumferential direction of the medical device body 210 toward the distal end side in the axial direction of the medical device body 210 is referred to as a curved region 215. A proximal end position 215a of the curved region 215 is a position where the first operating line 241 and the second operating line 242 starts to be curved toward each other, and a distal end position 215b of the curved region 215 is a position where the first operating line 241 and the second operating line 242 finishes being curved toward each other.

In the case of the present embodiment, the distal end position 215b of the curved region 215 is a position where the distal ends 241a and 242a of the first operating line 241 and the second operating line 242 are disposed, or a position in the vicinity thereof.

The distal end 241a of the first operating line 241 protrudes from a distal end 231a of the first hollow tube 231. Similarly, the distal end 242a of the second operating line 242 protrudes from a distal end 232a of the second hollow tube 232.

For example, the distal end 241a is located in the vicinity of the distal end 231a, and the distal end 242a is located in the vicinity of the distal end 232a.

The medical device body 210 includes, for example, a braid layer 251 buried in the resin tube 220. Accordingly, the medical device body 210 is reinforced by the braid layer 251. The braid layer 251 is configured by braiding two or more wires. The braid layer 251 is disposed, for example, around the inner layer 222.

The first hollow tube 231 and the second hollow tube 232 are disposed, for example, on a further radially outer side (at a position far from an axis of the medical device body 210) of the medical device body 210 than the braid layer 251.

The medical device body 210 further includes a winding wire 252 buried in the resin tube 220. The winding wire 252 is wound on a further radially outer side of the medical device body 210 than the braid layer 251, the first hollow tube 231, and the second hollow tube 232. For example, the winding wire 252 constrains the first hollow tube 231 and the second hollow tube 232 with respect to the braid layer 251.

Figure 23:
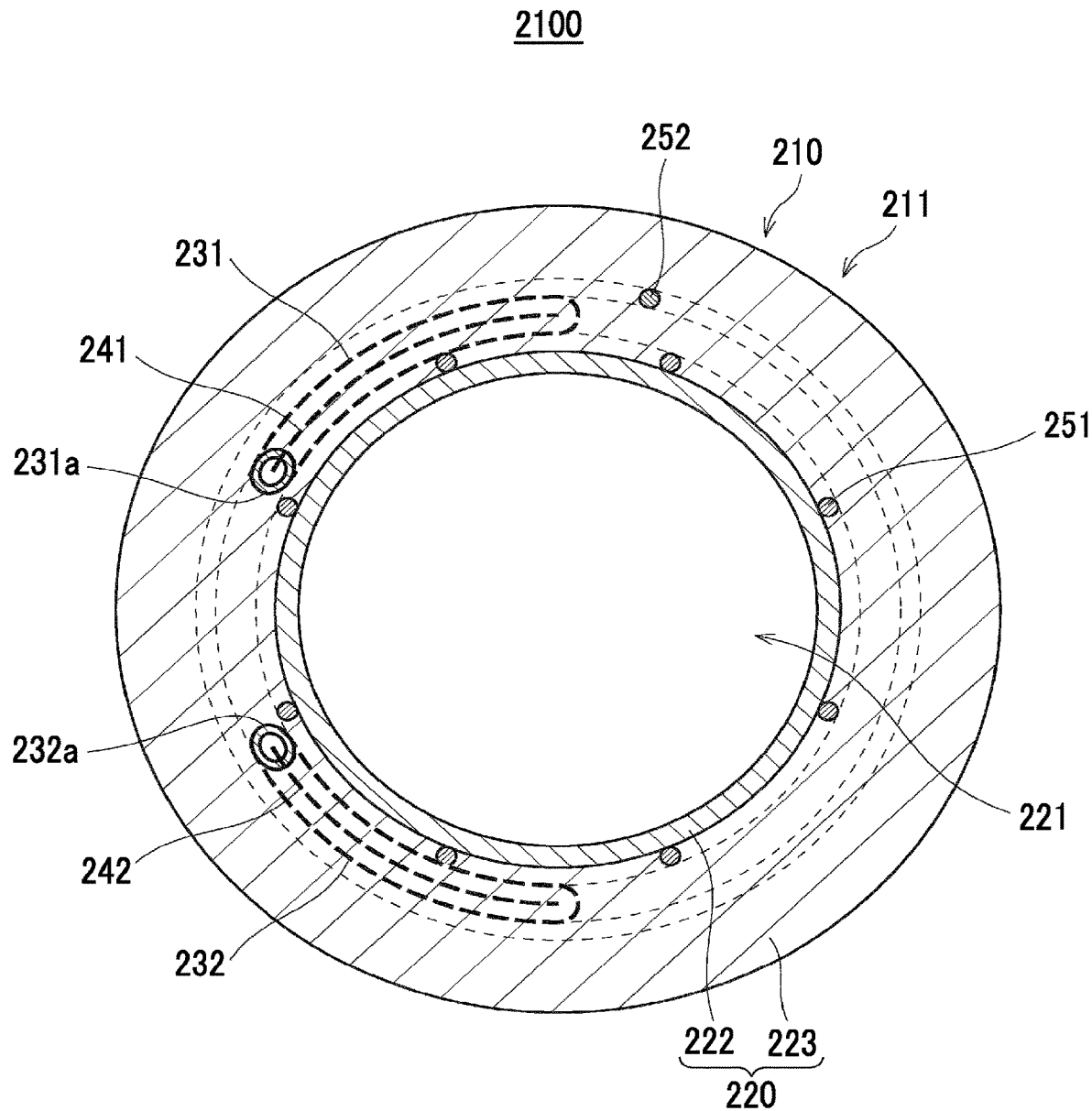
FIG. 23 is a cross-sectional view of the medical device body along line 2B-2B of FIG. 21.

In the curved region 215, the first hollow tube 231 and the second hollow tube 232 are disposed along an outer periphery of the braid layer 251 (refer to FIGS. 23 and 24).

In the curved region 215, the distance between the first hollow tube 231 and the second hollow tube 232 in the circumferential direction of the medical device body 210 decreases gradually toward the distal end side, and the distance between the first operating line 241 and the second operating line 242 in the circumferential direction of the medical device body 210 decreases gradually toward the distal end side. The first hollow tube 231 and the second hollow tube 232 are deformed in a curved shape, for example, on a further distal end side than the proximal end position 215a of the curved region 215.

The first hollow tube 231 and the second hollow tube 232 may be fixed to at least one of the braid layer 251 or the inner layer 222 at the proximal end position 215a of the curved region 215, or the distal end of the winding wire 252 may be disposed at the proximal end position 215a of the curved region 215, and the first hollow tube 231 and the second hollow tube 232 may not be constrained by the winding wire 252 on a further distal end side than the proximal end position 215a.

At the intermediate part 212 and the proximal end part 213 in the axial direction of the medical device body 210, the first operating line 241 and the second operating line 242 are disposed at positions that face each other in the circumferential direction of the medical device body 210.

In the case of the present embodiment, for example, as illustrated in FIG. 22, at the intermediate part 212 of the medical device body 210, the first operating line 241 and the second operating line 242 face each other by 180 degrees in the circumferential direction of the medical device body 210 with the axis of the medical device body 210 as a reference. Similarly, even at the proximal end part 213 of the medical device body 210 and the proximal end position 215a of the curved region 215, the first operating line 241 and the second operating line 242 face each other by 180 degrees in the circumferential direction of the medical device body 210. That is, at the intermediate part 212, the proximal end part 213, and the proximal end position 215a of the curved region 215, the phase difference between the first operating line 241 and the second operating line 242 in the circumferential direction of the medical device body 210 is 180 degrees.

However, the fact that the first operating line 241 and the second operating line 242 disposed at positions that face each other in the circumferential direction of the medical device body 210 is not limited to this example, and means that the first operating line 241 and the second operating line 242 are spaced apart from each other by 120 degrees or more in the circumferential direction of the medical device body 210.

The phase difference between the first operating line 241 and the second operating line 242 in the circumferential direction of the medical device body 210 decreases gradually toward the distal end side in the curved region 215.

In the circumferential direction of the medical device body 210, in the curved region 215, the first operating line 241 and the second operating line 242 are preferably rotated (curved) at an angle of 30 degrees or more, and are more preferably rotated (curved) at an angle of 45 degrees or more. The first operating line 241 and the second operating line 242 are rotated (curved) at an angle of less than 90 degrees in the circumferential direction of the medical device body 210 in the curved region 215.

Additionally, in the case of the present embodiment, at the intermediate part 212, the proximal end part 213, and the proximal end position 215a of the curved region 215 in the medical device body 210, the first hollow tube 231 and the second hollow tube 232 face each other by 180 degrees in the circumferential direction of the medical device body 210 with the axis of the medical device body 210 as a reference. That is, at the intermediate part 212, the proximal end part 213, and the proximal end position 215a of the curved region 215, the phase difference between the first hollow tube 231 and the second hollow tube 232 in the circumferential direction of the medical device body 210 is 180 degrees. The phase difference decreases gradually toward the distal end side in the curved region 215.

In a configuration in which, at the intermediate part 212, the proximal end part 213, and the proximal end position 215a of the curved region 215 in the medical device body 210, the first hollow tube 231 and the second hollow tube 232 face each other at an angle of less than 180 degrees in the circumferential direction of the medical device body 210 with the axis of the medical device body 210 as a reference, the curving of the first hollow tube 231 and the second hollow tube 232 in the curved region 215 can be made gentler. Therefore, the extraction of the sub-cores from the first hollow tube 231 and the second hollow tube 232 becomes easy.

The distal end part 211 of the medical device body 210 is provided with a ring-shaped marker 270 made of a radiopaque metallic material. The marker 270 is disposed coaxially with the lumen 221 and around the lumen 221.

The marker 270 is disposed, for example, around the braid layer 251.

The distal end 241a of the first operating line 241 is fixed to the marker 270 by a first fixing part 271 that is, for example, spot-shaped solder.

Similarly, the distal end 242a of the second operating line 242 is fixed to the marker 270 by the first fixing part 271 that is, for example, spot-shaped solder.

The first fixing part 271 and the second fixing part 272 are disposed, for example, at an end part of the marker 270 on the proximal end side.

The first fixing part 271 and the second fixing part 272 are spaced apart from each other in the circumferential direction of the medical device body.

The distal end 241a of the first operating line 241 and the distal end 242a of the second operating line 242 are close to each other, for example, at a distance larger than the thickness of the resin tube 220 to be described below.

Next, a hub 290 provided at a proximal end part of the medical device body 210 will be described with reference to FIGS. 26 and 27.

The hub 290 has a coupling part 293 for inserting an injector (syringe), which is not illustrated, from a proximal end of the hub 290. A thread groove is formed at an outer periphery of the coupling part 293 so that the syringe can be detachably fixed.

Two wing parts 292, which face each other via an axis of the hub 290, are provided at an outer periphery of the hub 290.

The proximal end part of the medical device body 210 is inserted into and fixed to a distal end part of the hub 290. Accordingly, the lumen 221 inside the medical device body 210 and an internal space of the hub 290 communicate with each other.

By rotating the wing parts 292 about the axis of the hub 290, a torque operation for rotating the entire medical device body 210 about an axis is possible.

A housing 286 of the bending operating part 280 to be described below is connected and fixed to a distal end side of the hub 290.

Next, the bending operating part 280 provided in the medical device 2100 will be described with reference to FIGS. 26 and 27.

The medical device 2100 includes the bending operating part 280 for performing the bending operation of the distal end part 211 of the medical device body 210 by pulling the first operating line 241 and the second operating line 242.

The bending operating part 280 is configured to include a rotating member 281 that is rotatably supported and is engaged with the first operating line 241 and the second operating line 242 to which a proximal end part of the first operating line 241 and a proximal end part of the second operating line 242 are fixed, and a moving mechanism that moves the rotating member 281 in a pulling direction in which the first operating line 241 and the second operating line 242 are pulled, and an opposite direction opposite to the pulling direction.

The rotating member 281 is, for example, a pulley.

The moving mechanism is configured to include a forward/backward movable member 282 and a pinion 283.

The forward/backward movable member 282 includes a holding part 282a that rotatably holds the rotating member 281, and a rod-shaped part 282b that extends from the holding part 282a to the proximal end side of the medical device body 210.

A rack part 282c is formed in the rod-shaped part 282b.

The bending operating part 280 further includes the housing 286 that is a body part of the bending operating part 280, a dial operating part 284 rotatably supported to the housing 286, the pinion 283 provided integrally with the dial operating part 284, and a guide 285 (for example, a pair of front and rear guides 285) that is provided on an inner surface of the housing 286 to guide the rod-shaped part 282b in a longitudinal direction of the rod-shaped part 282b.

The proximal end part 213 of the medical device body 210 is guided to a proximal end side of the housing 286 through the inside of the housing 286, and is inserted into and fixed to the distal end part of the hub 290.

A rotating shaft of the dial operating part 284 extends in a direction orthogonal to an axis direction of the medical device body 210 within the housing 286.

The pinion 283 is formed integrally with the dial operating part 284 on one face side of the dial operating part 284, and is disposed coaxially with a rotational axis of the dial operating part 284.

A gear at an outer periphery of the pinion 283 meshes with a gear of the rack part 282c of the forward/backward movable member 282.

At least a portion of the dial operating part 284 is exposed to the outside of the housing 286 so that an operation in which the operator who performs the operation of the medical device 2100 rotates the dial operating part 284 can be performed from the outside of the housing 286.

The first operating line 241 and the second operating line 242 are delivered from the medical device body 210 within the housing 286.

Figure 26:
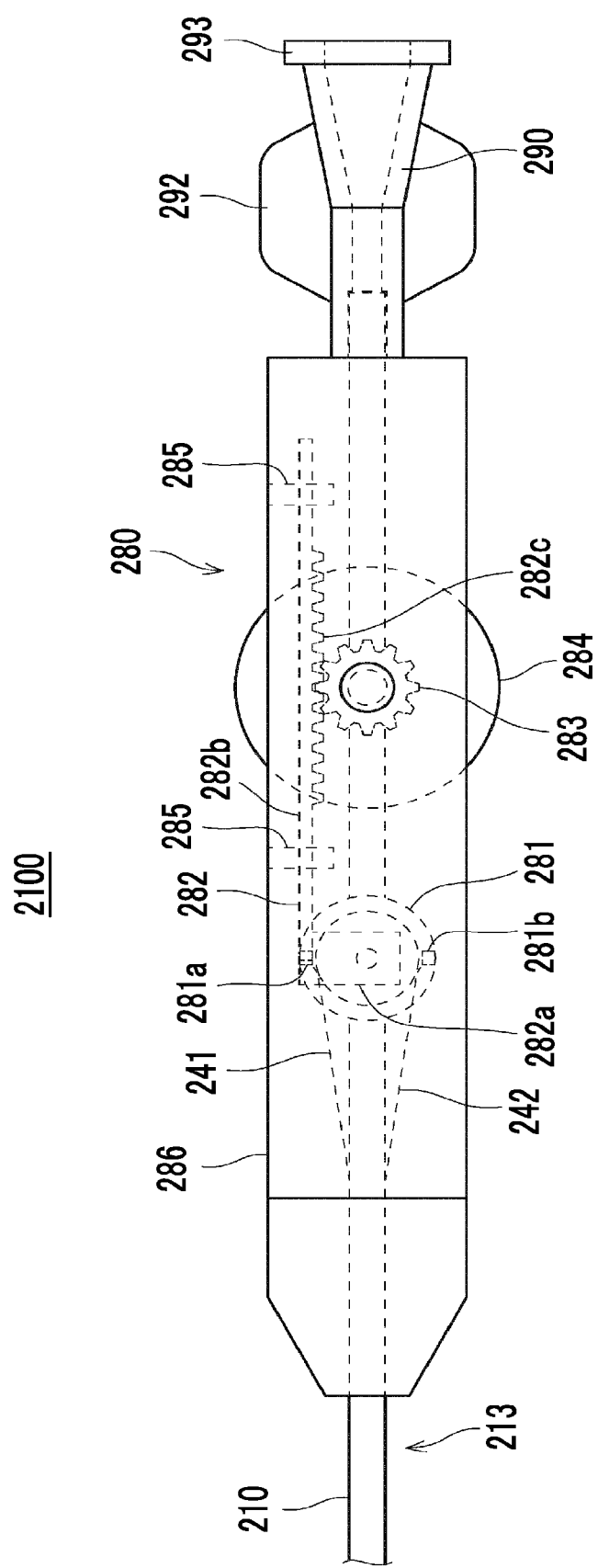
FIG. 26 is a plan view illustrating a bending operating part and a portion in the vicinity thereof in the medical device related to Embodiment 2-1.

The proximal end part of the first operating line 241 is wound around the rotating member 281, for example, by one and a half turns, and a proximal end of the first operating line 241 is fixed to the rotating member 281 by a first fixing part 281a (FIG. 26).

Similarly, the second operating line 242 is wound around the rotating member 281, for example, by one and a half turns, and a proximal end of the second operating line 242 is fixed to the rotating member 281 by a second fixing part 281b (FIG. 26).

The winding direction of the first operating line 241 and the winding direction of the second operating line 242 around the rotating member 281 are mutually opposite directions. For this reason, the rotational angle of the rotating member 281 is autonomously adjusted to an angle at which the tension of the first operating line 241 and the tension of the second operating line 242 are balanced with each other.

As the operator who performs the operation of the medical device 2100 grips the housing 286 or the hub 290 to rotate the dial operating part 284, the pinion 283 integral with the dial operating part 284 rotates about an axis. Along with this, the forward/backward movable member 282 having the rack part 282c moves forward (moves to the distal end side of the medical device body 210) or moves backward (moves to the proximal end side of the medical device body 210) in the axial direction of the medical device body 210 relative to the housing 286.

In FIG. 26, by rotating the dial operating part 284 in the clockwise direction, the forward/backward movable member 282 and the rotating member 281 moves backward, and both of the first operating line 241 and the second operating line 242 are pulled to the proximal end side of the medical device body 210.

In this way, the first operating line 241 and the second operating line 242 are pulled at a time by the operation on the bending operating part 280.

Here, "the first operating line 241 and the second operating line 242 are pulled at a time" means that a timing when both of the first operating line 241 and the second operating line 242 are pulled is present, and is not limited to timings when pulling is started by the first operating line 241 and the second operating line 242 being the same, and is not limited to timings when pulling is ended by the first operating line 241 and the second operating line 242 being the same.

For example, as illustrated in FIG. 28(a), when the distal end part 211 of the medical device body 210 has a linear shape, both of the first operating line 241 and the second operating line 242 are pulled to the proximal end side of the medical device body 210 if the dial operating part 284 is rotated in the clockwise direction in FIG. 28(b). Therefore, the distal end part 211 of the medical device body 210 is bent in one direction.

If the dial operating part 284 is rotated in the counterclockwise direction from the state of FIG. 28(b), the forward/backward movable member 282 and the rotating member 281 move forward, and the tension of the first operating line 241 and the second operating line 242 are released. Therefore, the distal end part 211 of the medical device body 210 is allowed to return linearly.

In this way, in the case of the present embodiment, the bending operating part 280 is configured to receive an operation performed by a user with the rotating mechanism (dial operating part 284) and convert a force applied to the rotating mechanism by this operation into a forward/backward movement in the axial direction of the medical device body 210 with the conversion mechanism constituted of the pinion 283 and the rack (rack part 282*c*).

Next, examples of the materials of the respective units of the medical device 2100 will be described.

As the materials of the inner layer 222, for example, resin materials, such as polytetrafluoroethylene (PTFE), polyvinylidene fluoride (PVDF), and perfluoroalkoxy fluororesin (PFA), can be used.

As the materials of the outer layer 223, in addition to polyimide (PI), polyamide imide (PAI), and polyethylene terephthalate (PET), resin materials, such as polyethylene (PE), polyamide (PA), nylon elastomer, polyurethane (PU), ethylene-vinyl acetate resin (EVA), polyvinyl chloride (PVC), or polypropylene (PP), can be used.

As the materials of the first hollow tube 231 and the second hollow tube 232, for example, resin materials, such as polytetrafluoroethylene (PTFE), polyvinylidene fluoride (PVDF), and perfluoroalkoxy fluororesin (PFA), can be used.

Although metallic materials, such as stainless steel and tungsten, are preferable as the materials of the wire that constitutes the braid layer 251, the materials of the wire may be, for example, resin materials.

Although the metallic materials, such as stainless steel and tungsten, are preferable as the materials of the wire that constitutes the winding wire 252, the materials of the wire may be, for example, resin materials.

According to the medical device 2100 related to Embodiment 2-1 as described above, the distal end part 211 of the medical device body 210 can be bent by pulling both of the first operating line 241 and the second operating line 242. In that case, a load for pulling the distal end part 211 of the medical device body 210 with the first operating line 241, and a load for pulling the distal end part 211 with the second operating line 242 can be balanced with each other. Therefore, the occurrence of the phenomenon in which the medical device body 210 rotates around an axis such that the first operating line 241 or the second operating line 242 tends to take a shortcut can be suppressed.

Therefore, it is possible to more reliably bend the distal end part 211 of the medical device body 210 in a desired direction.

Additionally, the first hollow tube 231 and the second hollow tube 232 are disposed avoiding a center position (a position serving as an antinode of the bending) of a portion on an in-course side when the medical device body 210 is bent. Therefore, the rigidity of the first hollow tube 231 and the outer layer 223 can be restrained from interfering with the bending of the medical device body 210, and the medical device body 210 can be more easily bent. Since the first hollow tube 231 and the second hollow tube 232 are spaced apart from the in-course side, particularly on a further proximal end side in the distal end part 211, the bending becomes easy.

Additionally, when the medical device 2100 is manufactured, in a case where the outer layer 223 (to be described below) of the resin tube 220 where sub-cores (not illustrated) are respectively inserted through the first hollow tube 231 and the second hollow tube 232 are thermoformed in advance, and then, the sub-cores are pulled and extracted, respectively, and the sub-cores are replaced with the first operating line 241 and the second operating lines 242 coupled to the sub-cores, respectively, the extraction of the sub-cores can be easily performed.

Embodiment 2-2

Figure 29:
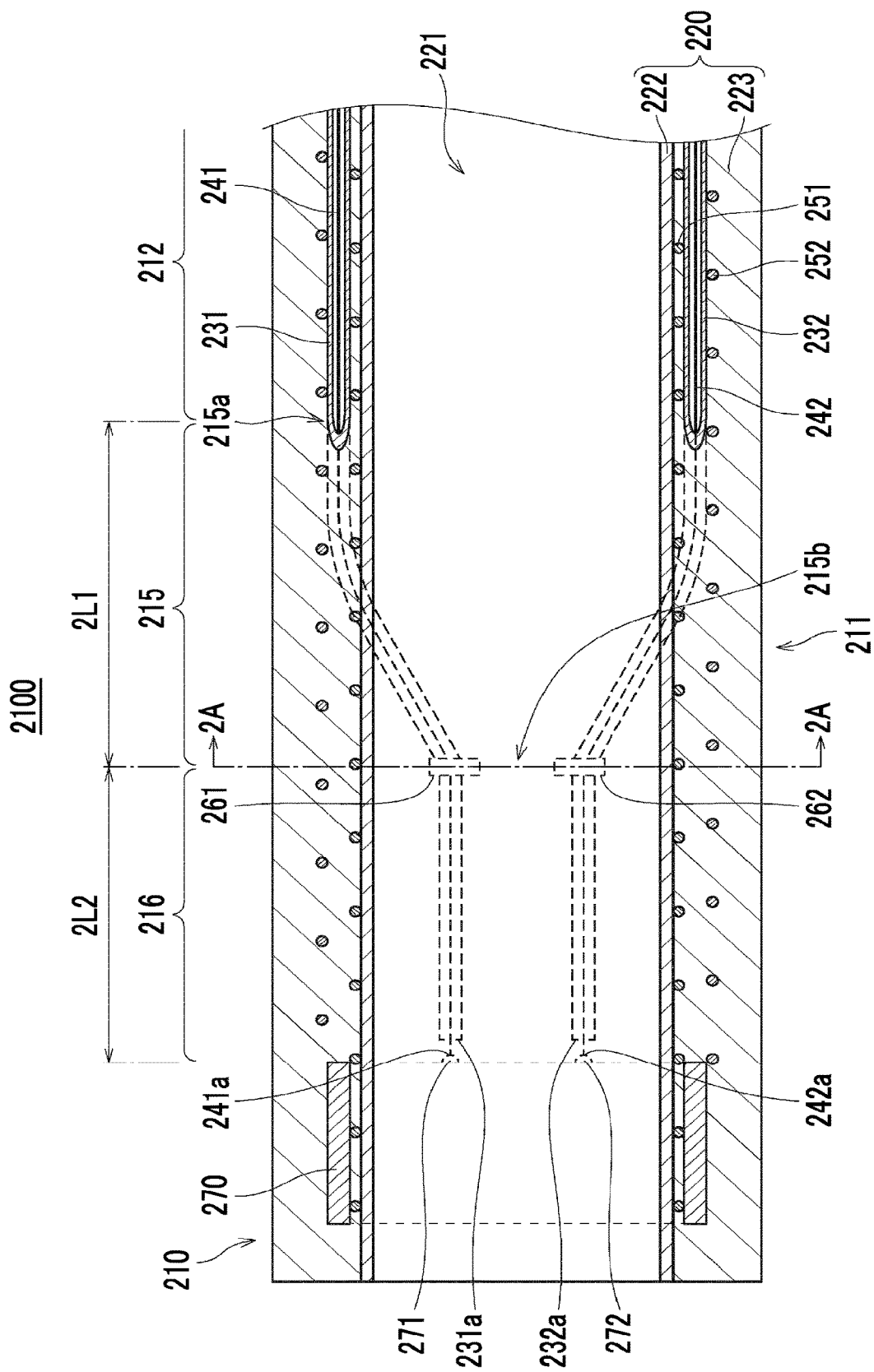
FIG. 29 is a longitudinal sectional view illustrating a portion on a distal end side in a medical device body of a medical device related to Embodiment 2-2.

Next, the medical device 2100 related to Embodiment 2-2 will be described with reference to FIGS. 29 to 31(*b*).

Figure 30:
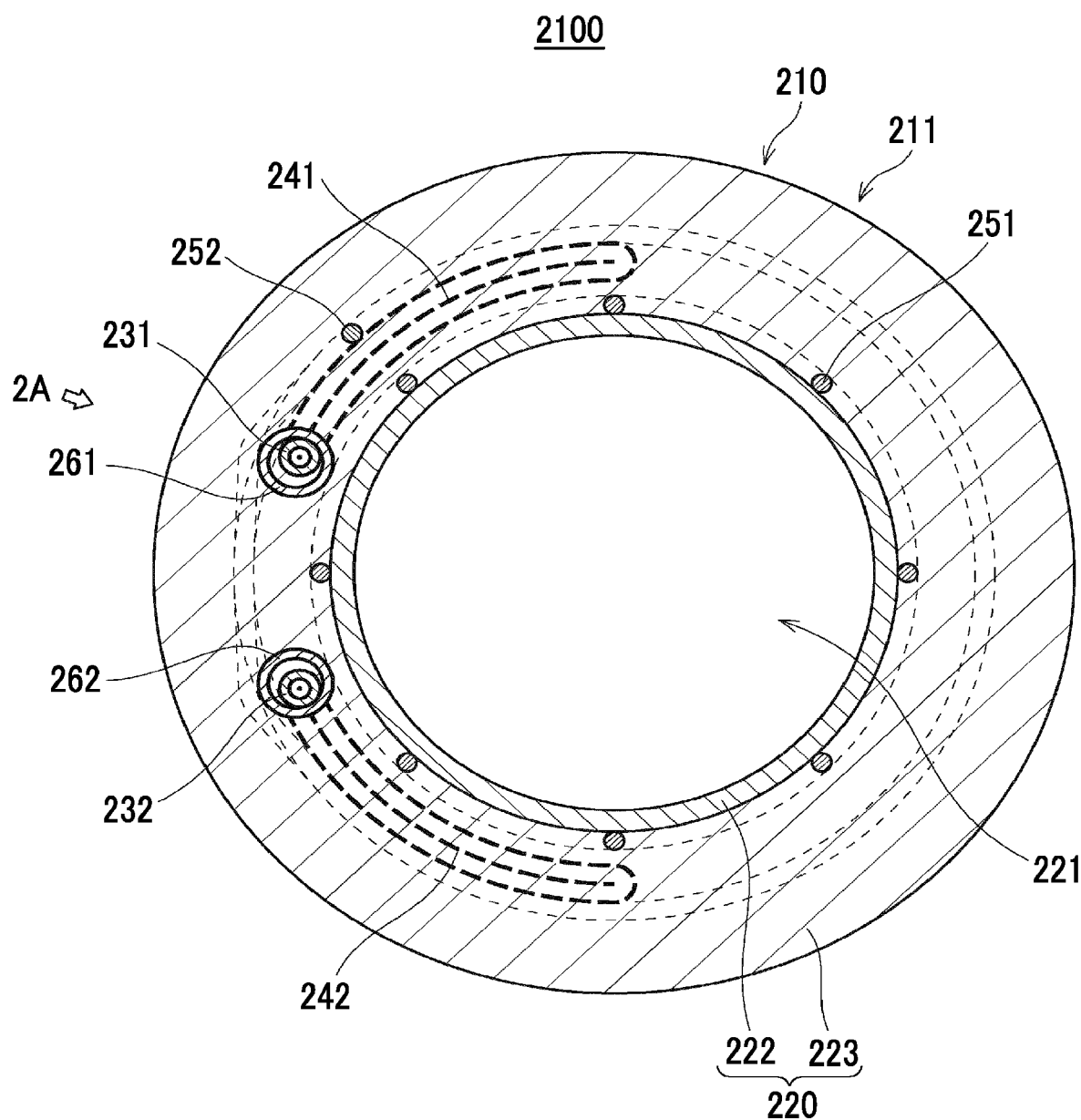
FIG. 30 is a cross-sectional view of the medical device body along line 2A-2A of FIG. 29.
Figure 31:
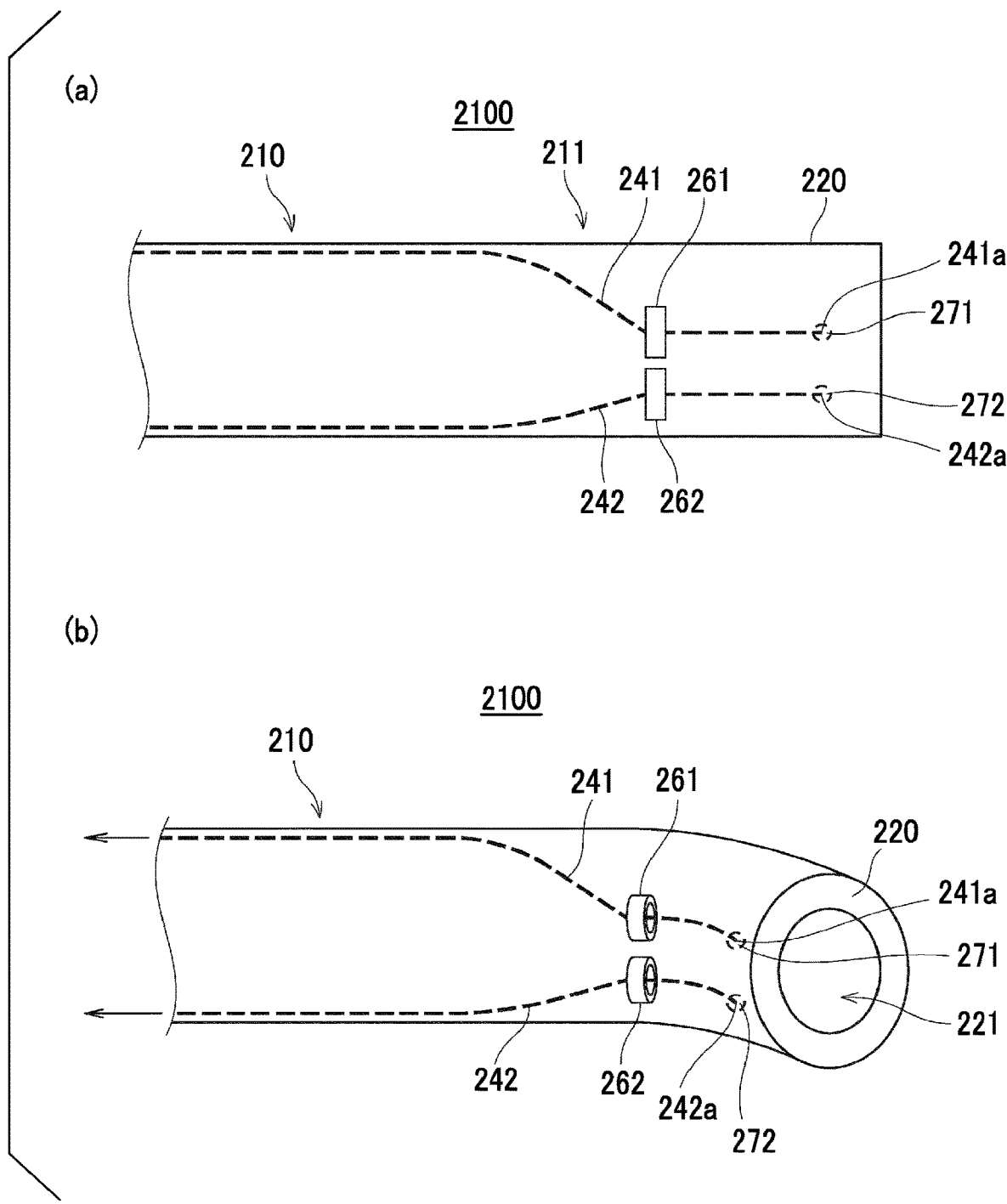
FIGS. 31(*a*) and 31(*b*) are schematic views for illustrating the bending motion of a distal end part of the medical device body of the medical device related to Embodiment 2-2.
Figure 32:
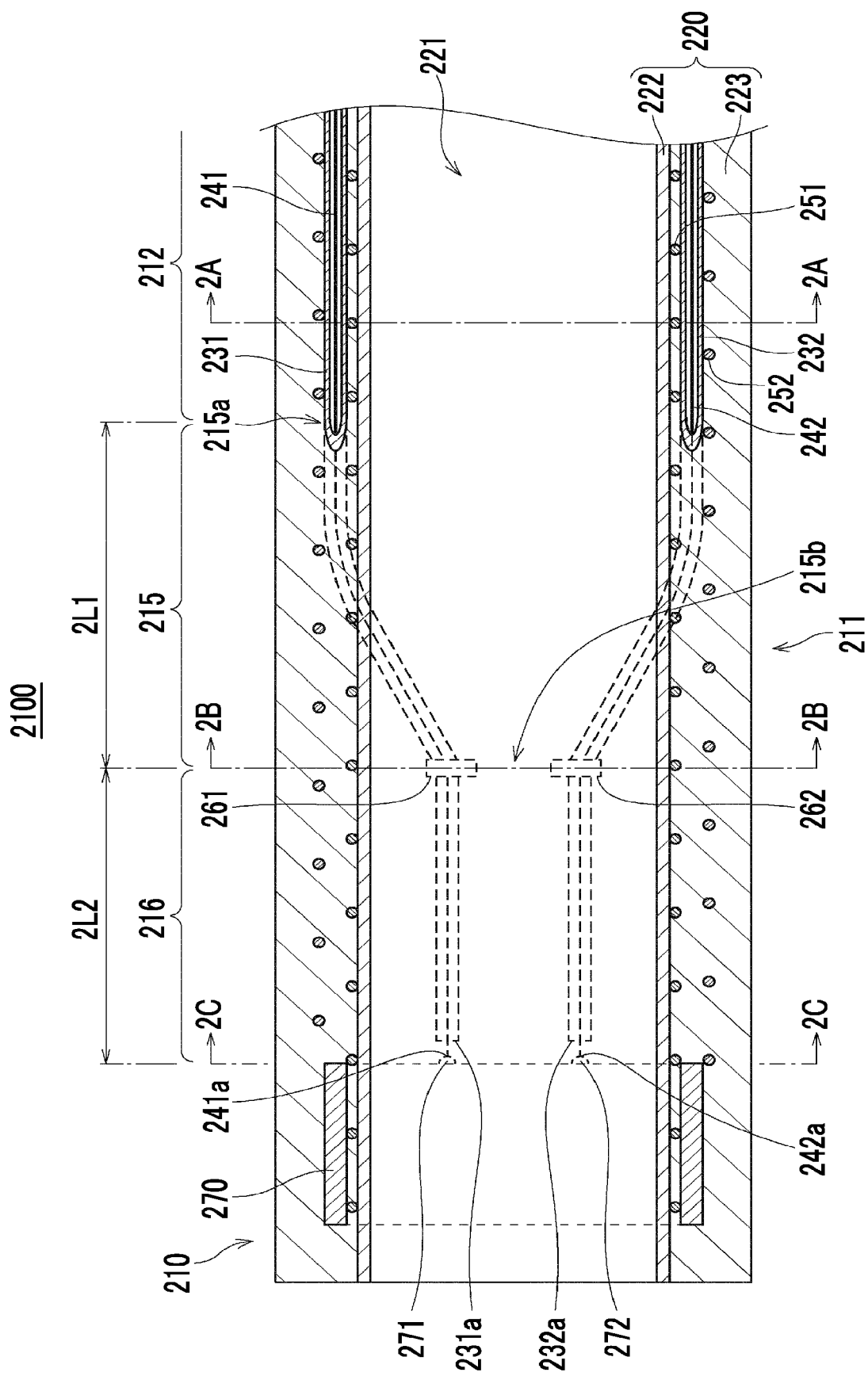
FIG. 32 is a longitudinal sectional view illustrating a portion on a distal end side in a medical device body of a medical device related to Embodiment 2-3.

FIGS. 31(*a*) and 31(*b*) are schematic views for illustrating the bending motion when the distal end part 211 of the medical device body 210 is seen in the direction of arrow 2A of FIG. 30, FIG. 31(*a*) illustrates the state before the bending, and FIG. 31(*b*) illustrates the bent state.

The medical device 2100 related to the present embodiment is different from the medical device 2100 related to the above Embodiment 2-1 in terms of points to be described below, and is configured similarly to the medical device 2100 related to the above Embodiment 2-1 in terms of the other points.

In the case of the present embodiment, a parallel region 216 where the first operating line 241 and the second operating line 242 extend parallel to each other is formed between a distal end (distal end position 215*b*) of the curved region 215, and the distal ends 241*a* and 242*a* of the first operating line 241 and the second operating line 242.

That is, the parallel region 216 where the first operating line 241 and the second operating line 242 extend in parallel closer to each other than the distances therebetween at the intermediate part 212 and the proximal end part 213 on the distal end side of the curved region 215 is formed at the distal end part 211 in the axial direction of the medical device body 210.

In the parallel region 216, the first hollow tube 231 and the second hollow tube 232 extend in parallel closer to each other than the distances therebetween at the intermediate part 212 and the proximal end part 213.

Additionally, at the distal end (distal end position 215*b*) of the curved region 215, the first operating line 241 and the second operating line 242 are close to each other in the circumferential direction of the resin tube 220 at a distance smaller than at the intermediate part 212 and the proximal end part 213 in the axial direction of the resin tube 220, and the parallel region 216 where the first operating line 241 and the second operating line 242 extend in parallel close to each other is formed between the distal end of the curved region 215 and the distal ends 241*a* and 242*a* of the first operating line 241 and the second operating line 242.

In the case of the present embodiment, the medical device 2100 includes an annular member buried in the resin tube 220 at the distal end part of the curved region 215.

The annular member is configured to have a rigidity higher than the resin tube 220, and have an external diameter smaller than the thickness of the resin tube 220 (refer to FIG. 30).

The first operating line 241 and the second operating line 242 are inserted through the annular member.

Accordingly, fluctuations of paths of the first operating line 241 and the second operating line 242 can be more reliably suppressed.

Here, the first operating line 241 and the second operating line 242 may be inserted through one common annular member. However, in the case of the present embodiment, two annular members of the first annular member 261 and the second annular member 262 are buried in the resin tube 220, and the first operating line 241 is inserted through the first annular member 261, and the second operating line 242 is inserted through the second annular member 262.

As long as the first operating line 241 and the second operating line 242 are spaced apart from each other, the first annular member 261 and the second annular member 262 may be in contact with each other. In the case of the present embodiment, the first annular member 261 and the second annular member 262 are disposed so as to be spaced apart from each other in the circumferential direction of the medical device body 210.

More specifically, in the case of the present embodiment, the first hollow tube 231 and the second hollow tube 232 are inserted through the annular member. In the curved region 215, the first hollow tube 231 and the second hollow tube 232 are gradually curved so as to approach each other in the circumferential direction of the medical device body 210 toward the distal end side.

Here, the first hollow tube 231 and the second hollow tube 232 may be inserted through one common annular member. However, in the case of the present embodiment, two annular members of the first annular member 261 and the second annular member 262 are buried in the resin tube 220, and the first hollow tube 231 is inserted through the first annular member 261, and the second hollow tube 232 is inserted through the second annular member 262.

Although the materials of the first annular member 261 and the second annular member 262 are not particularly limited, the first annular member 261 and the second annular member 262 can be made of, for example, metal or hard resin.

Even in the case of the present embodiment, by pulling both of the first operating line 241 and the second operating line 242, the distal end part 211 of the medical device body 210 can be bent as illustrated in FIGS. 31(a) and 31(b).

In this case, the bending angle in the parallel region 216 becomes steeper than the bending angle in the curved region 215.

As an example, a distance (a distance 2L2 illustrated in FIG. 29) from the distal end (distal end position 215b) of the curved region 215 to the distal ends 241a and 242a of the first operating line 241 and the second operating line 242 is longer than a distance (a distance 2L1 illustrated in FIG. 29) from the proximal end (proximal end position 215a) of the curved region 215 to the distal end (distal end position 215b) thereof in the axial direction of the medical device body 210.

By virtue of such a configuration, the distal end part 211 can be more easily bent.

Additionally, the bending of the distal end part 211 can be caused mainly in the parallel region 216. For this reason, the friction between the first operating line 241 and the first hollow tube 231 in the curved region 215 and the friction between the second operating line 242 and the second hollow tube 232 can be substantially uniformly maintained irrespective of the bending angle of the distal end part 211. Therefore, the magnitude of a force required for pulling the first operating line 241 and the second operating line 242 can be substantially uniformly maintained irrespective of the bending angle of the distal end part 211.

Additionally, as another example, the distance (the distance 2L1 illustrated in FIG. 29) from the proximal end (proximal end position 215a) of the curved region 215 to the distal end (distal end position 215b) thereof is longer than the distance (the distance 2L2 illustrated in FIG. 29) from the distal end (distal end position 215b) of the curved region 215 to the distal ends 241a and 242a of the first operating line 241 and the second operating line 242 in the axial direction of the medical device body 210.

By virtue of such a configuration, the flexibility of the distal end part 211 can be suppressed to some extent.

Additionally, the curving of the first operating line 241, the second operating line 242, the first hollow tube 231, and the second hollow tube 232 in the curved region 215 can be made gentle. Therefore, the friction between the first operating line 241 and the first hollow tube 231 in the curved region 215 and the friction between the second operating line 242 and the second hollow tube 232 can be reduced.

Additionally, a length region where the first hollow tube 231 and the second hollow tube 232 translate close to each other in the distal end part 211 of the medical device body 210, that is, a length region with high rigidity is high becomes short. Therefore, excellent selectivity (excellent blood vessel selectivity or the like) when the distal end part 211 of the medical device body 210 is bent and is made to enter a branched body cavity can be obtained.

The distance 2L1 and the distance 2L2 may be the same. In this case, the smoothness of the pulling of the first operating line 241 and the second operating line 242 and the excellent selectivity when the distal end part 211 of the medical device body 210 is bent and is made to enter a branched body cavity can be obtained in a well-balanced manner.

Embodiment 2-3

Next, the medical device 2100 related to Embodiment 2-3 will be described with reference to FIGS. 32 to 38(c).

Figure 35:
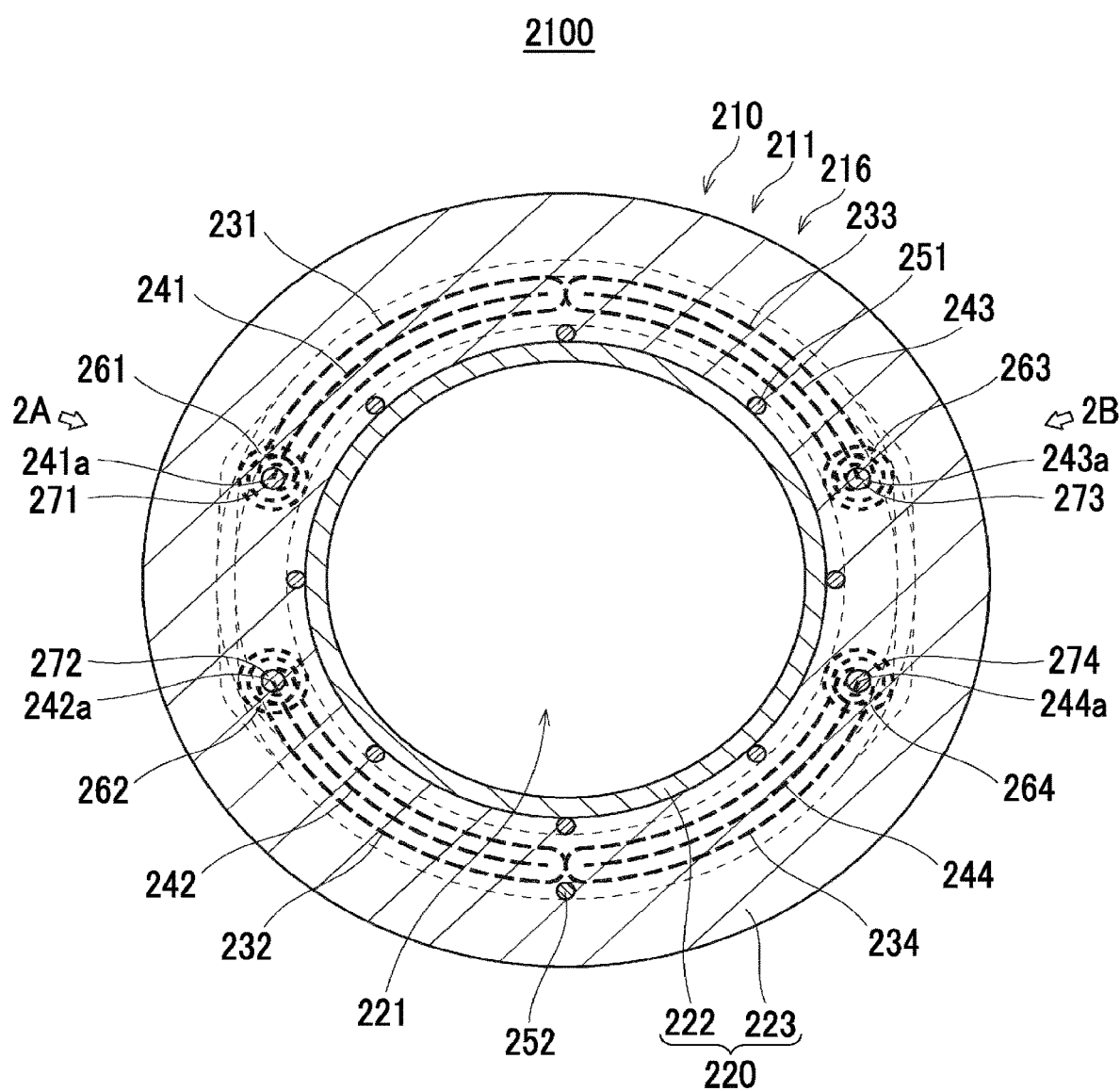
FIG. 35 is a cross-sectional view of the medical device body along line 2C-2C of FIG. 32.
Figure 36:
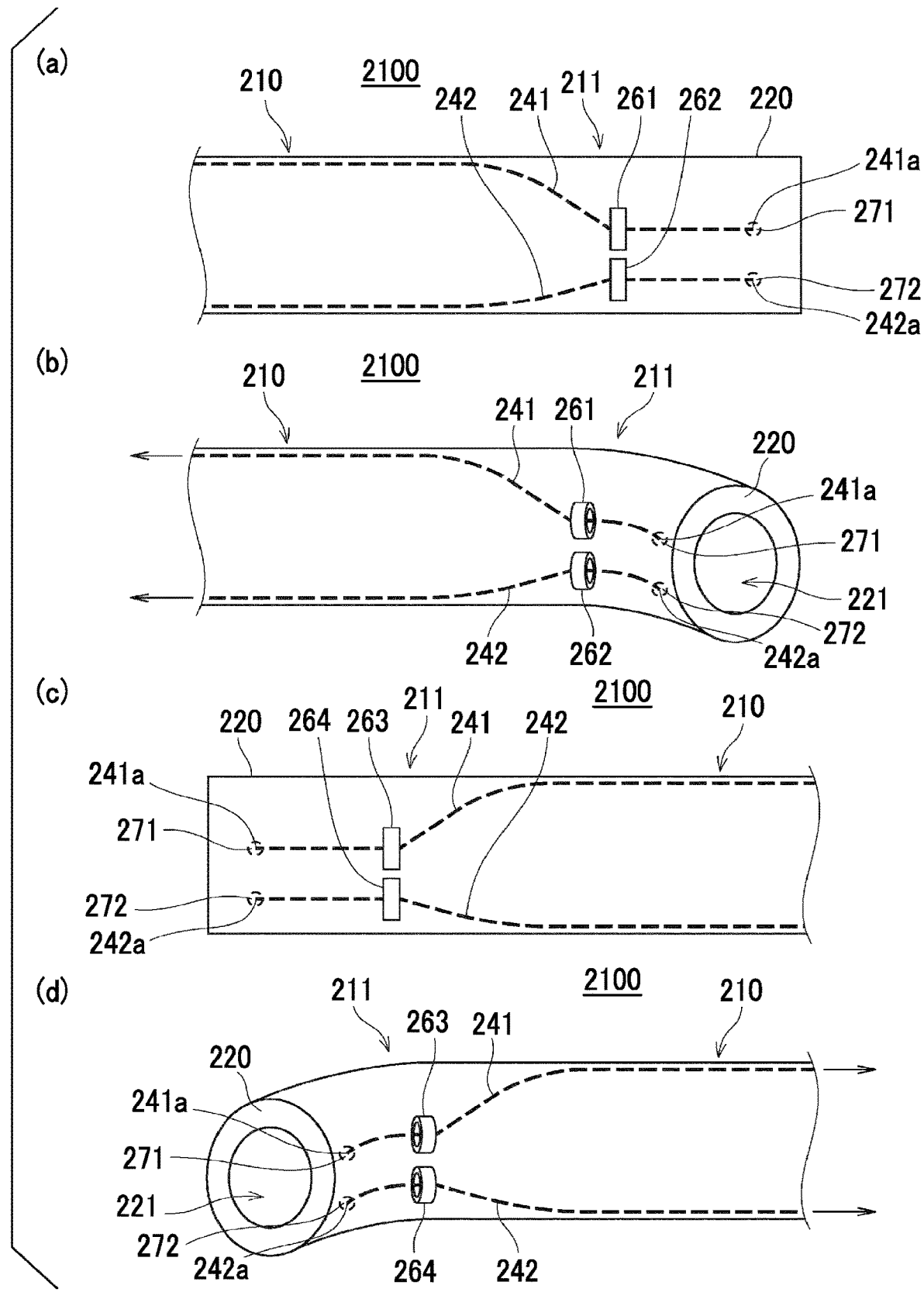
FIGS. 36(*a*), 36(*b*), 36(*c*), and 36(*d*) are schematic views for illustrating the bending motion of a distal end part of the medical device body of the medical device related to Embodiment 2-3.

FIGS. 36(a) and 36(b) are schematic views for illustrating the bending motion when the distal end part 211 of the medical device body 210 is seen in the direction of arrow 2A of FIG. 35, FIG. 36(a) illustrates the state before the bending, and FIG. 36(b) illustrates the bent state.

FIGS. 36(c) and 36(d) are schematic views for illustrating the bending motion when the distal end part 211 of the medical device body 210 is seen in a direction of arrow 2B of FIG. 35, FIG. 36(c) illustrates the state before the bending, and FIG. 36(d) illustrates the bent state.

In FIGS. 38(a), 38(b), and 38(c), the middle portion of the medical device body 210 in the longitudinal direction is broken and omitted. In the medical device body 210 illustrated in FIGS. 38(a), 38(b), and 38(c), a portion closer to the proximal end side than the omitted portion and a portion closer to the distal end side than the omitted portion have rotational phases around the axis of the medical device body 210 that are different from each other by 90 degrees.

The medical device 2100 related to the present embodiment is different from the medical device 2100 related to the above Embodiment 2-2 in terms of points to be described below, and is configured similarly to the medical device 2100 related to the above Embodiment 2-2 in terms of the other points.

In the case of the present embodiment, the medical device body 210 is configured to include a third hollow tube 233 and a fourth hollow tube 234 that are buried in the axial direction of the medical device body 210 and allow a third operating line 243 and a fourth operating line 244 to be respectively inserted therethrough.

The third operating line 243 and the fourth operating line 244 are respectively constituted of thin lines, such as metal or resin, similarly to the first operating line 241 and the second operating line 242.

The third hollow tube 233 and the fourth hollow tube 234 are respectively the same sublumen tubes as the first hollow tube 231 and the second hollow tube 232, and inner cavities of these sublumen tubes are sublumens. That is, the operating lines (the third operating line 243, the fourth operating line 244) are respectively inserted through the sublumens.

The internal diameters of the third hollow tube 233 and the fourth hollow tube 234 are smaller than the internal diameter of the lumen 221.

Figure 33:
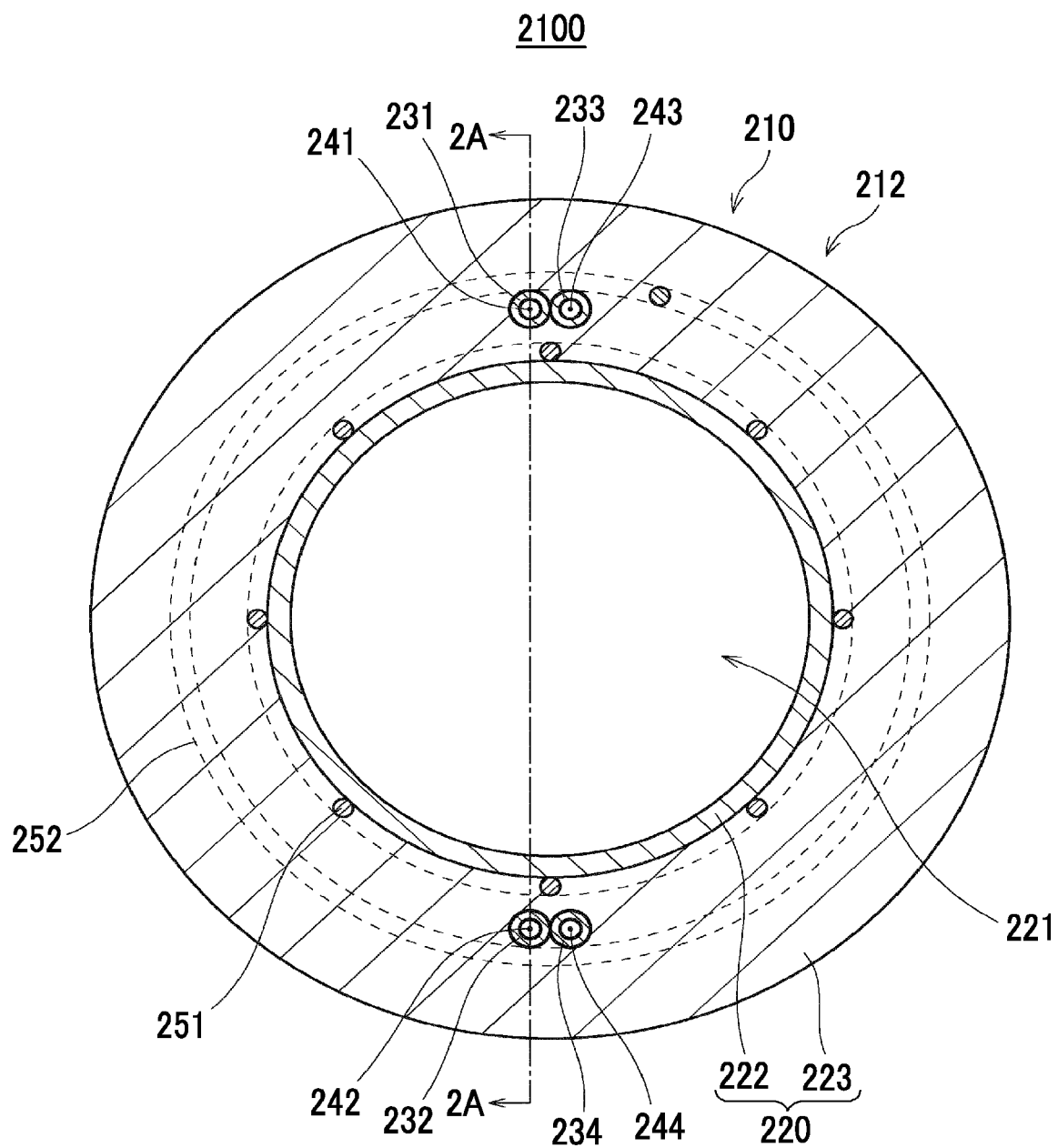
FIG. 33 is a cross-sectional view of the medical device body along line 2A-2A of FIG. 32.

In the case of the present embodiment, at the intermediate part 212 of the medical device body 210, the first hollow tube 231 and the third hollow tube 233 extend in parallel in abutment with or close to each other, and the second hollow tube 232 and the fourth hollow tube 234 extend in parallel in abutment with or close to each other (refer to FIG. 33).

Similarly, even at the proximal end part of the medical device body 210, the first hollow tube 231 and the third hollow tube 233 extend in parallel in abutment with or close to each other, and the second hollow tube 232 and the fourth hollow tube 234 extend in parallel in abutment with or close to each other.

At the intermediate part 212 and the proximal end part of the medical device body 210, the first hollow tube 231 and the second hollow tube 232 are spaced apart from each other at an angle of less than 180 degrees in the circumferential direction of the medical device body 210. For this reason, compared to Embodiment 2-1, the extraction of the sub-cores from the first hollow tube 231 and the second hollow tube 232 becomes easy.

Similarly to the intermediate part 212 and the proximal end part of the medical device body 210, the third hollow tube 233 and the fourth hollow tube 234 are spaced apart from each other at an angle of less than 180 degrees in the circumferential direction of the medical device body 210. For this reason, the extraction of the sub-cores from the third hollow tube 233 and the fourth hollow tube 234 becomes easy.

In the curved region 215 of the distal end part 211 of the medical device body 210, the third hollow tube 233 and the fourth hollow tube 234 are gradually curved so as to approach each other in the circumferential direction of the medical device body 210 toward the distal end side. Accordingly, the third operating line 243 within the third hollow tube 233 and the fourth operating line 244 within the fourth hollow tube 234 are gradually curved so as to approach each other in the circumferential direction of the medical device body 210 toward the distal end side.

The direction in which the third hollow tube 233 and the third operating line 243 are curved in the curved region 215 is a direction symmetrical to the direction in which the first hollow tube 231 and the first operating line 241 are curved.

Similarly, the direction in which the fourth hollow tube 234 and the fourth operating line 244 are curved in the curved region 215 is a direction symmetrical to the direction in which the second hollow tube 232 and the second operating line 242 are curved.

The respective hollow tubes (the first hollow tube 231, the second hollow tube 232, the third hollow tube 233, and the fourth hollow tube 234) do not intersect other hollow tubes. Additionally, the respective operating lines (the first operating line 241, the second operating line 242, the third operating line 243, and the fourth operating line 244) do not intersect other operating lines.

In the parallel region 216, similarly to the first operating line 241 and the second operating line 242 extending parallel to each other, the third operating line 243 and the fourth operating line 244 extend parallel to each other.

Additionally, in the parallel region 216, similarly to the first hollow tube 231 and the second hollow tube 232 extending parallel to each other, the third hollow tube 233 and the fourth hollow tube 234 extend parallel to each other.

The distal end 243a of the third operating line 243 protrudes from the distal end of the third hollow tube 233.

Similarly, the distal end 244a of the fourth operating line 244 protrudes from the distal end of the fourth hollow tube 234.

The distal end 243a of the third operating line 243 is fixed to the marker 270 by a third fixing part 273 that is, for example, spot-shaped solder (FIG. 35).

Similarly, the distal end 244a of the fourth operating line 244 is fixed to the marker 270 by a fourth fixing part 274 that is, for example, spot-shaped solder. The third fixing part 273 and the fourth fixing part 274 are disposed, for example, at an end part of the marker 270 on the proximal end side.

The third fixing part 273 and the fourth fixing part 274 are spaced apart from each other in the circumferential direction of the medical device body 210.

A region where the third fixing part 273 and the fourth fixing part 274 are disposed, and a region where the first fixing part 271 and the second fixing part 272 are disposed to face each other in the circumferential direction of the medical device body 210.

Figure 34:
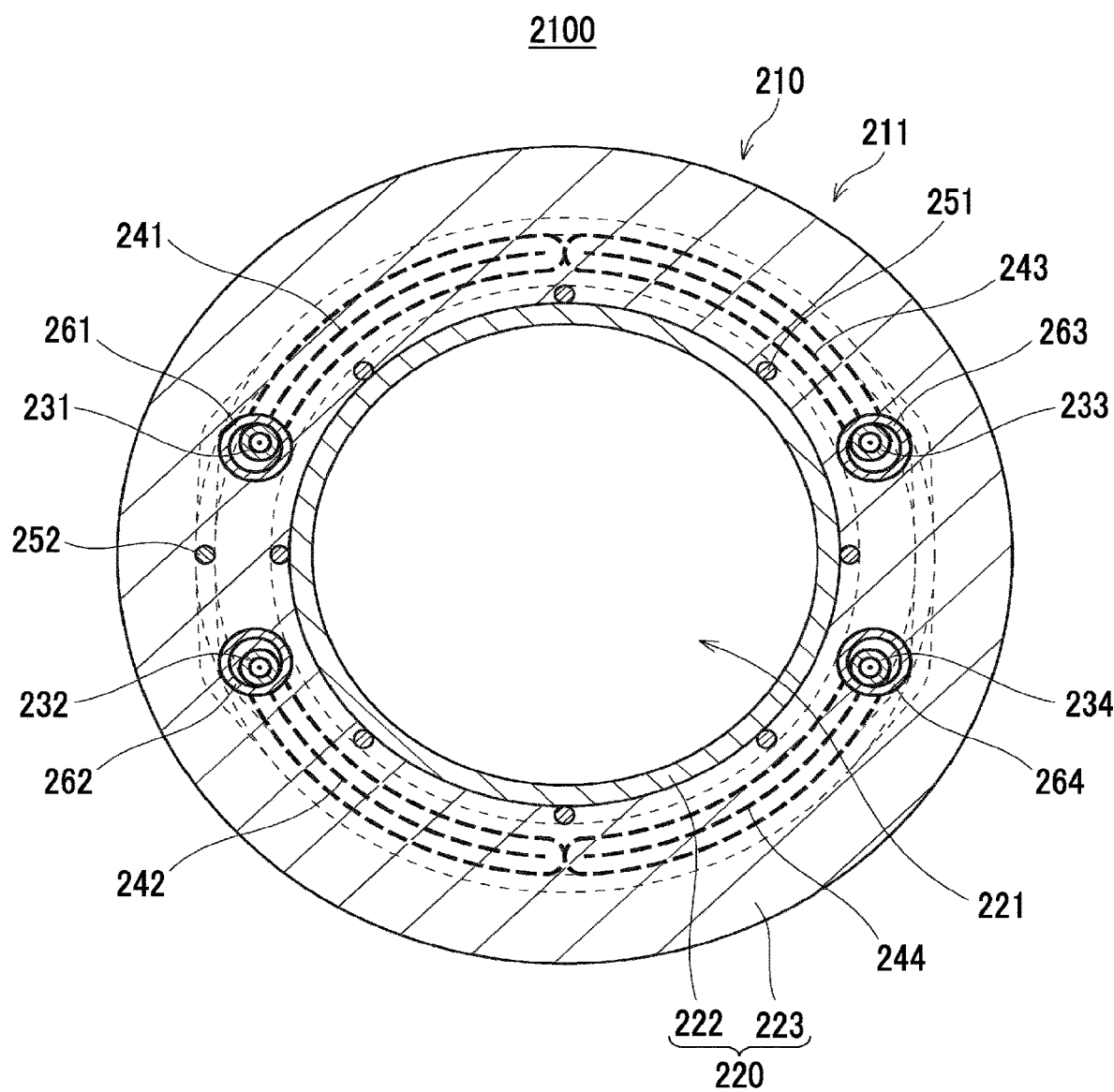
FIG. 34 is a cross-sectional view of the medical device body along line 2B-2B of FIG. 32.

As illustrated in FIG. 34, in the case of the present embodiment, the medical device 2100 includes a third annular member 263 and a fourth annular member 264 buried in the resin tube 220 at the distal end part of the curved region 215. The third annular member 263 and the fourth annular member 264 are the same as those of the first annular member 261 and the second annular member 262.

The third hollow tube 233 is inserted through the third annular member 263, and the fourth hollow tube 234 is inserted through the fourth annular member 264.

As long as the third operating line 243 and the fourth operating line 244 are spaced apart from each other, the third annular member 263 and the fourth annular member 264 may be in contact with each other. In the case of the present embodiment, the third annular member 263 and the fourth annular member 264 are disposed so as to be spaced apart from each other in the circumferential direction of the medical device body 210.

A region where the third annular member 263 and the fourth annular member 264 are disposed, and a region where the first annular member 261 and the second annular member 262 are disposed to face each other in the circumferential direction of the medical device body 210.

Even in the case of the present embodiment, by pulling both of the first operating line 241 and the second operating line 242, the distal end part 211 of the medical device body 210 can be bent in one direction as illustrated in FIGS. 36(a) and 36(b).

Moreover, in the case of the present embodiment, by pulling both of the third operating line 243 and the fourth operating line 244, the distal end part 211 of the medical device body 210 can be bent in an opposite direction opposite to the above one direction as illustrated in FIGS. 36(c) and 36(d).

Figure 37:
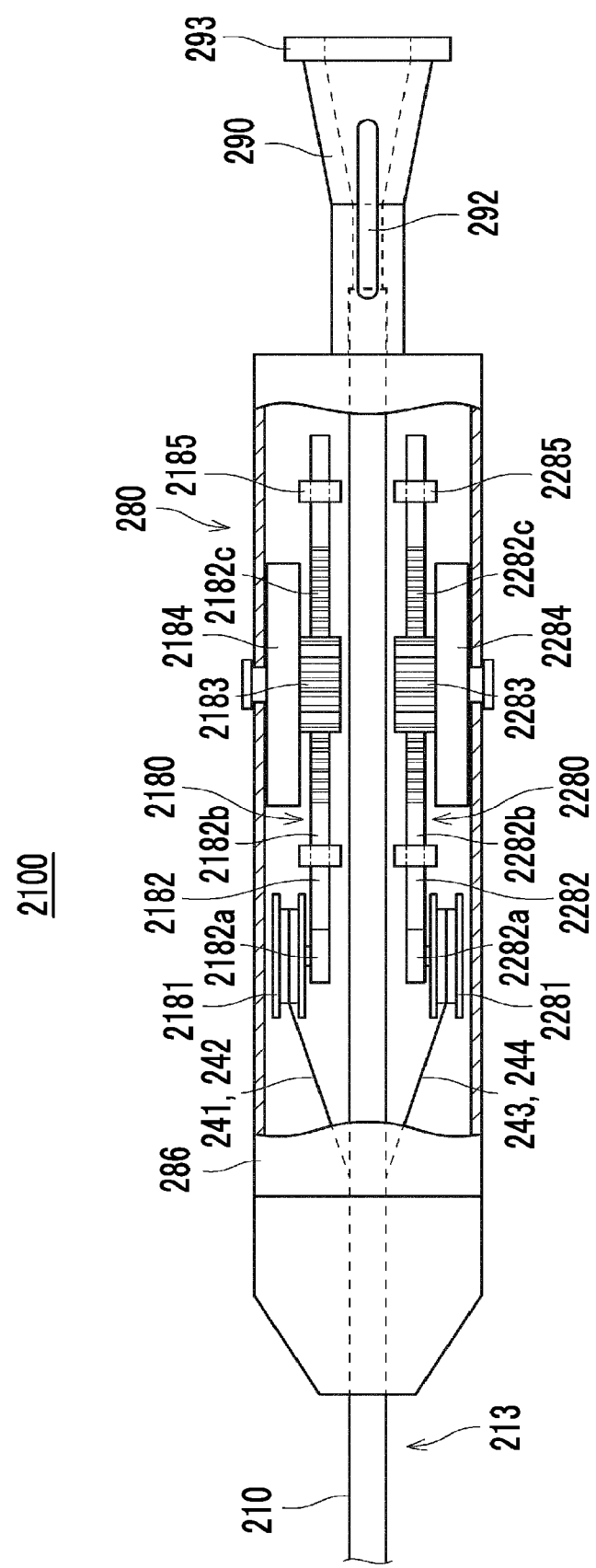
FIG. 37 is a side view illustrating a bending operating part and a portion in the vicinity thereof in the medical device related to Embodiment 2-3.
Figure 38:
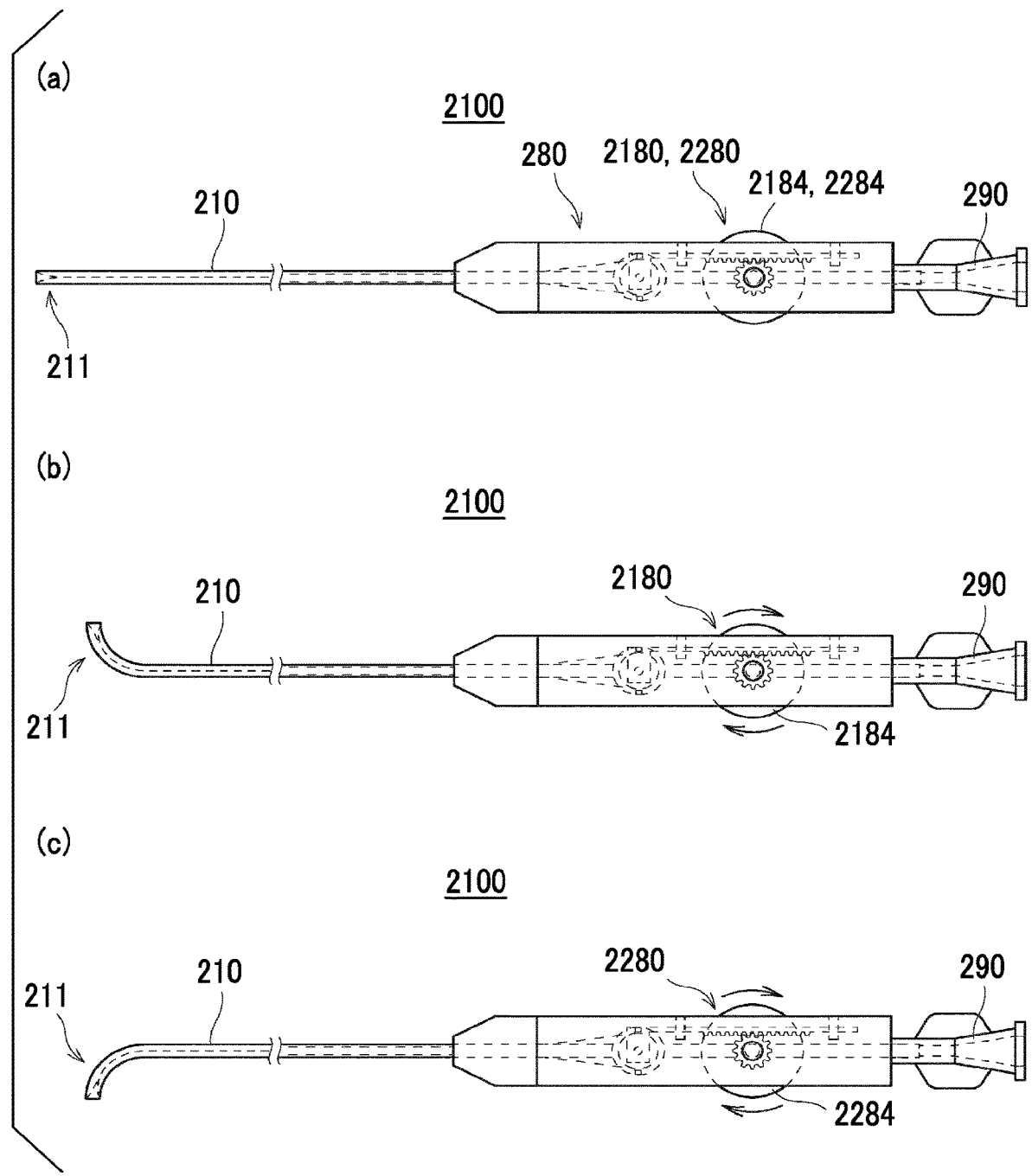
FIG. 38(*a*) is an overall view of the medical device related to Embodiment 2-3, FIG. 38(*b*) is an overall view illustrating a state where the distal end part of the medical device body of the medical device related to Embodiment 2-3 is bent to one side, and FIG. 38(*c*) is an overall view illustrating a state where the distal end part of the medical device body of the medical device related to Embodiment 2-3 is bent to the other side.

As illustrated in FIGS. 37 and 38(a), in the case of the present embodiment, the bending operating part 280 includes a first bending operating part 2180 for performing the bending operation of the distal end part 211 of the medical device body 210 by pulling the first operating line 241 and the second operating line 242, and a second bending operating part 2280 for performing the bending operation of the distal end part 211 of the medical device body 210 by pulling the third operating line 243 and the fourth operating line 244.

The first bending operating part 2180 includes a first rotating member 2181, a first forward/backward movable member 2182, a first pinion 2183, a first dial operating part 2184, and a first guide 2185. The first rotating member 2181, the first forward/backward movable member 2182, the first pinion 2183, the first dial operating part 2184, and the first guide 2185 are respectively equivalent to the rotating member 281, the forward/backward movable member 282, the pinion 283, the dial operating part 284, and the guide 285 that are described in Embodiment 2-1.

Hence, the first forward/backward movable member 2182 includes a first holding part 2182a, a first rod-shaped part 2182b, and a first rack part 2182c that are respectively equivalent to the holding part 282a, the rod-shaped part 282b, and the rack part 282c.

In Embodiment 2-1, similarly to the first operating line 241 and the second operating line 242 being wound around and fixed to the rotating member 281, the first operating line 241 and the second operating line 242 are wound around and fixed to the first rotating member 2181.

The second bending operating part 2280 includes a second rotating member 2281, a second forward/backward movable member 2282, a second pinion 2283, a second dial operating part 2284, and a second guide 2285. The second rotating member 2281, the second forward/backward movable member 2282, the second pinion 2283, the second dial operating part 2284, and the second guide 2285 are the same as the first rotating member 2181, the first forward/backward movable member 2182, the first pinion 2183, the first dial operating part 2184, and the first guide 2185. The second forward/backward movable member 2282 includes the second holding part 2282a, the second rod-shaped part 2282b, and the second rack part 2282c that are respectively the same as the first holding part 2182a, the first rod-shaped part 2182b, and the first rack part 2182c.

Similarly to the first operating line 241 and the second operating line 242 being wound around and fixed to the first rotating member 2181, the third operating line 243 and the fourth operating line 244 are wound around and fixed to the second rotating member 2281.

For example, the second bending operating part 2280 is disposed vertically symmetrically with respect to the first bending operating part 2180 in FIG. 37.

In the case of the present embodiment, by rotating the first dial operating part 2184 to move the first forward/backward movable member 2182 and the first rotating member 2181 backward, the first operating line 241 and the second operating line 242 can be pulled to bend the distal end part 211 of the medical device body 210 in one direction (FIG. 38(b)).

Additionally, by rotating the second dial operating part 2284 to move the second forward/backward movable member 2282 and the second rotating member 2281, the third operating line 243 and the fourth operating line 244 can be pulled to bend the distal end part 211 of the medical device body 210 in the direction opposite respect to the above one direction (FIG. 38(c)).

In this way, in the case of the present embodiment, the medical device 2100 includes the second bending operating part 2280 for performing the bending operation of the distal end part 211 of the medical device body 210 in a direction different from the direction of the bending of the distal end part 211 of the medical device body 210 by the pulling of the first operating line 241 and the second operating line 242, by pulling the third operating line 243 and the fourth operating line 244.

At the intermediate part 212 and the proximal end part 213 in the axial direction of the medical device body 210, the third operating line 243 and the fourth operating line 244 extend in parallel so as to be spaced apart from each other in the circumferential direction of the medical device body 210, and in the curved region 215, the third operating line 243 and the fourth operating line 244 are gradually curved so as to approach each other in the circumferential direction of the medical device body 210 toward the distal end sides, and the distal end 243a of the third operating line 243 and the distal end 244a of the fourth operating line 244 are spaced apart from each other in the circumferential direction of the medical device body 210, and are fixed to the medical device body 210.

Additionally, the third operating line 243 and the fourth operating line 244 are pulled at a time by the operation on the second bending operating part 2280.

Embodiment 2-4

Next, the medical device 2100 related to Embodiment 2-4 will be described with reference to FIGS. 39(a) and 39(b).

The medical device 2100 related to the present embodiment is different from the medical device 2100 related to the above Embodiment 2-1 in terms of points to be described below, and is configured similarly to the medical device 2100 related to the above Embodiment 2-1 in terms of the other points.

In the case of the present embodiment, an easily bendable part 2110 in which the flexibility of the medical device body 210 is locally high is formed in a region between the first operating line 241 and the second operating line 242 or a region located opposite to the region with respect to the axis of the medical device body 210, in the circumferential direction of the distal end part 211 of the medical device body 210.

Accordingly, since the flexibility of the distal end part 211 is improved, the tension acting on the first operating line 241 and the second operating line 242 during the bending operation can be reduced. Hence, the occurrence of the phenomenon in which the medical device body 210 rotates around the axis such that the first operating line 241 or the second operating line 242 tends to take a shortcut can be suppressed.

Figure 39:
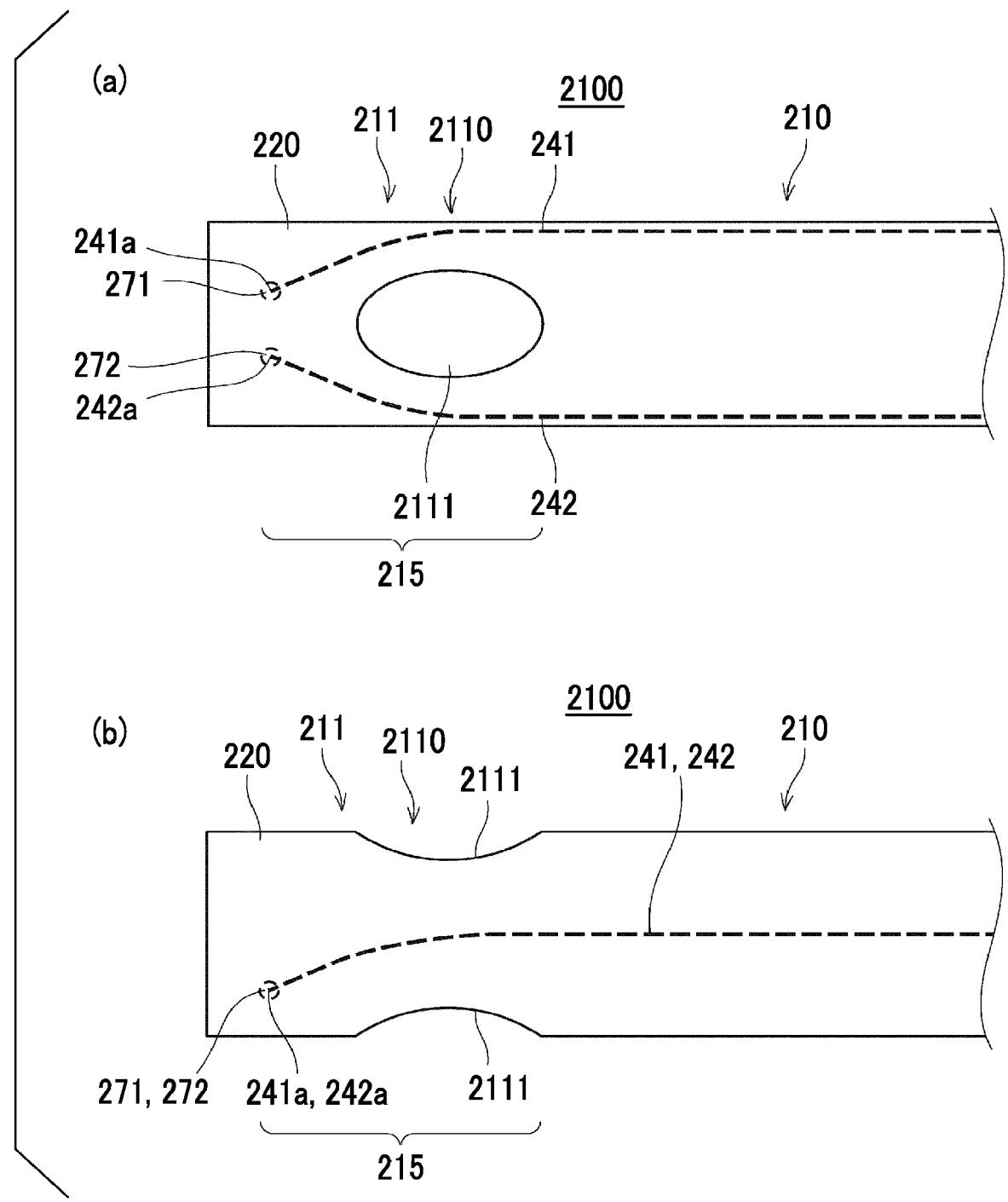
FIGS. 39(*a*) and 39(*b*) are schematic views of a distal end part of a medical device body of a medical device related to Embodiment 2-4, and in these drawings, FIG. 39(*a*) is a plan view, and FIG. 39(*b*) is a side view.

More specifically, as illustrated in FIG. 39(b), the easily bendable parts 2110 are formed both in the region between the first operating line 241 and the second operating line 242 and the region located opposite to the region with respect to the axis of the medical device body 210, in the circumferential direction of the distal end part 211 of the medical device body 210.

Accordingly, the flexibility of the distal end part 211 is further improved.

The easily bendable part 2110 is configured to include a notched part 2111 formed on an outer surface side of the medical device body 210.

The notched part 2111 can be formed in, for example, a shape gouged out in an arc as illustrated in FIG. 39(b).

Accordingly, the distal end part 211 can be more steeply bent.

Embodiment 2-5

Next, the medical device 2100 related to Embodiment 2-5 will be described with reference to FIGS. 40(a) and 40(b).

The medical device 2100 related to the present embodiment is different from the medical device 2100 related to the above Embodiment 2-1 in terms of points to be described below, and is configured similarly to the medical device 2100 related to the above Embodiment 2-1 in terms of the other points.

In the case of the present embodiment, an easily bendable part 2110 in which the flexibility of the medical device body 210 is locally high is formed in the region between the first operating line 241 and the second operating line 242 or the region located opposite to the region with respect to the axis of the medical device body 210, in the circumferential direction of the distal end part 211 of the medical device body 210.

Accordingly, since the flexibility of the distal end part 211 is improved, the tension acting on the first operating line 241 and the second operating line 242 during the bending operation can be reduced. Hence, the occurrence of the phenomenon in which the medical device body 210 rotates around the axis such that the first operating line 241 or the second operating line 242 tends to take a shortcut can be suppressed.

Figure 40:
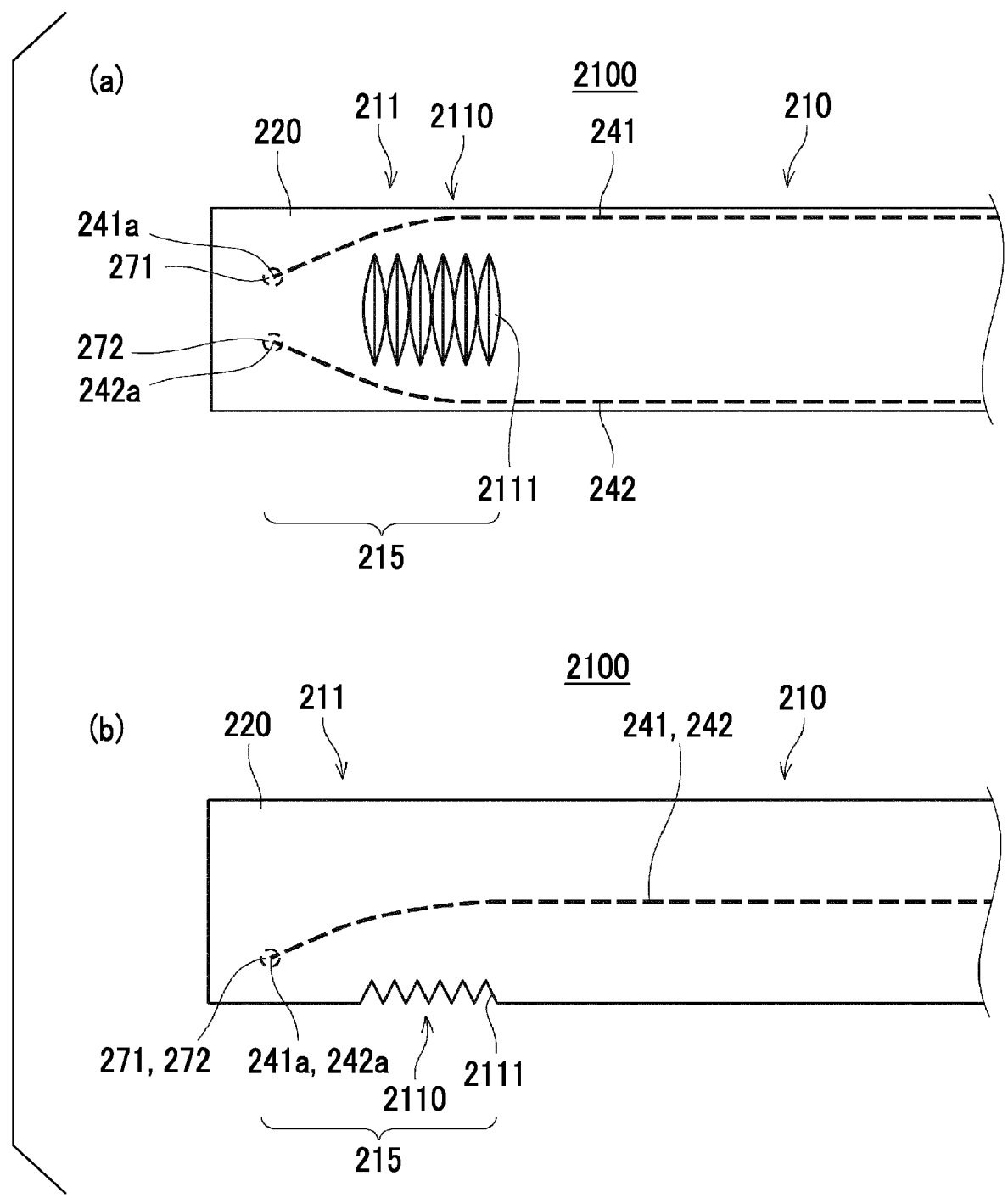
FIGS. 40(*a*) and 40(*b*) are schematic views of a distal end part of a medical device body of a medical device related to Embodiment 2-5, and in these drawings, FIG. 40(*a*) is a plan view, and FIG. 40(*b*) is a side view.

More specifically, as illustrated in FIG. 40(*b*), the easily bendable part 2110 is formed in the region between the first operating line 241 and the second operating line 242 in the circumferential direction of the distal end part 211 of the medical device body 210, and the easily bendable part 2110 is not formed in the region located opposite to the region with respect to the axis of the medical device body 210.

However, the easily bendable parts 2110 may be formed both in the region between the first operating line 241 and the second operating line 242 and the region located opposite to the region with respect to the axis of the medical device body 210, in the circumferential direction of the distal end part 211 of the medical device body 210.

The easily bendable part 2110 is configured to include the notched part 2111 formed on the outer surface side of the medical device body 210.

In the case of the present embodiment, the medical device body 210 has a plurality of the notched parts 2111 disposed adjacent to each other in the axial direction of the medical device body 210. The notched parts 2111 are elongated in the circumferential direction of the medical device body 210, and the sectional shape thereof is a wedge shape.

In the case of the present embodiment, the distal end part 211 of the medical device body 210 is easily bent in the initial stage of the bending. However, if a certain amount of bending angle is reached, wedge-shaped inclined surfaces come in contact with each other, so that further bending becomes difficult (if a certain amount of bending angle is reached, rigidity become high).

For this reason, since the distal end part 211 of the medical device body 210 has excellent deformation resistance against compression in the axial direction when being pushed into a body cavity, the blood vessel selectivity of the medical device 2100 is excellent.

Although the respective embodiments have been described above with reference to the drawings, these are examples of the invention, and various configurations other than the above can also be adopted.

An example in which the rotating mechanism of the bending operating part 280 is the dial operating part 284 has been described in the above Embodiment 2-1. However, the rotating mechanism of the bending operating part 280 may be others (for example, a rotary lever or the like) than the dial operating part 284.

Additionally, an example in which the conversion mechanism of the bending operating part 280 is configured to include the rack (rack part 282*c*) and the pinion 283 has been described in the above Embodiment 2-1. However, the bending operating part 280 may be configured to include other conversion mechanisms (for example, a cam, a link mechanism, a pin, a guide with a groove, or the like).

The same applies to the other embodiments.

Additionally, an example in which the proximal end part of the first operating line 241 and the proximal end part of the second operating line 242 are individually fixed to the bending operating part 280 has been described in the above respective embodiments. However, the proximal end of the first operating line 241 and the proximal end of the second operating line 242 may be connected to each other, and may be looped (looped in a portion engaged with the rotating member 281) in the bending operating part 280.

Similarly, an example in which a proximal end part of the third operating line 243 and a proximal end part of the fourth operating line 244 are individually fixed to the second bending operating part 2280 has been described above. However, a proximal end of the third operating line 243 and a proximal end of the fourth operating line 244 may be connected to each other, and may be looped (for example, looped in the portion engaged with the second rotating member 2281) in the second bending operating part 2280.

Additionally, the above respective embodiments can be appropriately combined without departing from the spirit of the invention.

The present embodiment includes the following technical ideas.

(1) A medical device including an elongated medical device body;

a first operating line and a second operating line that are inserted in an axial direction of the medical device body; and a bending operating part for performing a bending operation of a distal end part of the medical device body by pulling the first operating line and the second operating line, in which at an intermediate part and a proximal end part in the axial direction of the medical device body, the first operating line and the second operating line extending in parallel so as to be spaced apart from each other in a circumferential direction of the medical device body, and at a distal end part in the axial direction of the medical device body, the first operating line and the second operating line being gradually curved so as to approach each other in the circumferential direction of the medical device body toward a distal end side and joined together.

(2) The medical device according to (1) in which the first operating line and the second operating line are pulled at a time by an operation on the bending operating part.

(3) The medical device according to (1) or (2) in which distal ends of the first operating line and the second operating line are coupled to each other.

(4) The medical device according to any one of (1) to (3) in which at the intermediate part and the proximal end part in the axial direction of the medical device body, the first operating line and the second operating line are disposed at positions that face each other in the circumferential direction of the medical device body.

(5) The medical device according to any one of (1) to (4) in which the medical device body is configured to include a resin tube having a lumen, and a first hollow tube and a second hollow tube that are buried in the resin tube and allows the first operating line and the second operating line to be respectively inserted therethrough, and at the distal end part in the axial direction of the medical device body, the first hollow tube and the second hollow tube are gradually curved so as to approach each other in the circumferential direction of the medical device body toward the distal end side.

(6) The medical device according to any one of (1) to (5) in which the bending operating part is configured to include a rotating member that is rotatably supported and is engaged with the first operating line and the second operating line and to which a proximal end part of the first operating line and a proximal end part of the second operating line are fixed, and a moving mechanism that moves the rotating member in a pulling direction in which the first operating line and the second operating line are pulled, and an opposite direction opposite to the pulling direction.

(7) The medical device according to any one of (1) to (6) in which an easily bendable part in which flexibility of the medical device body is locally high is formed in a region between the first operating line and the second operating line or a region located opposite to the region with respect to an axis of the medical device body, in the circumferential direction of the distal end part of the medical device body.

(8) The medical device according to (7) in which the easily bendable part is configured to include a notched part formed on an outer surface side of the medical device body.

(9) The medical device according to any one of (1) to (8) in which the medical device body is configured to include a resin tube having a lumen, the first operating line and the second operating line are inserted around the lumen of the resin tube, the first operating line and the second operating line are close to each other at a distance smaller than a thickness of the resin tube, at a distal end of a curved region where the first operating line and the second operating line are gradually curved so as to approach each other in the circumferential direction of the medical device body toward the distal end side, and a parallel region where the first operating line and the second operating line extend in parallel close to each other is formed between a distal end of the curved region, and distal ends of the first operating line and the second operating line.

(10) The medical device according to (9) in which a distance from the distal end of the curved region to the distal ends of the first operating line and the second operating line is longer than a distance from a proximal end of the curved region to the distal end thereof in the axial direction of the medical device body.

(11) The medical device according to (9) in which a distance from a proximal end of the curved region to the distal end thereof is longer than a distance from the distal end of the curved region to the distal ends of the first operating line and the second operating line in the axial direction of the medical device body.

(12) The medical device according to any one of (9) to (11) further including an annular member buried in the resin tube at a distal end part of the curved region, in which the annular member being configured to have a rigidity higher than the resin tube, and have an external diameter smaller than the thickness of the resin tube, and the first operating line and the second operating line being inserted through the annular member.

(13) The medical device according to (12) in which the medical device body is configured to include a first hollow tube and a second hollow tube that are buried in the resin tube and allows the first operating line and the second operating line to be respectively inserted therethrough, the first hollow tube and the second hollow tube are inserted through the annular member, and in the curved region, the first hollow tube and the second hollow tube are gradually curved so as to approach each other in the circumferential direction of the medical device body toward the distal end side.

(14) The medical device according to any one of (1) to (13) further including a third operating line and a fourth operating line that are inserted in the axial direction of the medical device body; and a second bending operating part for performing a bending operation of the distal end part of the medical device body in a direction different from a direction of the bending of the distal end part of the medical device body by the pulling of the first operating line and the second operating line, by pulling the third operating line and the fourth operating line, in which at the intermediate part and the proximal end part in the axial direction of the medical device body, the third operating line and the fourth operating line extending in parallel so as to be spaced apart from each other in the circumferential direction of the medical device body, and at the distal end part in the axial direction of the medical device body, the third operating line and the fourth operating line being gradually curved so as to approach each other in the circumferential direction of the medical device body toward the distal end side and joined together.

(15) The medical device according to (14) in which the third operating line and the fourth operating line are pulled at a time by an operation on the second bending operating part.

(16) A medical device including an elongated medical device body configured to include an elongated resin tube having a lumen, and a first hollow tube and a second hollow tube that are buried in an axial direction of the resin tube and allows the first operating line and the second operating line to be respectively inserted therethrough, and a bending operating part for performing a bending operation of a distal end part of the medical device body by pulling the first operating line and the second operating line, in which at an intermediate part and a proximal end part in the axial direction of the medical device body, the first operating line and the second operating line extending in parallel so as to be spaced apart from each other in a circumferential direction of the medical device body, at a distal end part in the axial direction of the medical device body, a curved region where the first operating line and the second operating line are gradually curved so as to approach each other in the circumferential direction of the medical device body toward a distal end side being formed, and a distal end of the first operating line and a distal end of the second operating line being spaced apart from each other in the circumferential direction of the medical device body, and are fixed to the medical device body.

(17) The medical device according to (16) in which the first operating line and the second operating line are pulled at a time by an operation on the bending operating part.

(18) The medical device according to (16) or (17) in which a parallel region where the first operating line and the second operating line extend in parallel closer to each other than distances therebetween at the intermediate part and the proximal end part on a distal end side of the curved region is formed at the distal end part in the axial direction of the medical device body.

(19) The medical device according to (18) in which a distance from the distal end of the curved region to the distal ends of the first operating line and the second operating line is longer than a distance from a proximal end of the curved region to the distal end thereof in the axial direction of the medical device body.

(20) The medical device according to (19) in which a distance from a proximal end of the curved region to the distal end thereof is longer than a distance from the distal end of the curved region to the distal ends of the first operating line and the second operating line in the axial direction of the medical device body.

(21) The medical device according to any one of (18) to (20) further including an annular member buried in the resin tube at a distal end part of the curved region, in which the annular member being configured to have a rigidity higher than the resin tube, and have an external diameter smaller than the thickness of the resin tube, and the first operating line and the second operating line being inserted through the annular member.

(22) The medical device according to (21) in which the first hollow tube and the second hollow tube are inserted through the annular member, and in the curved region, the first hollow tube and the second hollow tube are gradually curved so as to approach each other in the circumferential direction of the medical device body toward the distal end side.

(23) The medical device according to any one of (16) to (22) in which at the intermediate part and the proximal end part in the axial direction of the medical device body, the first operating line and the second operating line are disposed at positions that face each other in the circumferential direction of the medical device body.

(24) The medical device according to any one of (16) to (23) in which in the curved region, the first hollow tube and the second hollow tube are gradually curved so as to approach each other in the circumferential direction of the medical device body toward the distal end side.

(25) The medical device according to any one of (16) to (24) in which the bending operating part is configured to include a rotating member that is rotatably supported and is engaged with the first operating line and the second operating line and to which a proximal end part of the first operating line and a proximal end part of the second operating line are fixed, and a moving mechanism that moves the rotating member in a pulling direction in which the first operating line and the second operating line are pulled, and an opposite direction opposite to the pulling direction.

(26) The medical device according to any one of (16) to (25) in which an easily bendable part in which flexibility of the medical device body is locally high is formed in a region between the first operating line and the second operating line or a region located opposite to the region with respect to an axis of the medical device body, in the circumferential direction of the distal end part of the medical device body.

(27) The medical device according to (26) in which the easily bendable part is configured to include a notched part formed on an outer surface side of the medical device body.

(28) The medical device according to any one of (16) to (27) in which the medical device body is configured to include a third hollow tube and a fourth hollow tube that are buried in the axial direction of the medical device body and allow a third operating line and a fourth operating line to be respectively inserted therethrough, the medical device further includes a second bending operating part for performing a bending operation of the distal end part of the medical device body in a direction different from a direction of the bending of the distal end part of the medical device body by the pulling of the first operating line and the second operating line, by pulling the third operating line and the fourth operating line, at an intermediate part and a proximal end part in the axial direction of the medical device body, the third operating line and the fourth operating line extend in parallel so as to be spaced apart from each other in the circumferential direction of the medical device body, in the curved region, the third operating line and the fourth operating line are gradually curved so as to approach each other in the circumferential direction of the medical device body toward the distal end side, and a distal end of the third operating line and a distal end of the fourth operating line are spaced apart from each other in the circumferential direction of the medical device body, and are fixed to the medical device body.

(29) The medical device according to (28) in which the third operating line and the fourth operating line are pulled at a time by an operation on the second bending operating part.

INDUSTRIAL APPLICABILITY

The medical device of a structure capable of more reliably bending the distal end part in a desired direction can be provided.

REFERENCE SIGNS LIST

110: medical device body
111: distal end part
112: intermediate part
113: proximal end part
115: curved region
115a: proximal end position
115b: distal end position
116: parallel region
120: resin tube
121: lumen
122: inner layer
123: outer layer
131: first hollow tube
131a: distal end
132: second hollow tube
132a: distal end
133: third hollow tube
134: fourth hollow tube
141: first operating line
141a: distal end
142: second operating line
142a: distal end
143: third operating line
143a: distal end
144: fourth operating line
144a: distal end
151: braid layer
152: winding wire
160: annular member
161: first annular member
162: second annular member
170: marker
171: first fixing part
172: second fixing part
173: third fixing part
174: fourth fixing part
180: bending operating part
181: rotating member
181a: first fixing part
181b: second fixing part 182: forward/backward movable member (moving mechanism)
182a: holding part
182b: rod-shaped part
182c: rack part
183: pinion (moving mechanism)
184: dial operating part
185: guide
186: housing
1180: first bending operating part
1181: first rotating member
1182: first forward/backward movable member (moving mechanism)
1182a: first holding part
1182b: first rod-shaped part
1182c: first rack part
1183: first pinion (moving mechanism)
1184: first dial operating part
1185: first guide
1280: second bending operating part
1281: second rotating member
1282: second forward/backward movable member (moving mechanism)
1282a: second holding part
1282b: second rod-shaped part
1282c: second rack part
1283: second pinion (moving mechanism)
1284: second dial operating part
1285: second guide
190: hub
192: wing part
193: coupling part
1100: medical device
1110: easily bendable part
1111: notched part
210: medical device body
211: distal end part
212: intermediate part
213: proximal end part
215: curved region
215a: proximal end position
215b: distal end position
216: parallel region
220: resin tube
221: lumen
222: inner layer
223: outer layer
231: first hollow tube
231a: distal end
232: second hollow tube
232a: distal end
233: third hollow tube
234: fourth hollow tube
241: first operating line
241a: distal end
242: second operating line
242a: distal end
243: third operating line
243a: distal end
244: fourth operating line
244a: distal end
251: braid layer
252: winding wire
261: first annular member
262: second annular member
263: third annular member
264: fourth annular member
270: marker
271: first fixing part
272: second fixing part
273: third fixing part
274: fourth fixing part
280: bending operating part
281: rotating member
281a: first fixing part
281b: second fixing part
282: forward/backward movable member (moving mechanism)
282a: holding part
282h: rod-shaped part
282c: rack part
283: pinion (moving mechanism)
284: dial operating part
285: guide
286: housing
2180: first bending operating part
2181: first rotating member
2182: first forward/backward movable member (moving mechanism)
2182a: first holding part
2182b: first rod-shaped part
2182c: first rack part
2183: first pinion (moving mechanism)
2184: first dial operating part
2185: first guide
2280: second bending operating part
2281: second rotating member
2282: second forward/backward movable member (moving mechanism)
2282a: second holding part
2282b: second rod-shaped part
2282c: second rack part
2283: second pinion (moving mechanism)
2284: second dial operating part
2285: second Guide
290: hub
292: wing part
293: coupling part
2100: medical device
2110: easily bendable part
2111: notched part

The invention claimed is:

1. A medical device, comprising:
a medical device body having an elongated shape and comprising a resin tube having a lumen;
a plurality of operating lines comprising a first operating line and a second operating line that are inserted in the resin tube around the lumen of the resin tube in an axial direction of the medical device body; and
a bending operating part comprising a device that pulls the first operating line and the second operating line such that a bending operation of a distal end part of the medical device body is performed, wherein the medical device body has an intermediate part and a proximal end part in the axial direction of the medical device body such that the first and second operating lines extend in parallel in the intermediate and proximal end parts and are spaced apart from each other in a circumferential direction of the medical device body, the medical device body has the distal end part in the axial direction of the medical device body such that the first and second operating lines are gradually curved and approach each other in the circumferential direction toward a distal end side in the distal end part, the medical device body has a curved region and a parallel region such that in the curved region, the first and second operating lines gradually curve and approach each other in the circumferential direction toward the distal end side and have a distance smaller than a thickness of the resin tube at a distal end of the curved region, such that in the parallel region, the first and second operating lines extend in parallel to each other between the distal end of the curved region and distal ends of the first and second operating lines, and such that a distance from a proximal end of the curved region to the distal end of the curved region is longer than a distance from the distal end of the curved region to the distal ends of the first and second operating lines in the axial direction of the medical device body, and the medical device body comprises a first hollow tube and a second hollow tube buried in the resin tube and configured such that the first operating line and the second operating line are inserted into the first hollow tube and the second hollow tube respectively and that the first hollow tube and the second hollow tube are gradually curved and approach each other in the circumferential direction of the medical device body toward the distal end side and extend in parallel in abutment with or close to each other in the parallel region.

2. The medical device according to claim 1, wherein the first operating line and the second operating line are pulled at a time by an operation on the device of the bending operating part.

3. The medical device according to claim 1, wherein distal ends of the first operating line and the second operating line are coupled to each other.

4. The medical device according to claim 3, further comprising:
an annular member buried in the resin tube at a distal end part of the curved region,
wherein the annular member has a rigidity higher than a rigidity of the resin tube, and has an external diameter smaller than the thickness of the resin tube, and the first operating line and the second operating line are inserted through the annular member.

5. The medical device according to claim 4, wherein the medical device body is configured such that the first operating line and the second operating line are inserted through the annular member and are gradually curved and approach each other in the circumferential direction of the medical device body toward the distal end side in the curved region.

6. The medical device according to claim 1, wherein at the intermediate part and the proximal end part in the axial direction of the medical device body, the first operating line and the second operating line are disposed at positions that face each other in the circumferential direction of the medical device body.

7. The medical device according to claim 1, wherein the device of the bending operating part comprises a rotating member that is rotatably supported and is engaged with the first operating line and the second operating line and to which a proximal end part of the first operating line and a proximal end part of the second operating line are fixed, and a moving mechanism that moves the rotating member in a pulling direction in which the first operating line and the second operating line are pulled, and an opposite direction opposite to the pulling direction.

8. The medical device according to claim 1, wherein the medical device body has a bendable part in which flexibility of the medical device body is locally high in a region between the first operating line and the second operating line or a region located opposite to the region between the first operating line and the second operating line with respect to an axis of the medical device body, in the circumferential direction of the distal end part of the medical device body.

9. The medical device according to claim 8, wherein the bendable part comprises a notched part formed on an outer surface side of the medical device body.

10. The medical device according to claim 1, further comprising:
an annular member buried in the resin tube at a distal end part of the curved region,
wherein the annular member has a rigidity higher than a rigidity of the resin tube, and has an external diameter smaller than the thickness of the resin tube, and the first operating line and the second operating line are inserted through the annular member.

11. The medical device according to claim 10, wherein the medical device body is configured such that the first operating line and the second operating line are inserted through the annular member and are gradually curved and approach each other in the circumferential direction of the medical device body toward the distal end side in the curved region.

12. The medical device according to claim 1, further comprising:
a second bending operating part comprising a device,
wherein the plurality of operating lines includes a third operating line and a fourth operating line that are inserted in the axial direction of the medical device body, the device of the second bending operating part pulls the third operating line and the fourth operating line such that a second bending operation of the distal end part of the medical device body is performed in a direction different from a direction of the bending of the distal end part of the medical device body in the bending operation, at the intermediate part and the proximal end part in the axial direction of the medical device body, the third operating line and the fourth operating line extend in parallel such that the third operating line and the fourth operating line are spaced apart from each other in the circumferential direction of the medical device body, and at the distal end part in the axial direction of the medical device body, the third operating line and the fourth operating line are gradually curved such that the third operating line and the fourth operating line approach each other in the circumferential direction of the medical device body toward the distal end side and joined together.

13. The medical device according to claim 12, wherein the third operating line and the fourth operating line are pulled at a time by an operation on the second bending operating part.

14. A medical device, comprising:
a medical device body having an elongated shape and comprising a resin tube having a lumen; and
a bending operating part comprising a device that performs a bending operation of a distal end part of the medical device body,
wherein the medical device body includes a first hollow tube and a second hollow tube that are buried in an axial direction of the resin tube and configured such that a first operating line and a second operating line are inserted through the first hollow tube and the second hollow tube, respectively, the device of the bending operating part pulls the first and second operating lines such that the bending operation is performed, the medical device body has an intermediate part and a proximal end part in the axial direction of the medical device body such that the first and second operating lines extend in parallel and are spaced apart from each other in a circumferential direction of the medical device body, and the medical device body has a curved region in the distal end part in the axial direction of the medical device body such that in the curved region, a distal end of the first operating line and a distal end of the second operating line are fixed to the medical device body, that in the curved region, the first and second hollow tubes are gradually curved and approach each other in the circumferential direction toward a distal end side, and that in the curved region, distal ends of the first and second hollow tubes are terminated and spaced apart from each other in the circumferential direction.

15. The medical device according to claim 14, wherein the first operating line and the second operating line are pulled at a time by an operation on the bending operating part.

16. The medical device according to claim 14, wherein a parallel region where the first operating line and the second operating line extend in parallel closer to each other than distances therebetween at the intermediate part and the proximal end part on a distal end side of the curved region is formed at the distal end part in the axial direction of the medical device body.

17. The medical device according to claim 16, wherein a distance from the distal end of the curved region to the distal ends of the first operating line and the second operating line is longer than a distance from a proximal end of the curved region to the distal end thereof in the axial direction of the medical device body.

18. The medical device according to claim 17, wherein a distance from a proximal end of the curved region to the distal end thereof is longer than a distance from the distal end of the curved region to the distal ends of the first operating line and the second operating line in the axial direction of the medical device body.

19. The medical device according to claim 16, further comprising:
an annular member buried in the resin tube at a distal end part of the curved region,
wherein the annular member has a rigidity higher than a rigidity of the resin tube, and has an external diameter smaller than the thickness of the resin tube, and the first operating line and the second operating line are inserted through the annular member.

20. The medical device according to claim 19, wherein the first hollow tube and the second hollow tube are inserted through the annular member, and in the curved region, the first hollow tube and the second hollow tube are gradually curved such that the first hollow tube and the second hollow tube approach each other in the circumferential direction of the medical device body toward the distal end side.

21. The medical device according to claim 14, wherein at the intermediate part and the proximal end part in the axial direction of the medical device body, the first operating line and the second operating line are disposed at positions that face each other in the circumferential direction of the medical device body.

22. The medical device according to claim 14, wherein the device of the bending operating part comprises a rotating member that is rotatably supported and is engaged with the first operating line and the second operating line and to which a proximal end part of the first operating line and a proximal end part of the second operating line are fixed, and a moving mechanism that moves the rotating member in a pulling direction in which the first operating line and the second operating line are pulled, and an opposite direction opposite to the pulling direction.

23. The medical device according to claim 22, wherein the medical device body has a bendable part in which flexibility of the medical device body is locally high in a region between the first operating line and the second operating line or a region located opposite to the region between the first operating line and the second operating line with respect to an axis of the medical device body, in the circumferential direction of the distal end part of the medical device body.

24. The medical device according to claim 23, wherein the bendable part comprises a notched part formed on an outer surface side of the medical device body.

25. The medical device according to claim 14, wherein the medical device body has a bendable part in which flexibility of the medical device body is locally high in a region between the first operating line and the second operating line or a region located opposite to the region between the first operating line and the second operating line with respect to an axis of the medical device body, in the circumferential direction of the distal end part of the medical device body.

26. The medical device according to claim 25, wherein the bendable part comprises a notched part formed on an outer surface side of the medical device body.

27. The medical device according to claim 14, wherein the medical device body comprises a third hollow tube and a fourth hollow tube that are buried in the axial direction of the medical device body and allow a third operating line and a fourth operating line to be respectively inserted therethrough, the medical device further comprises a second bending operating comprising a device that pulls the third operating line and the fourth operating line such that a second bending operation of the distal end part of the medical device body is performed in a direction different from a direction of the bending of the distal end part of the medical device body in the bending operation, at the intermediate part and the proximal end part in the axial direction of the medical device body, the third operating line and the fourth operating line extend in parallel such that the third operating line and the fourth operating line are spaced apart from each other in the circumferential direction of the medical device body, in the curved region, the third operating line and the fourth operating line are gradually curved such that the third operating line and the fourth operating line approach each other in the circumferential direction of the medical device body toward the distal end side, and a distal end of the third operating line and a distal end of the fourth operating line are spaced apart from each other in the circumferential direction of the medical device body, and are fixed to the medical device body.

28. The medical device according to claim 27, wherein the third operating line and the fourth operating line are pulled at a time by an operation on the second bending operating part.

* * * * *